United States Patent
Shulman et al.

(10) Patent No.: US 9,194,011 B2
(45) Date of Patent: Nov. 24, 2015

(54) STABILIZED ALPHA-GALACTOSIDASE AND USES THEREOF

(75) Inventors: Avidor Shulman, Rakefet (IL); Ilya Ruderfer, Carmiel (IL); Tehila Ben-Moshe, Koranit (IL); Talia Shekhter, Givataim (IL); Yaniv Azulay, Akko (IL); Yoseph Shaaltiel, Kibbutz HaSolelim (IL); Tali Kizhner, Yishuv Atzmon-Segev (IL)

(73) Assignee: Protalix Ltd., Carmiel (IL)

( * ) Notice: Subject to any disclaimer, the term of this patent is extended or adjusted under 35 U.S.C. 154(b) by 0 days.

(21) Appl. No.: 13/582,482

(22) PCT Filed: Mar. 2, 2011

(86) PCT No.: PCT/IL2011/000209
§ 371 (c)(1),
(2), (4) Date: Sep. 4, 2012

(87) PCT Pub. No.: WO2011/107990
PCT Pub. Date: Sep. 9, 2011

(65) Prior Publication Data
US 2012/0328592 A1    Dec. 27, 2012

Related U.S. Application Data

(63) Continuation-in-part of application No. PCT/IL2010/000956, filed on Nov. 17, 2010.

(60) Provisional application No. 61/434,499, filed on Jan. 20, 2011, provisional application No. 61/434,503, filed on Jan. 20, 2011, provisional application No. 61/309,487, filed on Mar. 2, 2010, provisional application No. 61/261,787, filed on Nov. 17, 2009.

(51) Int. Cl.
A61K 38/54     (2006.01)
C12N 9/96      (2006.01)
C12N 9/40      (2006.01)
C07H 21/04     (2006.01)
C07K 1/00      (2006.01)

(52) U.S. Cl.
CPC ....... *C12Y 302/01022* (2013.01); *C12N 9/2465* (2013.01)

(58) Field of Classification Search
CPC ................ C12Y 302/01022; C12N 9/2465
USPC .............. 424/94.3; 435/188, 208; 536/23.2; 530/350
See application file for complete search history.

(56) References Cited

U.S. PATENT DOCUMENTS

| 5,580,757 A | 12/1996 | Desnick et al. |
|---|---|---|
| 5,595,756 A | 1/1997 | Bally et al. |
| 5,614,587 A | 3/1997 | Rhee et al. |
| 5,705,153 A | 1/1998 | Shorr et al. |
| 5,766,897 A | 6/1998 | Braxton |
| 5,994,086 A | 11/1999 | Benoff |
| 6,309,646 B1 | 10/2001 | Lees |
| 6,395,884 B1 | 5/2002 | Selden et al. |
| 6,458,574 B1 | 10/2002 | Selden et al. |
| 6,583,158 B1 * | 6/2003 | Fan et al. ............. 514/315 |
| 6,846,968 B1 | 1/2005 | Erwin et al. |
| 7,011,831 B2 | 3/2006 | Calhoun et al. |
| 7,087,728 B2 * | 8/2006 | Margolin et al. ......... 530/395 |
| 7,341,720 B2 * | 3/2008 | Stefano ................ 424/94.3 |
| 7,935,336 B2 * | 5/2011 | Sakuraba et al. ....... 424/94.61 |
| 8,426,357 B2 * | 4/2013 | Kraehmer et al. ....... 514/1.1 |
| 2002/0088024 A1 | 7/2002 | Garger et al. |
| 2002/0137125 A1 | 9/2002 | Zhu |
| 2003/0190304 A1 | 10/2003 | Thompson et al. |
| 2005/0048047 A1 | 3/2005 | Kakkis |
| 2005/0058634 A1 | 3/2005 | Zhu |
| 2005/0059097 A1 | 3/2005 | Daunert et al. |
| 2005/0180948 A1 | 8/2005 | Desjarlais et al. |
| 2005/0282225 A1 | 12/2005 | Daunert et al. |
| 2006/0084163 A1 | 4/2006 | Schaffer et al. |
| 2006/0204487 A1 | 9/2006 | Shaaltiel et al. |
| 2006/0228348 A1 | 10/2006 | Stefano |
| 2007/0172449 A1 | 7/2007 | Carmichael et al. |
| 2007/0207961 A1 | 9/2007 | Dahiyat et al. |
| 2008/0038232 A1 | 2/2008 | Shaaltiel et al. |
| 2012/0230974 A1 | 9/2012 | Shaaltiel et al. |
| 2012/0328589 A1 | 12/2012 | Ruderfer et al. |
| 2013/0017169 A1 | 1/2013 | Ruderfer et al. |

FOREIGN PATENT DOCUMENTS

| EP | 0747066 | 12/1996 |
|---|---|---|
| EP | 1172372 | 1/2002 |
| EP | 1955712 | 8/2008 |
| GB | 2402677 | 12/2004 |
| JP | 2005-043317 | 2/2005 |
| KR | 20070065157 | 6/2007 |
| WO | WO 91/14697 | 10/1991 |
| WO | WO 93/18148 | 9/1993 |
| WO | WO 95/01994 | 1/1995 |
| WO | WO 95/06478 | 3/1995 |

(Continued)

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*

(Continued)

*Primary Examiner* — Ganapathirama Raghu

(57) ABSTRACT

Multimeric protein structures comprising at least two alpha-galactosidase monomers being covalently linked to one another via a linking moiety are disclosed herein, as well a process for preparing same, and methods of treating Fabry disease via administration of a multimeric protein structure. The disclosed multimeric protein structures exhibit an improved performance, in terms of enhanced activity and/or a longer lasting activity under both lysosomal conditions and in a serum environment.

41 Claims, 45 Drawing Sheets

(56) References Cited

FOREIGN PATENT DOCUMENTS

| WO | WO 96/23869 | 8/1996 |
|---|---|---|
| WO | WO 97/10353 | 3/1997 |
| WO | WO 98/13469 | 4/1998 |
| WO | WO 00/59926 | 10/2000 |
| WO | WO 01/25277 | 4/2001 |
| WO | WO 02/057435 | 7/2002 |
| WO | WO 03/035686 | 5/2003 |
| WO | WO 03/042244 | 5/2003 |
| WO | WO 03/090695 | 11/2003 |
| WO | WO 03/097791 | 11/2003 |
| WO | WO 2004/081053 | 9/2004 |
| WO | WO 2004/091475 | 10/2004 |
| WO | WO 2004/096978 | 11/2004 |
| WO | WO 2004/111198 | 12/2004 |
| WO | WO 2005/056760 | 6/2005 |
| WO | WO 2005/077093 | 8/2005 |
| WO | WO 2005/093422 | 10/2005 |
| WO | WO 2006/093524 | 9/2006 |
| WO | WO 2006/108052 | 10/2006 |
| WO | WO 2007/010533 | 1/2007 |
| WO | WO 2008/012540 | 1/2008 |
| WO | WO 2008/075957 | 6/2008 |
| WO | WO 2008/082274 | 7/2008 |
| WO | WO 2008/089403 | 7/2008 |
| WO | WO 2008/096012 | 8/2008 |
| WO | WO 2008/132743 | 11/2008 |
| WO | WO 2009/024977 | 2/2009 |
| WO | WO 2010/004568 | 1/2010 |
| WO | WO 2011/107992 | 9/2011 |
| WO | WO 2012/098537 | 7/2012 |

OTHER PUBLICATIONS

Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Xu et al., Dumbbell-like-Au—Fe3O4 nanoparticles for target specific platin delivery. JACS., 2009, vol. 131: 4216-4217.*
Notice of Reason for Rejection Dated Apr. 8, 2014 From the Japanese Patent Office Re. Application No. 2012-555542 and Its Translation Into English.
Restriction Official Action Dated Apr. 12, 2013 From the US Patent and Trademark Office Re. U.S. Appl. No. 13/582,464.
Official Action Dated Feb. 19, 2014 From the US Patent and Trademark Office Re. U.S. Appl. No. 13/582,464.
Search Report and Written Opinion Dated Mar. 3, 2014 From the Intellectual Property Office of Singapore Issued by Hungarian Intellectual Property Office Re. Application No. 201206458-0.
Garman et al. "The Molecular Defect Leading to Fabry Disease: Structure of Human Alpha-Galactosidase", The Journal of Molecular Biology, 33(2): 319-335, Mar. 19, 2004.
Mayes et al. "Alpha-Galactosidase A From Human Placenta. Stability and Subunit Size", Biochimica et Biophysica Acta, 484(2): 408-416, Oct. 13, 1977. Abstract, p. 414, Fig.3.
Murali et al. "Crystallization and Preliminary X-Ray Analysis of Human Alpha-Galactosidase A Complex", The Journal of Molecular Biology, 239(4): 578-580, Jun. 16, 1994. Abstract, Fig.1.
Pierce "Crosslinking Reagents", The Pierce Technical Handbook, 48 P, 2006.
Translation of Notification of Office Action Dated Aug. 28, 2013 From the State Intellectual Property Office of the People's Republic of China Re. Application No. 201180022145.6.
Communication Pursuant to Article 94(3) EPC Dated Oct. 7, 2010 From the European Patent Office Re. Application No. 08789815.1.

Communication Relating to the Results of the Partial International Search Dated Sep. 18, 2009 From the International Searching Authority Re.: Application No. PCT/IL2008/001143.
Communication Relating to the Results to the Partial international Search Dated Jul. 4, 2011 From the International Searching Authority Re. Application No. PCT/IL2011/000211.
International Preliminary Report on Patentability Dated Mar. 4, 2010 From the International Bureau of WIPO Re.: Application No. PCT/IL2008/001143.
International Preliminary Report on Patentability Dated Sep. 13, 2012 From the International Bureau of WIPO Re. Application No. PCT/IL2011/000209.
International Preliminary Report on Patentability Dated Sep. 13, 2012 From the International Bureau of WIPO Re. Application No. PCT/IL2011/000210.
International Preliminary Report on Patentability Dated Sep. 13, 2012 From the International Bureau of WIPO Re. Application No. PCT/IL2011/000211.
International Preliminary Report on Patentability Dated May 31, 2012 From the International Bureau of WIPO Re. Application No. PCT/IL2010/000956.
International Search Report and the Written Opinion Dated Feb. 2, 2012 From the International Searching Authority Re. Application No. PCT/IL2011/000719.
International Search Report and the Written Opinion Dated Mar. 14, 2011 From the International Searching Authority Re. Application No. PCT/IL2010/000956.
International Search Report and the Written Opinion Dated Jun. 22, 2011 From the International Searching Authority Re. Application No. PCT/IL2011/000210.
International Search Report and the Written Opinion Dated Nov. 23, 2009 From the International Searching Authority Re.: Application No. PCT/IL2008/001143.
International Search Report and the Written Opinion Dated Jun. 24, 2011 From the International Searching Authority Re. Application No. PCT/IL2011/000209.
International Search Report and the Written Opinion Dated Sep. 28, 2011 From the International Searching Authority Re. Application No. PCT/IL2011/000211.
Official Action Dated Jul. 16, 2012 From the US Patent and Trademark Office Re. U.S. Appl. No. 12/673,987.
Response Dated Feb. 3, 2011 to Communication Pursuant to Article 94(3) EPC of Oct. 7, 2010 From the European Patent Office Re. Application No. 08789815.1.
Restriction Official Action Dated Apr. 17, 2012 From the US Patent and Trademark Office Re. U.S. Appl. No. 12/673,987.
B?ckmann et al. "Functionalization of Poly(Ethylene Glycol) and Monomethoxy-Poly(Ethylene Glycol)", Die Makromolekulare Chemie, 182(5): 1379-1384, May 1981.
B?ckmann et al. "Synthesis of Water Soluble Polymers With Covalently Bound General Ligands", Enzyme Engineering, 4: 395-397, 1978.
Bendele et al. "Short Communication: Renal Tubular Vacuolation in Animals Treated With Polyethylene-Glycol-Conjugated Proteins", Toxicological Sciences, 42: 152-157, 1998.
Benoff et al. "Use of Mannose Ligands in IVF Screens to Mimic Zona Pellucida-Induced Acrosome Reactions and Predict Fertilization Success", Molecular Human Reproduction, XP002554818, 3(10): 839-846, Oct. 1997. Abstract.
Chen et al. "Directed Evolution of a Lysosomal Enzyme With Enhanced Activity at Neutral pH by Mammalian Cell-Surface Display", Chemistry and Biology, 15: 1277-1286, 2008.
Cramer et al. "Transgenic Plants for Therapeutic Proteins: Linking Upstream and Downstream Strategies", Current Topics in Microbiology and Immunology, XP009038354, 240(3): 95-118, 1999.
Den Dulk-Ras et al. "Electroporation of Agrobacterium Tumefaciens", Methods in Molecular Biology, 55: 63-72, 1995. Abstract.
Fernandez-Megia et al. "Conjugation of Bioactive Ligands to PEG-Grafted Chitosan at the Distal End of PEG", Biomacromolecules, XP002554819, 8(3): 833-842, Mar. 2007.

(56) References Cited

OTHER PUBLICATIONS

Gao et al. "A Novel Alkaline ?-Galactosidase From Melon Fruit With a Substrate Preference for Raffinose", Plant Physiology, XP002128580, 119(3): 979-987, Mar. 1, 1999. Abstract, p. 980-981: "Alkaline ?-Galactosidase Purification".
Gleba et al. "Magnifection—A New Platform for Expressing Recombinant Vaccines in Plants", Vaccine, 23: 2042-2048, 2005.
Grosse et al. "Intracellular Rate-Limiting Steps of Gene Transfer Using Glycosylated Polylysines in Cystic Fibrosis Airway Epithelial Cells", Gene Therapy, XP002554817, 9(15): 1000-1007, Aug. 2002. p. 1005, col. 1, § 4.
Hoffmann "Fabry Disease: Recent Advances in Pathology, Diagnosis, Treatment and Monitoring", Orphanet Journal of Rare Diseases, 4(21): 1-9, Oct. 11, 2009.
Kapoor "How to Cross-Link Proteins", FGSC (Fungal Genetics Stock Center), University of Missouri, MO, USA, p. 1-6, Mar. 28, 2006. Retrieved From the Internet.
Laville et al. "Photodynamic Efficiency of Diethylene-Linked Glycoconjugated Porphyrins in Human Retinoblastoma Cells", Journal of Medicinal Chemistry, XP002554822, 49(8): 2558-2567, Apr. 2006. Figs.1-3.
Li et al. "Bacteria Targeted by Human Natural Antibodies Using ?-Gal Conjugated Receptor-Specific Glycopolymers", Bioorganic and Medicinal Chemistry, XP002554821, 7(8): 1549-1558, Aug. 1999. Figs.1-5.
Lindhorst et al. "Trivalent ?-D-Mannoside Clusters as Inhibitors of Type-1 Fimbriae-Mediated Adhesion of *Escherichia coli*: Structural Variation and Biotinylation", Journal of the chemical Society, Perkin Transactions 1, XP002554820, 8: 823-831, Apr. 21, 2001.
Neumann et al. "Protein Transport in Plant Cells: In and Out of the Golgi", Annals of Botany, 92: 167-180, 2003.
Pagny et al. "Signals and Mechanisms for Protein Retention in the Endoplasmic Reticulum", Journal of Experimental Botany, 50(331): 157-164, Feb. 1999.
Potrykus "Gene Transfer to Plants: Assessment of Public Approaches and Results", Annual Review of Plant Physiology & Plant Molecular Biology, 42: 205-225, 1991.
Rathnam et al. "Conjugation of a Fetuin Glycopeptide to Human Follicle-Stimulating Hormone and Its Subunits by Photoactivation", Biochimica et Biophysica Acta, XP002554815, 624(2): 436-442, 1980. Fig.1.
Rayon et al. "The Protein N-Glycosylation in Plants", Journal of Experimental Botany, 49(326): 1463-1472, Sep. 1998.
Schottelius et al. "Detection and Quantitation of Cell-Surface Sugar Receptor(s) of Leishmania Donovani by Application of Neoglycoenzymes", Parasitology Research, XP008114350, 78(6): 529-533, 1992.
Shimamoto et al. "Fertile Transgenic Rice Plants Regenerated From Transformed Protoplasts", Nature, 338: 274-276, Mar. 16, 1989.
Sigma-Aldrich "Innovations in Peptide Synthesis and Conjugation: Tools for Drug Discovery", ChemFiles, 5(12): 1-24, 2005.
Takahashi et al. "A New Method for the Formation of the ?-Glycose Bond of Sialyl Conjugates Based on Long-Range Participation", Tetrahedron Letters, XP004094811, 38(47): 8223-8226, Nov. 24, 1997. Fig.2, Compound 9.
Takahashi et al. "Design and Synthesis of a Water-Soluble Taxol Analogue: Taxol-Sialyl Conjugate", Bioorganic & Medicinal Chemistry Letters, XP004136633, 8(1-6): 113-116, Jan. 6, 1998. Fig.1, Compounds 1, 2.
Tardi et al. "Liposomal Encapsulation of Topotecan Enhances Anticancer Efficacy in Murine and Human Xenograft Models", Cancer Research, 60: 3389-3393, 2000.
Thermo Fisher Scientific "Instructions BM(PEG)2 and BM(PEG)3", Thermo Fisher Scientific Inc., Pierce Biotechnology, Rockford, IL, USA, 3 P., 2007.
Thermo Fisher Scientific "Instructions BS(PEG)n. Homofunctional, Amine-Reactive Crosslinkers With Polyethylene Glycol (PEG) Spacer Arms", Thermo Fisher Scientific Inc., Pierce Biotechnology, Rockford, IL, USA, 3 P., 2008.
UniProt "Name-ERABP1; OrderedLocusNames=At4g02980; ORFNames=T4I9.14; Arabidopsis Thaliana (Mouse-Ear Cress)", UniProtKB / Swiss-Prot, ID ABP1_ARATII, Accession No. P33487, Feb. 1, 1994.
Vamvakaki et al. "Fluorescence Detection of Enzymatic Activity Within a Liposome Based Nano-Biosensor", Biosensors and Bioelectronics 21: 384-388, 2005.
Vargas et al. "Endocytosis of Liposomes Containing Lyposomal Proteins Increases Intracellular Protein Degradation in growing L-132 Cells", European Journal of Biochemistry, 188: 99-109, 1990.
Yamaguchi et al. "Polysaccharide-Poly(Ethylene Glycol) Star Copolymer as a Scaffold for the Production of Bioactive Hydrogels", Biomacromolecules, 6: 1921-1930, 2005.
Zambrano et al. "Receptor Binding Activity and In Vitro Biological Activity of the Human FSH Charge Isoforms as Disclosed by Heterologous and Homologous Assay Systems. Implications for the Structure-Function Relationship of the FSH Variants", Endocrine, XP002554816, 10(2): 113-121, 1999. p. 114, col. 1, § 2, Fig.1.
Official Action Dated Jul. 18, 2013 From the US Patent and Trademark Office Re. U.S. Appl. No. 13/582,464.
Restriction Official Action Dated Sep. 3, 2014 From the US Patent and Trademark Office Re. U.S. Appl. No. 13/582,441.
Auclair et al. "Strategies for Stabilizing Superoxide Dismutase (SOD1), the Protein Destabilized in the Most Common Form of Familial Amytrophic Lateral Sclerosis", Proc. Natl. Acad. Sci. USA, PNAS Early Edition, 107(5): 21394-21399, Dec. 14, 2010.
Benesch et al. "Hemoglobin Tetramers Stabilized by a Single Intramolecular Cross-Link", Journal of Protein Chemistry, 10(5): 503-510, 1991.
Brown et al. "Biochemistry of Protein-Isocyanate Interactions: A Comparison of the Effects of Aryl Vs. Alkyl Isocyanates", Environmental Health Perspectives, 72: 5-11, Jun. 1987.
Invitrogen "Fluorophores and Their Amine-Reactive Derivatives", The Molecular Probes® Handbook, A Guide Fluorescent Probes and Labeling Technologies, 11th Edition, Chap.1: 15-96, 2010.
Mayes et al. "Endocytosis of Lysosomal Alpha-Glactosidase A by Cultured Fibroblasts Fom Patients With Fabry Disease", American Journal of Human Genetics, 34: 602-610, 1982.
Snyder Jr. et al. "Enzyme Therapy II: Purified Human Alpha-Galactosidase A. Stabilization to Heat and Protease Degradation by Complexing With Antibody and by Chemical Modification", Biochimica et Biophysica Acta, 350: 432-436, 1974.
Wang et al. "Human Alpha-N-Acetylgalactosaminidase-Molecular Cloning, Nucleotide Sequence, and Expression of a Full-Length cDNA. Homology With Human Alpha-Galactosidase A Suggests Evolution From a Common Ancestral Gene", The Journal of Biological Chemistry, 265(35): 21859-21866, Dec. 15, 1990.
Official Action Dated Feb. 4, 2015 From the US Patent and Trademark Office Re. U.S. Appl. No. 13/582,441.
Notification of Office Action Dated Nov. 26, 2014 From the State Intellectual Property Office of the People's Republic of China Re. Application No. 201180022145.6.
Decision of Rejection Dated Nov. 7, 2014 From the Japanese Patent Office Re. Application No. 2012-555542 and Its Translation Into English.
Translation Dated Dec. 10, 2014 of Notification of Office Action Dated Nov. 26, 2014 From the State Intellectual Property Office of the People's Republic of China Re. Application No. 201180022145.6.
European Search Report Dated Mar. 31, 2015 From the European Patent Office Re. Application No. 14195875.1.
Notification of Office Action Dated Mar. 18, 2015 From the State Intellectual Property Office of the People's Republic of China Re. Application No. 201180069560.7 and Its Translation Into English.
Request for Examination Dated Feb. 24, 2015 From the ROSPATENT, Federal Government Institution, Federal Institute of Industrial Property of the Federal Service for Intellectual Property, Patents and Trademarks of the Russian Federation Re. Application No. 2012141651 and Its Translation Into English.
Search and Examination Report Dated Sep. 19, 2014 From the Intellectual Property Office of Singapore Re. Application No. 201206458-0.

\* cited by examiner

SEQUENCE LISTING

<160> NUMBER OF SEQ ID NOS: 15

<210> SEQ ID NO 1
<211> LENGTH: 405
<212> TYPE: PRT
<213> ORGANISM: Artificial sequence
<220> FEATURE:
<223> OTHER INFORMATION: Plant recombinant human alpha-GAL
      (prh-alpha-GAL)

<400> SEQUENCE: 1

Glu Phe Leu Asp Asn Gly Leu Ala Arg Thr Pro Thr Met Gly Trp Leu
1               5                   10                  15

His Trp Glu Arg Phe Met Cys Asn Leu Asp Cys Gln Glu Glu Pro Asp
            20                  25                  30

Ser Cys Ile Ser Glu Lys Leu Phe Met Glu Met Ala Glu Leu Met Val
        35                  40                  45

Ser Glu Gly Trp Lys Asp Ala Gly Tyr Glu Tyr Leu Cys Ile Asp Asp
    50                  55                  60

Cys Trp Met Ala Pro Gln Arg Asp Ser Glu Gly Arg Leu Gln Ala Asp
65                  70                  75                  80

Pro Gln Arg Phe Pro His Gly Ile Arg Gln Leu Ala Asn Tyr Val His
                85                  90                  95

```
Ser Lys Gly Leu Lys Leu Gly Ile Tyr Ala Asp Val Gly Asn Lys Thr
                100                 105                 110

Cys Ala Gly Phe Pro Gly Ser Phe Gly Tyr Tyr Asp Ile Asp Ala Gln
            115                 120                 125

Thr Phe Ala Asp Trp Gly Val Asp Leu Leu Lys Phe Asp Gly Cys Tyr
        130                 135                 140

Cys Asp Ser Leu Glu Asn Leu Ala Asp Gly Tyr Lys His Met Ser Leu
145                 150                 155                 160

Ala Leu Asn Arg Thr Gly Arg Ser Ile Val Tyr Ser Cys Glu Trp Pro
                165                 170                 175

Leu Tyr Met Trp Pro Phe Gln Lys Pro Asn Tyr Thr Glu Ile Arg Gln
            180                 185                 190

Tyr Cys Asn His Trp Arg Asn Phe Ala Asp Ile Asp Asp Ser Trp Lys
        195                 200                 205

Ser Ile Lys Ser Ile Leu Asp Trp Thr Ser Phe Asn Gln Glu Arg Ile
    210                 215                 220

Val Asp Val Ala Gly Pro Gly Gly Trp Asn Asp Pro Asp Met Leu Val
225                 230                 235                 240

Ile Gly Asn Phe Gly Leu Ser Trp Asn Gln Gln Val Thr Gln Met Ala
                245                 250                 255

Leu Trp Ala Ile Met Ala Ala Pro Leu Phe Met Ser Asn Asp Leu Arg
            260                 265                 270

His Ile Ser Pro Gln Ala Lys Ala Leu Leu Gln Asp Lys Asp Val Ile
        275                 280                 285

Ala Ile Asn Gln Asp Pro Leu Gly Lys Gln Gly Tyr Gln Leu Arg Gln
    290                 295                 300

Gly Asp Asn Phe Glu Val Trp Glu Arg Pro Leu Ser Gly Leu Ala Trp
305                 310                 315                 320

Ala Val Ala Met Ile Asn Arg Gln Glu Ile Gly Gly Pro Arg Ser Tyr
                325                 330                 335

Thr Ile Ala Val Ala Ser Leu Gly Lys Gly Val Ala Cys Asn Pro Ala
            340                 345                 350

Cys Phe Ile Thr Gln Leu Leu Pro Val Lys Arg Lys Leu Gly Phe Tyr
        355                 360                 365

Glu Trp Thr Ser Arg Leu Arg Ser His Ile Asn Pro Thr Gly Thr Val
    370                 375                 380

Leu Leu Gln Leu Glu Asn Thr Met Gln Met Ser Leu Lys Asp Leu Ser
385                 390                 395                 400

Glu Lys Asp Glu Leu
                405

<210> SEQ ID NO 2
<211> LENGTH: 404
<212> TYPE: PRT
<213> ORGANISM: Artificial sequence
<220> FEATURE:
<223> OTHER INFORMATION: Plant recombinant human alpha-GAL
      (prh-alpha-GAL)

<400> SEQUENCE: 2

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45
```

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
        355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu Ser Glu
385                 390                 395                 400

Lys Asp Glu Leu

<210> SEQ ID NO 3
<211> LENGTH: 405
<212> TYPE: PRT
<213> ORGANISM: Artificial sequence
<220> FEATURE:
<223> OTHER INFORMATION: Plant recombinant human alpha-GAL
      (prh-alpha-GAL)

<400> SEQUENCE: 3

```
Gly Leu Asp Asn Gly Leu Ala Arg Thr Pro Thr Met Gly Trp Leu His
1               5                   10                  15

Trp Glu Arg Phe Met Cys Asn Leu Asp Cys Gln Glu Gly Pro Asp Ser
                20                  25                  30

Cys Ile Ser Glu Lys Leu Phe Met Glu Met Ala Glu Leu Met Val Ser
            35                  40                  45

Glu Gly Trp Lys Asp Ala Gly Tyr Glu Tyr Leu Cys Ile Asp Asp Cys
        50                  55                  60

Trp Met Ala Pro Gln Arg Asp Ser Glu Gly Arg Leu Gln Ala Asp Pro
65                  70                  75                  80

Gln Arg Phe Pro His Gly Ile Arg Gln Leu Ala Asn Tyr Val His Ser
                85                  90                  95

Lys Gly Leu Lys Leu Gly Ile Tyr Ala Asp Val Gly Asn Lys Thr Cys
                100                 105                 110

Ala Gly Phe Pro Gly Ser Phe Gly Tyr Tyr Asp Ile Asp Ala Gln Thr
            115                 120                 125

Phe Ala Asp Trp Gly Val Asp Leu Leu Lys Phe Asp Gly Cys Tyr Cys
130                 135                 140

Asp Ser Leu Glu Asn Leu Ala Asp Gly Tyr Lys His Met Ser Leu Ala
145                 150                 155                 160

Leu Asn Arg Thr Gly Arg Ser Ile Val Tyr Ser Cys Glu Trp Pro Leu
                165                 170                 175

Tyr Met Trp Pro Phe Gln Lys Pro Asn Tyr Thr Glu Ile Arg Gln Tyr
            180                 185                 190

Cys Asn His Trp Arg Asn Phe Ala Asp Ile Asp Asp Ser Trp Lys Ser
            195                 200                 205

Ile Lys Ser Ile Leu Asp Trp Thr Ser Phe Asn Gln Glu Arg Ile Val
210                 215                 220

Asp Val Ala Gly Pro Gly Gly Trp Asn Asp Pro Asp Met Leu Val Ile
225                 230                 235                 240

Gly Asn Phe Gly Leu Ser Trp Asn Gln Gln Val Thr Gln Met Ala Leu
                245                 250                 255

Trp Ala Ile Met Ala Ala Pro Leu Phe Met Ser Asn Asp Leu Arg His
            260                 265                 270

Ile Ser Pro Gln Ala Lys Ala Leu Leu Gln Asp Lys Asp Val Ile Ala
            275                 280                 285

Ile Asn Gln Asp Pro Leu Gly Lys Gln Gly Tyr Gln Leu Arg Gln Gly
            290                 295                 300

Asp Asn Phe Glu Val Trp Glu Arg Pro Leu Ser Gly Leu Ala Trp Ala
305                 310                 315                 320

Val Ala Met Ile Asn Arg Gln Glu Ile Gly Gly Pro Arg Ser Tyr Thr
                325                 330                 335

Ile Ala Val Ala Ser Leu Gly Lys Gly Val Ala Cys Asn Pro Ala Cys
            340                 345                 350

Phe Ile Thr Gln Leu Leu Pro Val Lys Arg Lys Leu Gly Phe Tyr Glu
            355                 360                 365

Trp Thr Ser Arg Leu Arg Ser His Ile Asn Pro Thr Gly Thr Val Leu
            370                 375                 380

Leu Gln Leu Glu Asn Thr Met Gln Met Ser Leu Lys Asp Leu Leu Ser
385                 390                 395                 400

Glu Lys Asp Glu Leu
                405
```

<210> SEQ ID NO 4
<211> LENGTH: 753
<212> TYPE: PRT
<213> ORGANISM: Cucumis melo

<400> SEQUENCE: 4

```
Met Thr Val Gly Ala Gly Ile Thr Ile Ser Asp Ala Asn Leu Thr Val
1               5                   10                  15

Leu Gly Asn Arg Val Leu Ser Asp Val His Asn Asn Ile Thr Leu Thr
            20                  25                  30

Ala Ala Pro Gly Gly Gly Val Met Asn Gly Ala Phe Ile Gly Val Gln
        35                  40                  45

Ser Asp Gln Ile Gly Ser Arg Arg Val Phe Pro Ile Gly Lys Leu Ile
50                  55                  60

Gly Leu Arg Phe Leu Cys Ala Phe Arg Phe Lys Leu Trp Trp Met Thr
65                  70                  75                  80

Gln Arg Met Gly Cys Ser Gly Gln Glu Val Pro Phe Glu Thr Gln Phe
                85                  90                  95

Leu Val Val Glu Thr Arg Asp Gly Ser Asn Ile Ala Gly Asn Gly Glu
            100                 105                 110

Glu Gly Asp Ala Val Tyr Thr Val Phe Leu Pro Ile Leu Glu Gly Asp
        115                 120                 125

Phe Arg Ala Val Leu Gln Gly Asn Asp Asn Glu Ile Glu Ile Cys
130                 135                 140

Leu Glu Ser Gly Asp Pro Ser Val Asp Gly Phe Glu Gly Ser His Leu
145                 150                 155                 160

Val Phe Val Gly Ala Gly Ser Asp Pro Phe Glu Thr Ile Thr Tyr Ala
                165                 170                 175

Val Lys Ser Val Glu Lys His Leu Gln Thr Phe Ala His Arg Glu Arg
            180                 185                 190

Lys Lys Met Pro Asp Ile Leu Asn Trp Phe Gly Trp Cys Thr Trp Asp
        195                 200                 205

Ala Phe Tyr Thr Asp Val Thr Ser Asp Gly Val Lys Lys Gly Leu Glu
210                 215                 220

Ser Phe Glu Asn Gly Gly Ile Pro Pro Lys Phe Val Ile Asp Asp
225                 230                 235                 240

Gly Trp Gln Ser Val Ala Lys Asp Ala Thr Ser Ala Asp Cys Lys Ala
                245                 250                 255

Asp Asn Thr Ala Asn Phe Ala Asn Arg Leu Thr His Ile Lys Glu Asn
            260                 265                 270

Tyr Lys Phe Gln Lys Asp Gly Lys Glu Gly Glu Arg Ile Glu Asn Pro
        275                 280                 285

Ala Leu Gly Leu Gln His Ile Val Ser Tyr Met Lys Glu Lys His Ala
290                 295                 300

Thr Lys Tyr Val Tyr Val Trp His Ala Ile Thr Gly Tyr Trp Gly Gly
305                 310                 315                 320

Val Ser Ala Gly Val Lys Glu Met Glu Gln Tyr Glu Ser Lys Ile Ala
                325                 330                 335

Tyr Pro Val Ala Ser Pro Gly Val Glu Ser Asn Glu Pro Cys Asp Ala
            340                 345                 350

Leu Asn Ser Ile Thr Lys Thr Gly Leu Gly Leu Val Asn Pro Glu Lys
        355                 360                 365

Val Phe Asn Phe Tyr Asn Glu Gln His Ser Tyr Leu Ala Ser Ala Gly
370                 375                 380
```

Val Asp Gly Val Lys Val Asp Val Gln Asn Ile Leu Glu Thr Leu Gly
385                 390                 395                 400

Ala Gly His Gly Gly Arg Val Lys Leu Ala Arg Lys Tyr His Gln Ala
            405                 410                 415

Leu Glu Ala Ser Ile Ser Arg Asn Phe Gln Asp Asn Gly Ile Ile Ser
            420                 425                 430

Cys Met Ser His Asn Thr Asp Gly Leu Tyr Ser Ser Lys Arg Asn Ala
            435                 440                 445

Val Ile Arg Ala Ser Asp Asp Phe Trp Pro Arg Asp Pro Ala Ser His
450                 455                 460

Thr Ile His Ile Ala Ser Val Ala Tyr Asn Ser Leu Phe Leu Gly Glu
465                 470                 475                 480

Phe Met Gln Pro Asp Trp Asp Met Phe His Ser Leu His Pro Met Ala
            485                 490                 495

Glu Tyr His Gly Ala Ala Arg Ala Val Gly Gly Cys Ala Ile Tyr Val
            500                 505                 510

Ser Asp Lys Pro Gly Gln His Asp Phe Asn Leu Leu Lys Lys Leu Val
            515                 520                 525

Leu Pro Asp Gly Ser Ile Leu Arg Ala Lys Leu Pro Gly Arg Pro Thr
530                 535                 540

Lys Asp Cys Leu Phe Thr Asp Pro Ala Arg Asp Gly Lys Ser Leu Leu
545                 550                 555                 560

Lys Ile Trp Asn Leu Asn Asp Leu Ser Gly Val Gly Val Phe Asn
            565                 570                 575

Cys Gln Gly Ala Gly Trp Cys Lys Val Gly Lys Lys Asn Leu Ile His
            580                 585                 590

Asp Glu Asn Pro Asp Thr Ile Thr Gly Val Ile Arg Ala Lys Asp Val
            595                 600                 605

Ser Tyr Leu Trp Lys Ile Ala Gly Glu Ser Trp Thr Gly Asp Ala Val
            610                 615                 620

Ile Phe Ser His Leu Ala Gly Glu Val Val Tyr Leu Pro Gln Asp Ala
625                 630                 635                 640

Ser Met Pro Ile Thr Leu Lys Pro Arg Glu Phe Asp Val Phe Thr Val
            645                 650                 655

Val Pro Val Lys Glu Leu Val Asn Asp Ile Lys Phe Ala Pro Ile Gly
            660                 665                 670

Leu Ile Lys Met Phe Asn Ser Gly Ala Val Lys Glu Met Asn His
            675                 680                 685

Gln Pro Gly Ser Ser Asn Val Ser Leu Lys Val Arg Gly Ser Gly Pro
            690                 695                 700

Phe Gly Ala Tyr Ser Ser Ser Lys Pro Lys Arg Val Ala Val Asp Ser
705                 710                 715                 720

Glu Glu Val Glu Phe Met Tyr Asp Gly Gly Leu Ile Thr Ile Asp
            725                 730                 735

Leu Lys Val Pro Glu Lys Glu Leu Tyr Leu Trp Asp Ile Arg Ile Glu
            740                 745                 750

Leu

<210> SEQ ID NO 5
<211> LENGTH: 772
<212> TYPE: PRT
<213> ORGANISM: Cucumis melo

<400> SEQUENCE: 5

```
Met Thr Val Thr Pro Lys Ile Ser Val Asn Asp Gly Asn Leu Val Val
1               5                   10                  15

His Gly Lys Thr Ile Leu Thr Gly Val Pro Asp Asn Ile Val Leu Thr
            20                  25                  30

Pro Gly Ser Gly Leu Gly Leu Val Ala Gly Ala Phe Ile Gly Ala Thr
            35                  40                  45

Ala Ser Asn Ser Lys Ser Leu His Val Phe Pro Val Gly Val Leu Glu
        50                  55                  60

Gly Thr Arg Phe Leu Cys Cys Phe Arg Phe Lys Leu Trp Trp Met Thr
65                  70                  75                  80

Gln Arg Met Gly Thr Ser Gly Arg Asp Ile Pro Phe Glu Thr Gln Phe
                85                  90                  95

Leu Leu Met Glu Ser Lys Gly Asn Asp Gly Glu Asp Pro Asp Asn Ser
                100                 105                 110

Ser Thr Ile Tyr Thr Val Phe Leu Pro Leu Leu Glu Gly Gln Phe Arg
            115                 120                 125

Ala Ala Leu Gln Gly Asn Glu Lys Asn Glu Met Glu Ile Cys Leu Glu
        130                 135                 140

Ser Gly Asp Asn Thr Val Glu Thr Asn Gln Gly Leu Ser Leu Val Tyr
145                 150                 155                 160

Met His Ala Gly Thr Asn Pro Phe Glu Val Ile Thr Gln Ala Val Lys
                165                 170                 175

Ala Val Glu Lys His Thr Gln Thr Phe Leu His Arg Glu Lys Lys Lys
                180                 185                 190

Leu Pro Ser Phe Leu Asp Trp Phe Gly Trp Cys Thr Trp Asp Ala Phe
            195                 200                 205

Tyr Thr Asp Val Thr Ala Glu Gly Val Val Glu Gly Leu Lys Ser Leu
        210                 215                 220

Ser Glu Gly Gly Ala Pro Pro Lys Phe Leu Ile Ile Asp Asp Gly Trp
225                 230                 235                 240

Gln Gln Ile Glu Ala Lys Pro Lys Asp Ala Asp Cys Val Val Gln Glu
                245                 250                 255

Gly Ala Gln Phe Ala Ser Arg Leu Ser Gly Ile Lys Glu Asn His Lys
                260                 265                 270

Phe Gln Lys Asn Gly Asn Asn Tyr Asp Gln Val Pro Gly Leu Lys Val
            275                 280                 285

Val Val Asp Asp Ala Lys Lys Gln His Lys Val Lys Phe Val Tyr Ala
        290                 295                 300

Trp His Ala Leu Ala Gly Tyr Trp Gly Gly Val Lys Pro Ala Ser Pro
305                 310                 315                 320

Gly Met Glu His Tyr Asp Ser Ala Leu Ala Tyr Pro Val Gln Ser Pro
                325                 330                 335

Gly Met Leu Gly Asn Gln Pro Asp Ile Val Val Asp Ser Leu Ala Val
            340                 345                 350

His Gly Ile Gly Leu Val His Pro Lys Lys Val Phe Asn Phe Tyr Asn
        355                 360                 365

Glu Leu His Ser Tyr Leu Ala Ser Cys Gly Ile Asp Gly Val Lys Val
        370                 375                 380

Asp Val Gln Asn Ile Ile Glu Thr Leu Gly Ala Gly His Gly Gly Arg
385                 390                 395                 400

Val Thr Leu Thr Arg Ser Tyr His Gln Ala Leu Glu Ala Ser Ile Ala
                405                 410                 415
```

```
Arg Asn Phe Ser Asp Asn Gly Cys Ile Ala Cys Met Cys His Asn Thr
            420                 425                 430

Asp Ser Leu Tyr Ser Ala Lys Gln Thr Ala Val Val Arg Ala Ser Asp
435                 440                 445

Asp Tyr Tyr Pro Arg Asp Pro Ala Ser His Thr Ile His Ile Ser Ser
        450                 455                 460

Val Ala Tyr Asn Ser Leu Phe Leu Gly Glu Phe Met Gln Pro Asp Trp
465                 470                 475                 480

Asp Met Phe His Ser Leu His Pro Thr Ala Glu Tyr His Gly Ala Ala
                485                 490                 495

Arg Ala Ile Gly Gly Cys Ala Ile Tyr Val Ser Asp Lys Pro Gly Asn
            500                 505                 510

His Asn Phe Asp Leu Leu Lys Lys Leu Val Leu Pro Asp Gly Ser Val
        515                 520                 525

Leu Arg Ala Gln Leu Pro Gly Arg Pro Thr Arg Asp Ser Leu Phe Asn
530                 535                 540

Asp Pro Ala Arg Asp Gly Thr Ser Leu Leu Lys Ile Trp Asn Met Asn
545                 550                 555                 560

Lys Cys Ser Gly Val Val Gly Val Phe Asn Cys Gln Gly Ala Gly Trp
                565                 570                 575

Cys Arg Ile Thr Lys Lys Thr Arg Ile His Asp Glu Ser Pro Gly Thr
            580                 585                 590

Leu Thr Thr Ser Val Arg Ala Ala Asp Val Asp Ala Ile Ser Gln Val
        595                 600                 605

Ala Gly Ala Asp Trp Lys Gly Asp Thr Ile Val Tyr Ala Tyr Arg Ser
610                 615                 620

Gly Asp Leu Ile Arg Leu Pro Lys Gly Ala Ser Val Pro Val Thr Leu
625                 630                 635                 640

Lys Val Leu Glu Tyr Asp Leu Leu His Ile Ser Pro Leu Lys Asp Ile
                645                 650                 655

Ala Ser Asn Ile Ser Phe Ala Pro Ile Gly Leu Leu Asp Met Phe Asn
            660                 665                 670

Thr Gly Gly Ala Val Glu Gln Val Asn Val Gln Val Val Glu Pro Ile
        675                 680                 685

Pro Glu Phe Asp Gly Glu Val Ala Ser Glu Leu Thr Cys Ser Leu Pro
690                 695                 700

Asn Asp Arg Pro Pro Thr Ala Thr Ile Thr Met Lys Ala Arg Gly Cys
705                 710                 715                 720

Arg Arg Phe Gly Leu Tyr Ser Ser Gln Arg Pro Leu Lys Cys Ser Val
                725                 730                 735

Asp Lys Val Asp Val Asp Phe Val Tyr Asp Glu Val Thr Gly Leu Val
            740                 745                 750

Thr Phe Glu Ile Pro Ile Pro Thr Glu Glu Met Tyr Arg Trp Asn Ile
        755                 760                 765

Glu Ile Gln Val
    770

<210> SEQ ID NO 6
<211> LENGTH: 767
<212> TYPE: PRT
<213> ORGANISM: Tetragonia tetragonioides

<400> SEQUENCE: 6

Met Thr Ile Thr Pro Ser Ile Ser Val Ser Asn Gly Asn Leu Val Val
1               5                   10                  15
```

```
His Gly Lys Thr Ile Leu Thr Gly Val Pro Asp Asn Ile Ile Leu Thr
             20                  25                  30

Pro Gly Ser Gly Ala Gly Leu Ala Gly Ala Phe Ile Gly Ala Thr
         35                  40                  45

Ala Asp Asp Ser Lys Cys Leu His Val Phe Pro Met Gly Thr Leu Glu
 50                  55                  60

Gly Leu Arg Phe Met Cys Cys Leu Arg Phe Lys Leu Trp Trp Met Thr
 65                  70                  75                  80

Gln Arg Met Gly Lys Cys Gly Lys Asp Ile Pro Leu Glu Thr Gln Phe
                 85                  90                  95

Met Ile Val Glu Ser Lys Asp Thr Val Glu Gly Glu Pro Asp Asp
             100                 105                 110

Ser Pro Thr Ile Tyr Thr Val Phe Leu Pro Leu Leu Glu Gly Gln Phe
         115                 120                 125

Arg Ala Val Leu Gln Gly Thr Glu Lys Asn Glu Ile Glu Ile Cys Leu
 130                 135                 140

Glu Ser Gly Asp Thr Thr Val Gln Thr Ser Gln Gly Leu His Leu Val
145                  150                 155                 160

Tyr Met His Ala Gly Thr Asn Pro Tyr Glu Val Ile Asn Gln Ala Val
                 165                 170                 175

Lys Ala Val Glu Lys His Met Gln Thr Phe Arg His Arg Glu Lys Lys
             180                 185                 190

Arg Leu Pro Ser Phe Val Asp Trp Phe Gly Trp Cys Thr Trp Asp Ala
         195                 200                 205

Phe Tyr Thr Asp Val Thr Ala Glu Gly Val Asp Glu Gly Leu Arg Ser
 210                 215                 220

Leu Ser Glu Gly Gly Thr Pro Pro Arg Phe Leu Ile Ile Asp Asp Gly
225                  230                 235                 240

Trp Gln Gln Ile Gly Asn Glu Ile Val Lys Asp Glu Asn Cys Met Val
                 245                 250                 255

Gln Glu Gly Ala Gln Phe Ala Asn Arg Leu Thr Gly Ile Lys Glu Asn
             260                 265                 270

Ala Lys Phe Gln Lys Lys Asn Gly Glu Asp Lys Asp Gln Val Pro
         275                 280                 285

Gly Leu Lys His Val Val Glu Glu Ala Lys Gln Arg His Asn Val Lys
 290                 295                 300

Ser Val Tyr Val Trp His Ala Leu Ala Gly Tyr Trp Gly Gly Val Lys
305                  310                 315                 320

Pro Ala Ala Ala Gly Met Glu His Tyr Asp Thr Ala Leu Ala Tyr Pro
                 325                 330                 335

Val Gln Ser Pro Gly Val Leu Gly Asn Gln Pro Asp Val Met Asp
             340                 345                 350

Ser Leu Ser Val His Gly Leu Gly Leu Val His Pro Lys Lys Val Phe
         355                 360                 365

Asn Phe Tyr Asn Glu Leu His Ala Tyr Leu Ala Ala Cys Gly Val Asp
 370                 375                 380

Gly Val Lys Val Asp Val Gln Asn Ile Ile Glu Thr Leu Gly Ala Gly
385                  390                 395                 400

His Gly Gly Arg Val Ser Leu Thr Arg Ala Tyr His Gln Ala Leu Glu
                 405                 410                 415

Ala Ser Ile Ala Arg Asn Phe Pro Asp Asn Gly Cys Ile Ser Cys Met
             420                 425                 430
```

```
Cys His Asn Thr Asp Gly Ile Tyr Ser Thr Lys Gln Thr Ala Val Val
            435                 440                 445

Arg Ala Ser Asp Asp Phe Tyr Pro Arg Asp Pro Ala Ser His Thr Ile
450                 455                 460

His Ile Ser Ser Val Ala Tyr Asn Ser Leu Phe Leu Gly Glu Phe Met
465                 470                 475                 480

Gln Pro Asp Trp Asp Met Phe His Ser Leu His Pro Ala Ala Asp Tyr
                485                 490                 495

His Ala Ala Arg Ala Val Gly Gly Cys Pro Ile Tyr Val Ser Asp
            500                 505                 510

Lys Pro Gly Phe His Asn Phe Glu Leu Leu Lys Lys Leu Val Leu Pro
            515                 520                 525

Asp Gly Ser Val Leu Arg Ala Arg Leu Pro Gly Arg Pro Thr Arg Asp
    530                 535                 540

Cys Leu Phe Asn Asp Pro Ala Arg Asp Gly Thr Ser Leu Leu Lys Ile
545                 550                 555                 560

Trp Asn Lys Asn Cys Ser Gly Val Val Gly Val Phe Asn Cys Gln
                565                 570                 575

Gly Ala Gly Trp Cys Lys Ile Glu Lys Lys Ile Arg Ile His Asp Thr
            580                 585                 590

Ser Pro Gly Thr Leu Thr Gly Ser Val Arg Ala Thr Asp Val Asp Ser
    595                 600                 605

Ile Ala Glu Val Ala Gly Gln Gly Trp Asn Gly Asp Val Val Val Tyr
            610                 615                 620

Leu Tyr Arg Ala Gly Glu Leu Val Cys Leu Pro Lys Gly Ala Ser Leu
625                 630                 635                 640

Pro Val Thr Leu Lys Val Arg Glu Tyr Glu Leu Phe His Phe Cys Pro
                645                 650                 655

Ile Lys Glu Ile Thr Ser Asn Ile Ser Phe Ala Pro Ile Gly Leu Leu
            660                 665                 670

Asp Met Phe Asn Gly Ser Gly Ala Val Asp Gln Phe Asp Val Gln Leu
            675                 680                 685

Thr Ser Glu Asn Arg Thr Glu Leu Ser Asp Gly Glu Lys Arg Ser Pro
690                 695                 700

Ser Ala Ser Ile Gln Leu Lys Val Arg Gly Cys Gly Arg Phe Gly Ala
705                 710                 715                 720

Tyr Ser Ser Gln Cys Pro Leu Lys Cys Thr Val Gly Gly Ala Asp Ser
                725                 730                 735

Gly Phe Asn Tyr Asp Glu Glu Thr Cys Leu Leu Thr Leu Thr Leu Pro
            740                 745                 750

Val Pro Gln Glu Glu Met Tyr Arg Trp Pro Val Glu Ile Gln Val
            755                 760                 765

<210> SEQ ID NO 7
<211> LENGTH: 772
<212> TYPE: PRT
<213> ORGANISM: Cucumis sativus

<400> SEQUENCE: 7

Met Thr Val Thr Pro Lys Ile Thr Val Asn Asp Gly Asn Leu Val Val
1               5                   10                  15

His Gly Lys Thr Ile Leu Thr Gly Val Pro Asp Asn Ile Val Leu Thr
                20                  25                  30

Pro Gly Ser Gly Leu Gly Leu Val Ala Gly Ala Phe Ile Gly Ala Thr
            35                  40                  45
```

```
Ala Ser Asn Ser Lys Ser Leu His Val Phe Pro Val Gly Val Leu Glu
    50                  55                  60

Gly Thr Arg Phe Leu Cys Cys Phe Arg Phe Lys Leu Trp Trp Met Thr
 65                  70                  75                  80

Gln Arg Met Gly Thr Ser Gly Arg Asp Ile Pro Phe Glu Thr Gln Phe
                    85                  90                  95

Leu Leu Met Glu Ser Gln Gly Asn Asp Gly Glu Asp Pro Asp Asn Ser
                100                 105                 110

Ser Thr Ile Tyr Thr Val Phe Leu Pro Leu Leu Glu Gly Gln Phe Arg
            115                 120                 125

Ala Ala Leu Gln Gly Asn Glu Lys Asn Glu Met Glu Ile Cys Leu Glu
    130                 135                 140

Ser Gly Asp Asn Thr Val Glu Thr Asn Gln Gly Leu Ser Leu Val Tyr
145                 150                 155                 160

Met His Ala Gly Thr Asn Pro Phe Glu Val Ile Thr Gln Ala Val Lys
                    165                 170                 175

Ala Val Glu Lys His Thr Gln Thr Phe Leu His Arg Glu Lys Lys Lys
                180                 185                 190

Leu Pro Ser Phe Leu Asp Trp Phe Gly Trp Cys Thr Trp Asp Ala Phe
            195                 200                 205

Tyr Thr Asp Val Thr Ala Glu Gly Val Val Glu Gly Leu Gln Ser Leu
    210                 215                 220

Ser Asp Gly Gly Ala Pro Pro Lys Phe Leu Ile Ile Asp Asp Gly Trp
225                 230                 235                 240

Gln Gln Ile Glu Ala Lys Pro Lys Asp Ala Asp Cys Val Val Gln Glu
                    245                 250                 255

Gly Ala Gln Phe Ala Ser Arg Leu Ser Gly Ile Lys Glu Asn His Lys
                260                 265                 270

Phe Gln Lys Asn Gly Asn Asn Tyr Asp Gln Val Pro Gly Leu Lys Val
            275                 280                 285

Val Val Asp Asp Ala Lys Lys Gln His Lys Val Lys Phe Val Tyr Ala
    290                 295                 300

Trp His Ala Leu Ala Gly Tyr Trp Gly Gly Val Lys Pro Ala Ser Pro
305                 310                 315                 320

Gly Met Glu His Tyr Asp Ser Ala Leu Ala Tyr Pro Val Gln Ser Pro
                    325                 330                 335

Gly Met Leu Gly Asn Gln Pro Asp Ile Val Val Asp Ser Leu Ala Val
                340                 345                 350

His Gly Ile Gly Leu Val His Pro Lys Lys Val Phe Asn Phe Tyr Asn
            355                 360                 365

Glu Leu His Ser Tyr Leu Ala Ser Cys Gly Ile Asp Gly Val Lys Val
    370                 375                 380

Asp Val Gln Asn Ile Ile Glu Thr Leu Gly Ala Gly His Gly Gly Arg
385                 390                 395                 400

Val Thr Leu Thr Arg Ser Tyr His Gln Ala Leu Glu Ala Ser Ile Ala
                    405                 410                 415

Arg Asn Phe Ser Asp Asn Gly Cys Ile Ala Cys Met Cys His Asn Thr
                420                 425                 430

Asp Ser Leu Tyr Ser Ala Lys Gln Thr Ala Val Val Arg Ala Ser Asp
            435                 440                 445

Asp Tyr Tyr Pro Arg Asp Pro Ala Ser His Thr Ile His Ile Ser Ser
    450                 455                 460
```

Val Ala Tyr Asn Ser Leu Phe Leu Gly Glu Phe Met Gln Pro Asp Trp
465                 470                 475                 480

Asp Met Phe His Ser Leu His Pro Thr Ala Glu Tyr His Gly Ala Ala
            485                 490                 495

Arg Ala Ile Gly Gly Cys Ala Ile Tyr Val Ser Asp Lys Pro Gly Asn
        500                 505                 510

His Asn Phe Asp Leu Leu Lys Lys Leu Val Leu Pro Asp Gly Ser Val
    515                 520                 525

Leu Arg Ala Gln Leu Pro Gly Arg Pro Thr Arg Asp Ser Leu Phe Asn
530                 535                 540

Asp Pro Ala Arg Asp Gly Thr Ser Leu Leu Lys Ile Trp Asn Met Asn
545                 550                 555                 560

Lys Cys Ser Gly Val Val Gly Val Phe Asn Cys Gln Gly Ala Gly Trp
                565                 570                 575

Cys Arg Ile Thr Lys Lys Thr Arg Ile His Asp Glu Ser Pro Gly Thr
            580                 585                 590

Leu Thr Thr Ser Val Arg Ala Ala Asp Val Asp Ala Ile Ser Gln Val
        595                 600                 605

Ala Gly Ala Asp Trp Lys Gly Asp Thr Ile Val Tyr Ala Tyr Arg Ser
    610                 615                 620

Gly Asp Leu Thr Arg Leu Pro Lys Gly Ala Ser Val Pro Val Thr Leu
625                 630                 635                 640

Lys Val Leu Glu Tyr Asp Leu Phe His Ile Ser Pro Leu Lys Asp Ile
                645                 650                 655

Thr Ser Asn Ile Ser Phe Ala Pro Ile Gly Leu Val Asp Met Phe Asn
            660                 665                 670

Ile Gly Gly Ala Val Glu Gln Val Asp Ile Gln Val Glu Pro Ile
        675                 680                 685

Pro Glu Phe Asp Gly Glu Val Ala Ser Glu Leu Thr Cys Ser Leu Pro
    690                 695                 700

Asp Asp Arg Pro Pro Thr Ala Thr Ile Thr Met Lys Ala Arg Gly Cys
705                 710                 715                 720

Gly Arg Phe Gly Leu Tyr Ser Ser Gln Arg Pro Leu Lys Cys Ser Val
                725                 730                 735

Asp Lys Val Gly Thr Asp Phe Val Tyr Asp Asp Val Thr Gly Leu Val
            740                 745                 750

Thr Phe Glu Ile Pro Ile Pro Thr Glu Met Tyr Arg Trp Asn Ile
        755                 760                 765

Glu Ile Glu Val
    770

<210> SEQ ID NO 8
<211> LENGTH: 211
<212> TYPE: PRT
<213> ORGANISM: Zea mays

<400> SEQUENCE: 8

Pro Phe Glu Val Ile Thr Ser Ser Val Lys Ala Val Glu Arg His Leu
1               5                   10                  15

Gln Thr Phe Ser His Arg Glu Lys Lys Lys Met Pro Asp Ile Leu Asn
            20                  25                  30

Trp Phe Gly Trp Cys Thr Trp Asp Ala Phe Tyr Thr Asn Val Thr Ala
        35                  40                  45

Gln Gly Val Lys Gln Gly Leu Gln Ser Leu Glu Lys Gly Gly Val Ser
    50                  55                  60

```
Pro Arg Phe Val Ile Ile Asp Asp Gly Trp Gln Ser Val Ala Met Asp
 65                  70                  75                  80

Pro Val Gly Ile Ala Cys Leu Ser Asp Asn Ser Ala Asn Phe Ala Asn
                 85                  90                  95

Arg Leu Thr His Ile Arg Glu Asn His Lys Phe Gln Lys Asn Gly Arg
            100                 105                 110

Glu Gly His Arg Glu Asp Pro Ala Lys Gly Leu Ala His Val Val
            115                 120                 125

Asn Glu Ile Lys Gly Lys His Gln Leu Lys Tyr Val Tyr Val Trp His
130                 135                 140

Ala Ile Thr Gly Tyr Trp Gly Gly Val Arg Pro Gly Ala Ala Gly Met
145                 150                 155                 160

Glu His Tyr Gly Ser Lys Met Gln Arg Pro Val Pro Ser Pro Gly Val
                165                 170                 175

Pro Lys Asn Glu Arg Cys Glu Ala Leu Asp Ser Met Thr Ala Asn Gly
            180                 185                 190

Leu Gly Leu Val Asn Leu Asp Arg Ala Phe Ser Phe Tyr Asp Glu Leu
            195                 200                 205

His Ser Tyr
    210

<210> SEQ ID NO 9
<211> LENGTH: 747
<212> TYPE: PRT
<213> ORGANISM: Zea mays

<400> SEQUENCE: 9

Met Thr Val Ala Ser Ser Val Arg Leu Ala Gly Gly Asn Leu Thr Val
 1               5                  10                  15

Cys Gly Arg Thr Val Leu Ser Gly Val Pro Asp Ala Val Val Ala Thr
                20                  25                  30

Ser Ala Ala Thr Glu Gly Ala Val Asp Gly Ile Phe Leu Gly Ala Asp
            35                  40                  45

Phe Ala Glu Pro Ala Ala Arg His Val Val Ser Leu Gly Asp Leu Arg
 50                  55                  60

Asp Val Arg Phe Met Ala Cys Phe Arg Phe Lys Leu Trp Trp Met Ala
 65                  70                  75                  80

Gln Arg Met Gly Glu Lys Gly Ser Asp Val Pro Arg Glu Thr Gln Phe
                 85                  90                  95

Leu Leu Val Glu Ser Arg Gly Val Gly Asp Glu Asp Ala Ala Tyr Val
            100                 105                 110

Val Phe Leu Pro Leu Val Glu Gly Ala Phe Arg Ala Ser Ile Gln Gly
            115                 120                 125

Gly Ala Gly Asp Ala Leu Glu Leu Cys Val Glu Ser Gly Asp Asp
130                 135                 140

Thr Arg Ala Ala Ser Phe Glu Arg Ser Leu Phe Val Gly Ala Ala Glu
145                 150                 155                 160

Ser Asp Pro Phe Ala Ala Ile Ser Gly Ala Val Ala Ala Lys Ser
                165                 170                 175

Ala Leu Arg Thr Phe Arg Val Arg Ala Glu Lys Lys Leu Pro Gly Ile
            180                 185                 190

Val Asp Tyr Phe Gly Trp Cys Thr Trp Asp Ala Phe Tyr Gln Asp Val
            195                 200                 205

Thr Gln Glu Gly Val Glu Ala Gly Leu Arg Ser Leu Ile Ala Gly Gly
```

```
                 210                 215                 220
Ala Pro Pro Lys Phe Val Ile Ile Asp Asp Gly Trp Gln Ser Val Ala
225                 230                 235                 240

Thr Asp Thr Asn Glu Ser Ala Gly Glu Asp Lys Pro Pro Leu Leu Ser
                245                 250                 255

Arg Leu Thr Gly Ile Lys Glu Asn Ser Lys Phe Gln Asn Ala Asp Asp
                260                 265                 270

Pro Ala Ala Gly Ile Lys Thr Val Val Arg Leu Ala Lys Glu Glu Tyr
            275                 280                 285

Arg Leu Lys Tyr Val Tyr Val Trp His Ala Ile Thr Gly Tyr Trp Gly
290                 295                 300

Gly Val Arg Pro Gly Glu Glu His Tyr Arg Ser Ser Met Gln Phe Pro
305                 310                 315                 320

Lys Val Ser Pro Gly Val Met Glu Asn Glu Pro Gly Met Lys Thr Asp
                325                 330                 335

Val Leu Thr Val Gln Gly Leu Gly Leu Val His Pro Arg Ala Val Tyr
                340                 345                 350

Arg Phe Tyr Asp Glu Leu His Ala Tyr Leu Ala Ala Ala Gly Val Asp
            355                 360                 365

Gly Val Lys Val Asp Val Gln Cys Ile Leu Glu Thr Leu Gly Ala Gly
            370                 375                 380

His Gly Gly Arg Val Gln Leu Thr Arg Gln Tyr His Gln Ala Leu Asp
385                 390                 395                 400

Ala Ser Val Ala Lys Asn Phe Pro Glu Asn Gly Ile Ile Ala Cys Met
                405                 410                 415

Ser His Asn Thr Asp Ala Leu Tyr Cys Ser Lys Gln Thr Ala Val Val
                420                 425                 430

Arg Ala Ser Asp Asp Phe Cys Pro Arg Asp Pro Ala Ser His Thr Ile
            435                 440                 445

His Ile Ala Ser Val Ala Tyr Asn Ser Val Phe Leu Gly Glu Phe Met
450                 455                 460

Leu Pro Asp Trp Asp Met Phe His Ser Leu His Gln Ala Gly Asp Tyr
465                 470                 475                 480

His Gly Ser Ala Arg Ala Ile Ser Gly Gly Pro Val Tyr Val Ser Asp
                485                 490                 495

Ala Pro Gly Lys His Asn Phe Glu Leu Leu Lys Lys Ile Val Leu Pro
                500                 505                 510

Asp Gly Ser Ile Leu Arg Ala Arg Leu Pro Gly Arg Pro Thr Lys Asp
            515                 520                 525

Cys Leu Phe Thr Asp Pro Ala Arg Asp Gly Val Ser Leu Leu Lys Ile
530                 535                 540

Trp Asn Met Asn Lys Phe Thr Gly Val Leu Gly Val Tyr Asn Cys Gln
545                 550                 555                 560

Gly Ala Ala Trp Asn Ser Val Glu Lys Lys Asn Thr Phe His Gln Thr
                565                 570                 575

Gly Thr Glu Ala Leu Thr Cys Gly Val Lys Gly Gly Asp Val His Leu
                580                 585                 590

Ile Ser Glu Ala Ala Thr Asp Thr Glu Trp Asp Gly Asp Cys Ala Met
            595                 600                 605

Tyr Arg His Ala Asp Gly Asp Leu Val Val Leu Pro His Asp Ala Ala
            610                 615                 620

Leu Pro Val Ser Leu Lys Val Leu Glu His Asp Ile Leu Thr Val Ser
625                 630                 635                 640
```

```
Pro Ile Lys Glu Leu Ala Pro Gly Phe Arg Phe Ala Pro Ile Gly Leu
                645                 650                 655

Val Asp Met Phe Asn Ser Gly Gly Ala Val Glu Gly Leu Thr Tyr His
            660                 665                 670

Leu Leu Gly Gly Asp Gly Ser Thr Leu Gly Ser Glu Ala Val Ala Leu
        675                 680                 685

Ala Cys Met Glu Val Lys Gly Cys Gly Arg Phe Gly Ala Tyr Ser Ser
    690                 695                 700

Val Arg Pro Arg Lys Ser Thr Leu Gly Ser Ala Gln Ile Glu Leu Lys
705                 710                 715                 720

Tyr Asp Ser Ser Ser Gly Leu Leu Ile Leu Gln Leu Asp Ala Met Pro
                725                 730                 735

Lys Glu Arg Val His Lys Ile Val Ile Glu Leu
                740                 745

<210> SEQ ID NO 10
<211> LENGTH: 753
<212> TYPE: PRT
<213> ORGANISM: Oryza sativa

<400> SEQUENCE: 10

Met Thr Val Gly Ala Gly Val Ala Val Gln Asp Gly Gly Leu Val Ala
1               5                   10                  15

Leu Gly Ala Thr Val Leu Thr Glu Val Arg Asp Asn Val Leu Leu Thr
            20                  25                  30

Pro Ala Ala Gly Ala Gly Met Thr Ser Gly Thr Phe Gly Val Arg
        35                  40                  45

Ser Ala Thr Ala Gly Ser Arg Ser Val Phe Pro Val Gly Lys Leu Arg
    50                  55                  60

Gly Leu Arg Phe Ile Cys Thr Phe Arg Phe Lys Met Trp Trp Met Thr
65              70                  75                  80

Gln Arg Met Gly Thr Ser Gly Arg Asp Ile Pro Phe Glu Thr Gln Phe
                85                  90                  95

Leu Leu Val Glu Ala Ala Asp Ala Asp Gly Ser His Leu Ala Gly Asp
            100                 105                 110

Gly Ala Ala Val Tyr Thr Val Phe Leu Pro Ile Leu Glu Gly Pro
        115                 120                 125

Phe Arg Ala Val Leu Gln Gly Asn Ser Asp Asp Glu Leu Glu Ile Cys
    130                 135                 140

Leu Glu Ser Gly Asp Pro Ala Val Glu Ser Phe Glu Gly Thr His Leu
145                 150                 155                 160

Val Phe Val Gly Ala Gly Ser Asp Pro Phe Glu Val Ile Thr Asn Ser
                165                 170                 175

Val Lys Ala Val Glu Arg His Leu Gln Thr Phe Thr His Arg Glu Lys
            180                 185                 190

Lys Lys Met Pro Asp Met Leu Asn Trp Phe Gly Trp Cys Thr Trp Asp
        195                 200                 205

Ala Phe Tyr Thr Asp Val Thr Ser Glu Gly Val Met Glu Gly Leu Gln
    210                 215                 220

Ser Leu Gly Lys Gly Gly Thr Gly Pro Lys Phe Val Ile Ile Asp Asp
225                 230                 235                 240

Gly Trp Gln Ser Val Ser Met Asp Pro Ala Gly Ile Ala Ser Leu Ala
                245                 250                 255

Asp Asn Ser Ala Asn Phe Ala Asn Arg Leu Thr His Ile Lys Glu Asn
```

-continued

```
                260                 265                 270
His Lys Phe Gln Leu Asn Gly Arg Lys Gly His Arg Glu Glu Asn Pro
            275                 280                 285

Ala Asn Gly Leu Ala His Ile Val Asn Glu Ile Lys Gly Lys His Gln
        290                 295                 300

Leu Lys Tyr Val Tyr Val Trp His Ala Ile Thr Gly Tyr Trp Gly Gly
305                 310                 315                 320

Val Arg Pro Gly Ala Asp Gly Met Glu His Tyr Glu Ser Lys Met Gln
                325                 330                 335

Tyr Pro Val Ser Ser Pro Gly Val Gln Lys Asn Glu Pro Cys Asp Ala
            340                 345                 350

Leu Asn Ser Ile Thr Thr Asn Gly Leu Gly Leu Val Asn Pro Asp Arg
        355                 360                 365

Val Phe Ser Phe Tyr Asn Glu Leu His Ala Tyr Leu Ala Ser Ala Gly
    370                 375                 380

Ile Asp Gly Val Lys Val Asp Val Gln Asn Ile Leu Glu Thr Leu Gly
385                 390                 395                 400

Ala Gly His Gly Gly Arg Val Leu Leu Ala Arg Lys Tyr His Gln Ala
                405                 410                 415

Leu Glu Ala Ser Ile Ala Arg Asn Phe Arg Asp Asn Gly Ile Ile Cys
            420                 425                 430

Cys Met Ser His Asn Thr Asp Asn Leu Tyr Ser Ser Lys Arg Ser Ala
        435                 440                 445

Val Val Arg Ala Ser Asp Asp Phe Trp Pro Arg Asp Pro Ala Ser His
    450                 455                 460

Thr Ile His Ile Ala Ser Val Ala Tyr Asn Thr Val Phe Leu Gly Glu
465                 470                 475                 480

Phe Met Gln Pro Asp Trp Asp Met Phe His Ser Val His Pro Met Ala
                485                 490                 495

Glu Tyr His Ala Ala Arg Ala Val Gly Gly Cys Ala Ile Tyr Val
            500                 505                 510

Ser Asp Lys Pro Gly Asn His Asp Phe Asn Leu Leu Lys Lys Leu Val
        515                 520                 525

Leu Pro Asp Gly Ser Ile Leu Arg Ala Lys Leu Pro Gly Arg Pro Thr
    530                 535                 540

Arg Asp Cys Leu Phe Ser Asp Pro Ala Arg Asp Gly Lys Ser Ile Leu
545                 550                 555                 560

Lys Ile Trp Asn Leu Asn Glu His Ser Gly Val Ile Gly Ala Phe Asn
                565                 570                 575

Cys Gln Gly Ala Gly Trp Cys Arg Val Gly Lys Lys Asn Leu Val His
            580                 585                 590

Asp Glu Gln Pro Ala Thr Val Thr Gly Val Ile Arg Ala Gln Asp Val
        595                 600                 605

His His Leu Ala Thr Val Ala Ala Asp Gly Trp Asn Gly Asp Val Ile
    610                 615                 620

Val Tyr Ser His Ile Gly Gly Glu Val Thr Cys Leu Pro Lys Asn Ala
625                 630                 635                 640

Ser Leu Pro Val Thr Leu Lys Thr Arg Glu Tyr Glu Val Phe Thr Val
                645                 650                 655

Val Pro Leu Lys Lys Leu Asp Asn Gly Val Ser Phe Ala Ala Val Gly
            660                 665                 670

Leu Ile Gly Met Phe Asn Ser Gly Gly Ala Val Thr Ala Val Arg Tyr
        675                 680                 685
```

```
Val Glu Asp Ala Gly Val Glu Val Arg Val Arg Gly Ser Gly Thr Val
        690             695             700
Gly Ala Tyr Ser Ser Ala Lys Pro Ala Arg Val Val Asp Ser Glu
705             710             715             720
Ala Ala Glu Phe Ser Tyr Asp Asp Gly Cys Gly Leu Val Thr Phe Glu
            725             730             735
Leu Ala Val Pro Glu Gln Glu Leu Tyr Ser Trp Thr Ile Ser Ile Glu
            740             745             750
Tyr

<210> SEQ ID NO 11
<211> LENGTH: 777
<212> TYPE: PRT
<213> ORGANISM: Pisum sativum

<400> SEQUENCE: 11

Met Thr Val Thr Pro Lys Ile Ser Val Asn Asp Gly Asn Leu Val Val
1               5                   10                  15
His Gly Lys Thr Ile Leu Lys Gly Val Pro Glu Asn Val Val Leu Thr
            20                  25                  30
Pro Gly Ser Gly Asn Gly Leu Leu Thr Gly Gly Ala Phe Ile Gly Ala
        35                  40                  45
Thr Ala Ser Asn Ser Lys Ser Leu His Val Phe Pro Ile Gly Ile Leu
    50                  55                  60
Glu Gly Leu Arg Phe Val Cys Cys Phe Arg Phe Lys Leu Trp Trp Met
65                  70                  75                  80
Thr Gln Arg Met Gly Thr Cys Gly Arg Asp Ile Pro Leu Glu Thr Gln
                85                  90                  95
Phe Met Leu Ile Glu Ser Lys Asp Ser Glu Gly Glu Glu Gly Asn Ser
            100                 105                 110
Pro Val Ile Tyr Thr Val Leu Leu Pro Leu Leu Glu Gly Pro Phe Arg
        115                 120                 125
Ser Val Leu Gln Gly Asn Glu Lys Ser Glu Ile Glu Ile Cys Phe Glu
    130                 135                 140
Ser Gly Asp His Ala Val Glu Thr Asn Gln Gly Leu His Met Val Tyr
145                 150                 155                 160
Met His Ala Gly Thr Asn Pro Phe Glu Val Ile Asn Gln Ala Val Lys
                165                 170                 175
Ala Val Glu Lys His Met Gln Thr Phe His His Arg Glu Lys Lys Arg
            180                 185                 190
Leu Pro Ser Phe Leu Asp Met Phe Gly Trp Cys Thr Trp Asp Ala Phe
        195                 200                 205
Tyr Thr Asp Val Thr Ala Glu Gly Val Glu Gln Gly Leu Lys Ser Leu
    210                 215                 220
Ser Glu Gly Gly Thr Pro Pro Arg Phe Leu Ile Ile Asp Asp Gly Trp
225                 230                 235                 240
Gln Gln Ile Glu Ser Lys Ala Lys Asp Pro Gly Cys Val Val Gln Glu
                245                 250                 255
Gly Ala Gln Phe Ala Thr Met Leu Thr Gly Ile Lys Glu Asn Ala Lys
            260                 265                 270
Phe Gln Lys Asn Lys Asn Glu Glu His Ser Glu Pro Thr Ser Gly Leu
        275                 280                 285
Lys His Leu Val Asp Gly Val Lys Lys His His Asn Val Lys Asn Val
    290                 295                 300
```

```
Tyr Val Trp His Ala Leu Ala Gly Tyr Trp Gly Val Lys Pro Ala
305                 310                 315                 320

Ala Thr Gly Met Glu His Tyr Asp Thr Ala Leu Ala Tyr Pro Val Gln
                325                 330                 335

Ser Pro Gly Val Leu Gly Asn Gln Pro Asp Ile Val Met Asp Ser Leu
            340                 345                 350

Ser Val His Gly Leu Gly Leu Val His Pro Lys Lys Val Phe Asn Phe
        355                 360                 365

Tyr Asn Glu Leu His Ala Tyr Leu Ala Ser Cys Gly Val Asp Gly Val
    370                 375                 380

Lys Val Asp Val Gln Asn Ile Ile Glu Thr Leu Gly Ala Gly His Gly
385                 390                 395                 400

Gly Arg Val Ser Leu Thr Arg Ser Tyr His His Ala Leu Glu Ala Ser
                405                 410                 415

Ile Ala Arg Asn Phe Ser Asp Asn Gly Cys Ile Ala Cys Met Cys His
            420                 425                 430

Asn Thr Asp Gly Leu Tyr Ser Ala Lys Gln Thr Ala Val Val Arg Ala
        435                 440                 445

Ser Asp Asp Phe Tyr Pro Arg Asp Pro Ala Ser His Thr Ile His Ile
    450                 455                 460

Ser Ser Val Ala Tyr Asn Ser Leu Phe Leu Gly Glu Phe Met Gln Pro
465                 470                 475                 480

Asp Trp Asp Met Phe His Ser Leu His Pro Ala Ala Glu Tyr His Ala
                485                 490                 495

Ala Ala Arg Ala Ile Gly Gly Cys Pro Ile Tyr Val Ser Asp Lys Pro
            500                 505                 510

Gly Asn His Asn Phe Asp Leu Leu Lys Lys Leu Val Leu Ser Asp Gly
        515                 520                 525

Ser Val Leu Arg Ala Gln Leu Pro Gly Arg Pro Thr Arg Asp Ser Leu
    530                 535                 540

Phe Val Asp Pro Ala Arg Asp Arg Thr Ser Leu Leu Lys Ile Trp Asn
545                 550                 555                 560

Met Asn Lys Cys Thr Gly Val Val Gly Val Phe Asn Cys Gln Gly Ala
                565                 570                 575

Gly Trp Cys Lys Val Glu Lys Lys Thr Arg Ile His Asp Ile Ser Pro
            580                 585                 590

Gly Thr Leu Thr Ser Ser Val Cys Ala Ser Asp Val Asp Leu Ile Thr
        595                 600                 605

Gln Val Ala Gly Ala Glu Trp His Gly Glu Thr Ile Val Tyr Ala Tyr
    610                 615                 620

Arg Ser Gly Glu Val Ile Arg Leu Pro Lys Gly Val Ser Ile Pro Val
625                 630                 635                 640

Thr Leu Lys Val Leu Glu Phe Glu Leu Phe His Phe Cys Pro Ile Gln
                645                 650                 655

Glu Ile Ser Ser Ser Ile Ser Phe Ala Thr Ile Gly Leu Met Asp Met
            660                 665                 670

Phe Asn Thr Gly Gly Ala Val Glu Glu Val Glu Ile His Arg Glu Thr
        675                 680                 685

Asp Asn Lys Gln Glu Leu Phe Glu Gly Glu Ala Val Ser Ser Glu Leu
    690                 695                 700

Ile Thr Ser Leu Gly Pro Asn Arg Thr Thr Ala Thr Ile Thr Leu
705                 710                 715                 720
```

```
Lys Val Arg Gly Ser Gly Lys Phe Gly Val Tyr Ser Ser Gln Arg Pro
                725                 730                 735

Ile Lys Cys Met Val Asp Gly Thr Glu Thr Asp Phe Asn Tyr Asp Ser
            740                 745                 750

Glu Thr Gly Leu Thr Thr Phe Ile Ile Pro Val Pro Gln Glu Glu Leu
        755                 760                 765

Tyr Lys Trp Leu Ile Glu Ile Gln Val
770                 775

<210> SEQ ID NO 12
<211> LENGTH: 753
<212> TYPE: PRT
<213> ORGANISM: Cucumis sativus

<400> SEQUENCE: 12

Met Thr Val Gly Ala Gly Ile Thr Ile Ser Asp Ala Asn Leu Thr Val
1               5                   10                  15

Leu Gly Asn Arg Val Leu Ser Asp Val His Asn Asn Ile Thr Leu Thr
            20                  25                  30

Ala Ala Pro Gly Gly Gly Val Met Asn Gly Ala Phe Ile Gly Val Gln
        35                  40                  45

Ser Asp Gln Ile Gly Ser Arg Arg Val Phe Pro Ile Gly Lys Leu Ile
    50                  55                  60

Gly Leu Arg Phe Leu Cys Ala Phe Arg Phe Lys Leu Trp Trp Met Thr
65                  70                  75                  80

Gln Arg Met Gly Cys Ser Gly Gln Glu Ile Pro Phe Glu Thr Gln Phe
                85                  90                  95

Leu Val Val Glu Thr Arg Asp Gly Ser Asn Ile Ala Gly Asn Gly Glu
            100                 105                 110

Glu Gly Asp Ala Val Tyr Thr Val Phe Leu Pro Ile Leu Glu Gly Asp
        115                 120                 125

Phe Arg Ala Val Leu Gln Gly Asn Asp Asn Asn Glu Leu Glu Ile Cys
    130                 135                 140

Leu Glu Ser Gly Asp Pro Ser Val Asp Gly Phe Glu Gly Ser His Leu
145                 150                 155                 160

Val Phe Val Gly Ala Gly Ser Asp Pro Phe Glu Thr Ile Thr Tyr Ala
                165                 170                 175

Val Lys Ser Val Glu Lys His Leu Gln Thr Phe Ala His Arg Glu Arg
            180                 185                 190

Lys Lys Met Pro Asp Ile Leu Asn Trp Phe Gly Trp Cys Thr Trp Asp
        195                 200                 205

Ala Phe Tyr Thr Asp Val Thr Ser Asp Gly Val Lys Lys Gly Leu Glu
    210                 215                 220

Ser Phe Glu Asn Gly Gly Ile Pro Pro Lys Phe Val Ile Ile Asp Asp
225                 230                 235                 240

Gly Trp Gln Ser Val Ala Lys Asp Ala Ala Ser Thr Asp Cys Lys Ala
                245                 250                 255

Asp Asn Thr Ala Asn Phe Ala Asn Arg Leu Thr His Ile Lys Glu Asn
            260                 265                 270

Tyr Lys Phe Gln Lys Asp Gly Lys Glu Gly Glu Arg Ile Glu Asn Pro
        275                 280                 285

Ala Leu Gly Leu Gln His Ile Val Ser Tyr Met Lys Glu Lys His Ala
    290                 295                 300

Thr Lys Tyr Val Tyr Val Trp His Ala Ile Thr Gly Tyr Trp Gly Gly
305                 310                 315                 320
```

-continued

```
Val Ser Ser Gly Val Lys Glu Met Glu Gln Tyr Glu Ser Lys Ile Ala
            325                 330                 335

Tyr Pro Val Ala Ser Pro Gly Val Glu Ser Asn Glu Pro Cys Asp Ala
            340                 345                 350

Leu Asn Ser Ile Ser Lys Thr Gly Leu Gly Leu Val Asn Pro Glu Lys
            355                 360                 365

Val Phe Asn Phe Tyr Asn Glu Gln His Ser Tyr Leu Ala Ser Ala Gly
            370                 375                 380

Val Asp Gly Val Lys Val Asp Val Gln Asn Ile Leu Glu Thr Leu Gly
385                 390                 395                 400

Ala Gly His Gly Gly Arg Val Lys Leu Ala Arg Lys Tyr His Gln Ala
            405                 410                 415

Leu Glu Ala Ser Ile Ser Arg Asn Phe Gln Asp Asn Gly Ile Ile Ser
            420                 425                 430

Cys Met Ser His Asn Thr Asp Gly Leu Tyr Ser Ser Lys Arg Asn Ala
            435                 440                 445

Val Ile Arg Ala Ser Asp Asp Phe Trp Pro Arg Asp Pro Ala Ser His
        450                 455                 460

Thr Ile His Ile Ala Ser Val Ala Tyr Asn Ser Leu Phe Leu Gly Glu
465                 470                 475                 480

Phe Met Gln Pro Asp Trp Asp Met Phe His Ser Leu His Pro Met Ala
            485                 490                 495

Glu Tyr His Gly Ala Ala Arg Ala Val Gly Gly Cys Ala Ile Tyr Val
            500                 505                 510

Ser Asp Lys Pro Gly Gln His Asp Phe Asn Leu Leu Lys Leu Val
            515                 520                 525

Leu His Asp Gly Ser Ile Leu Arg Ala Lys Leu Pro Gly Arg Pro Thr
            530                 535                 540

Lys Asp Cys Leu Phe Ala Asp Pro Ala Arg Asp Gly Lys Ser Leu Leu
545                 550                 555                 560

Lys Ile Trp Asn Met Asn Asp Leu Ser Gly Val Gly Val Phe Asn
            565                 570                 575

Cys Gln Gly Ala Gly Trp Cys Lys Val Gly Lys Asn Leu Ile His
            580                 585                 590

Asp Glu Asn Pro Asp Thr Ile Thr Gly Val Ile Arg Ala Lys Asp Val
            595                 600                 605

Ser Tyr Leu Trp Lys Ile Ala Gly Glu Ser Trp Thr Gly Asp Ala Val
            610                 615                 620

Ile Phe Ser His Leu Ala Gly Glu Val Val Tyr Leu Pro Gln Asp Ala
625                 630                 635                 640

Ser Met Pro Ile Thr Leu Lys Ser Arg Glu Phe Asp Val Phe Thr Val
            645                 650                 655

Val Pro Val Lys Glu Leu Ala Asn Asp Ile Lys Phe Ala Pro Ile Gly
            660                 665                 670

Leu Met Lys Met Phe Asn Ser Gly Ala Val Lys Glu Met Asn His
            675                 680                 685

Gln Pro Gly Ser Ser Asn Val Ser Leu Lys Val Arg Gly Ser Gly Pro
            690                 695                 700

Phe Gly Ala Tyr Ser Ser Lys Pro Lys Arg Val Ala Val Asp Ser
705                 710                 715                 720

Glu Glu Val Glu Phe Ile Tyr Asp Glu Gly Gly Leu Ile Thr Ile Asp
            725                 730                 735
```

Leu Lys Val Pro Glu Lys Glu Leu Tyr Leu Trp Asp Ile Arg Ile Glu
            740                 745                 750

Leu

<210> SEQ ID NO 13
<211> LENGTH: 772
<212> TYPE: PRT
<213> ORGANISM: Cucumis melo

<400> SEQUENCE: 13

Met Thr Val Thr Pro Lys Ile Ser Val Asn Asp Gly Asn Leu Val Val
1               5                   10                  15

His Gly Lys Thr Ile Leu Thr Gly Val Pro Asp Asn Ile Val Leu Thr
            20                  25                  30

Pro Gly Ser Gly Leu Gly Leu Val Ala Gly Ala Phe Ile Gly Ala Thr
        35                  40                  45

Ala Ser Asn Ser Lys Ser Leu His Val Phe Pro Val Gly Val Leu Glu
    50                  55                  60

Gly Thr Arg Phe Leu Cys Cys Phe Arg Phe Lys Leu Trp Trp Met Thr
65                  70                  75                  80

Gln Arg Met Gly Thr Ser Gly Arg Asp Ile Pro Phe Glu Thr Gln Phe
                85                  90                  95

Leu Leu Met Glu Ser Lys Gly Asn Asp Gly Glu Asp Pro Asp Asn Ser
            100                 105                 110

Ser Thr Ile Tyr Thr Val Phe Leu Pro Leu Leu Glu Gly Gln Phe Arg
        115                 120                 125

Ala Ala Leu Gln Gly Asn Glu Lys Asn Glu Met Glu Ile Cys Leu Glu
    130                 135                 140

Ser Gly Asp Asn Thr Val Glu Thr Asn Gln Gly Leu Ser Leu Val Tyr
145                 150                 155                 160

Met His Ala Gly Thr Asn Pro Phe Glu Val Ile Thr Gln Ala Val Lys
                165                 170                 175

Ala Val Glu Lys His Thr Gln Thr Phe Leu His Arg Glu Lys Lys Lys
            180                 185                 190

Leu Pro Ser Phe Leu Asp Trp Phe Gly Trp Cys Thr Trp Asp Ala Phe
        195                 200                 205

Tyr Thr Asp Ala Thr Ala Glu Gly Val Val Glu Gly Leu Lys Ser Leu
    210                 215                 220

Ser Glu Gly Gly Ala Pro Pro Lys Phe Leu Ile Ile Asp Asp Gly Trp
225                 230                 235                 240

Gln Gln Ile Glu Ala Lys Pro Lys Asp Ala Asp Cys Val Val Gln Glu
                245                 250                 255

Gly Ala Gln Phe Ala Ser Arg Leu Ser Gly Ile Lys Glu Asn His Lys
            260                 265                 270

Phe Gln Lys Asn Gly Asn Asn Tyr Asp Gln Val Pro Gly Leu Lys Val
        275                 280                 285

Val Val Asp Asp Ala Lys Lys Gln His Lys Val Lys Phe Val Tyr Ala
    290                 295                 300

Trp His Ala Leu Ala Gly Tyr Trp Gly Gly Val Lys Pro Ala Ser Pro
305                 310                 315                 320

Gly Met Glu His Tyr Asp Ser Ala Leu Ala Tyr Pro Val Gln Ser Pro
                325                 330                 335

Gly Met Leu Gly Asn Gln Pro Asp Ile Val Val Asp Ser Leu Ala Val
            340                 345                 350

```
His Gly Ile Gly Leu Val His Pro Lys Lys Val Phe Asn Phe Tyr Asn
            355                 360                 365

Glu Leu His Ser Tyr Leu Ala Ser Cys Gly Ile Asp Gly Val Lys Val
370                 375                 380

Asp Val Gln Asn Ile Ile Glu Thr Leu Gly Ala Gly His Gly Gly Arg
385                 390                 395                 400

Val Thr Leu Thr Arg Ser Tyr His Gln Ala Leu Glu Ala Ser Ile Ala
                405                 410                 415

Arg Asn Phe Ser Asp Asn Gly Cys Ile Ala Cys Met Cys His Asn Thr
            420                 425                 430

Asp Ser Leu Tyr Ser Ala Lys Gln Thr Ala Val Arg Ala Ser Asp
            435                 440                 445

Asp Tyr Tyr Pro Arg Asp Pro Thr Ser His Thr Ile His Ile Ser Ser
450                 455                 460

Val Ala Tyr Asn Ser Leu Phe Leu Gly Glu Phe Met Gln Pro Asp Trp
465                 470                 475                 480

Asp Met Phe His Ser Leu His Pro Thr Ala Glu Tyr His Gly Ala Ala
                485                 490                 495

Arg Ala Ile Gly Gly Cys Ala Ile Tyr Val Ser Asp Lys Pro Gly Asn
            500                 505                 510

His Asn Phe Asp Leu Leu Lys Lys Leu Val Leu Pro Asp Gly Ser Val
            515                 520                 525

Leu Arg Ala Gln Leu Pro Gly Arg Pro Thr Arg Asp Ser Leu Phe Asn
            530                 535                 540

Asp Pro Ala Arg Asp Gly Ile Ser Leu Leu Lys Ile Trp Asn Met Asn
545                 550                 555                 560

Lys Cys Ser Gly Val Val Gly Val Phe Asn Cys Gln Gly Ala Gly Trp
                565                 570                 575

Cys Arg Ile Thr Lys Lys Thr Arg Ile His Asp Glu Ser Pro Gly Thr
            580                 585                 590

Leu Thr Thr Ser Val Arg Ala Ala Asp Val Asp Ala Ile Ser Gln Val
            595                 600                 605

Ala Gly Ala Asp Trp Lys Gly Asp Thr Ile Val Tyr Ala Tyr Arg Ser
610                 615                 620

Gly Asp Leu Ile Arg Leu Pro Lys Gly Ala Ser Val Pro Val Thr Leu
625                 630                 635                 640

Lys Val Leu Glu Tyr Asp Leu Leu His Ile Ser Pro Leu Lys Asp Ile
                645                 650                 655

Ala Ser Asn Ile Ser Phe Ala Pro Ile Gly Leu Leu Asp Met Phe Asn
            660                 665                 670

Thr Gly Gly Ala Val Glu Gln Val Asn Val Gln Val Val Glu Pro Ile
            675                 680                 685

Pro Glu Phe Asp Gly Glu Val Ala Ser Glu Leu Thr Cys Ser Leu Pro
690                 695                 700

Asn Asp Arg Pro Pro Thr Ala Thr Ile Thr Met Lys Ala Arg Gly Cys
705                 710                 715                 720

Arg Arg Phe Gly Leu Tyr Ser Ser Gln Arg Pro Leu Lys Cys Ser Val
                725                 730                 735

Asp Lys Val Asp Val Asp Phe Val Tyr Asp Val Thr Gly Leu Val
            740                 745                 750

Thr Phe Glu Ile Pro Ile Pro Thr Glu Met Tyr Arg Trp Asp Ile
            755                 760                 765

Glu Ile Gln Val
```

<210> SEQ ID NO 14
<211> LENGTH: 378
<212> TYPE: PRT
<213> ORGANISM: Coffea arabica

<400> SEQUENCE: 14

| | | | | | | | | | | | | | | |
|---|---|---|---|---|---|---|---|---|---|---|---|---|---|---|
| Met | Val | Lys | Ser | Pro | Gly | Thr | Glu | Asp | Tyr | Thr | Arg | Arg | Ser | Leu | Leu |
| 1 | | | | 5 | | | | | 10 | | | | | 15 | |
| Ala | Asn | Gly | Leu | Gly | Leu | Thr | Pro | Pro | Met | Gly | Trp | Asn | Ser | Trp | Asn |
| | | | 20 | | | | | 25 | | | | | 30 | | |
| His | Phe | Arg | Cys | Asn | Leu | Asp | Glu | Lys | Leu | Ile | Arg | Glu | Thr | Ala | Asp |
| | | 35 | | | | | 40 | | | | | 45 | | | |
| Ala | Met | Val | Ser | Lys | Gly | Leu | Ala | Ala | Leu | Gly | Tyr | Lys | Tyr | Ile | Asn |
| | 50 | | | | | 55 | | | | | 60 | | | | |
| Leu | Asp | Asp | Cys | Trp | Ala | Glu | Leu | Asn | Arg | Asp | Ser | Gln | Gly | Asn | Leu |
| 65 | | | | | 70 | | | | | 75 | | | | | 80 |
| Val | Pro | Lys | Gly | Ser | Thr | Phe | Pro | Ser | Gly | Ile | Lys | Ala | Leu | Ala | Asp |
| | | | | 85 | | | | | 90 | | | | | 95 | |
| Tyr | Val | His | Ser | Lys | Gly | Leu | Lys | Leu | Gly | Ile | Tyr | Ser | Asp | Ala | Gly |
| | | | 100 | | | | | 105 | | | | | 110 | | |
| Thr | Gln | Thr | Cys | Ser | Lys | Thr | Met | Pro | Gly | Ser | Leu | Gly | His | Glu | Glu |
| | | 115 | | | | | 120 | | | | | 125 | | | |
| Gln | Asp | Ala | Lys | Thr | Phe | Ala | Ser | Trp | Gly | Val | Asp | Tyr | Leu | Lys | Tyr |
| | 130 | | | | | 135 | | | | | 140 | | | | |
| Asp | Asn | Cys | Asn | Asn | Asn | Ile | Ser | Pro | Lys | Glu | Arg | Tyr | Pro | Ile |
| 145 | | | | | 150 | | | | | 155 | | | | | 160 |
| Met | Ser | Lys | Ala | Leu | Leu | Asn | Ser | Gly | Arg | Ser | Ile | Phe | Phe | Ser | Leu |
| | | | | 165 | | | | | 170 | | | | | 175 | |
| Cys | Glu | Trp | Gly | Glu | Glu | Asp | Pro | Ala | Thr | Trp | Ala | Lys | Glu | Val | Gly |
| | | | 180 | | | | | 185 | | | | | 190 | | |
| Asn | Ser | Trp | Arg | Thr | Thr | Gly | Asp | Ile | Asp | Asp | Ser | Trp | Ser | Ser | Met |
| | | 195 | | | | | 200 | | | | | 205 | | | |
| Thr | Ser | Arg | Ala | Asp | Met | Asn | Asp | Lys | Trp | Ala | Ser | Tyr | Ala | Gly | Pro |
| | 210 | | | | | 215 | | | | | 220 | | | | |
| Gly | Gly | Trp | Asn | Asp | Pro | Asp | Met | Leu | Glu | Val | Gly | Asn | Gly | Met |
| 225 | | | | | 230 | | | | | 235 | | | | | 240 |
| Thr | Thr | Thr | Glu | Tyr | Arg | Ser | His | Phe | Ser | Ile | Trp | Ala | Leu | Ala | Lys |
| | | | | 245 | | | | | 250 | | | | | 255 | |
| Ala | Pro | Leu | Leu | Ile | Gly | Cys | Asp | Ile | Arg | Ser | Met | Asp | Gly | Ala | Thr |
| | | | 260 | | | | | 265 | | | | | 270 | | |
| Phe | Gln | Leu | Leu | Ser | Asn | Ala | Glu | Val | Ile | Ala | Val | Asn | Gln | Asp | Lys |
| | | 275 | | | | | 280 | | | | | 285 | | | |
| Leu | Gly | Val | Gln | Gly | Asn | Lys | Val | Lys | Thr | Tyr | Gly | Asp | Leu | Glu | Val |
| | 290 | | | | | 295 | | | | | 300 | | | | |
| Trp | Ala | Gly | Pro | Leu | Ser | Gly | Lys | Arg | Val | Ala | Val | Ala | Leu | Trp | Asn |
| 305 | | | | | 310 | | | | | 315 | | | | | 320 |
| Arg | Gly | Ser | Ser | Thr | Ala | Thr | Ile | Thr | Ala | Tyr | Trp | Ser | Asp | Val | Gly |
| | | | | 325 | | | | | 330 | | | | | 335 | |
| Leu | Pro | Ser | Thr | Ala | Val | Val | Asn | Ala | Arg | Asp | Leu | Trp | Ala | His | Ser |
| | | | 340 | | | | | 345 | | | | | 350 | | |
| Thr | Glu | Lys | Ser | Val | Lys | Gly | Gln | Ile | Ser | Ala | Ala | Val | Asp | Ala | His |
| | | 355 | | | | | 360 | | | | | 365 | | | |

Asp Ser Lys Met Tyr Val Leu Thr Pro Gln
    370                 375

<210> SEQ ID NO 15
<211> LENGTH: 398
<212> TYPE: PRT
<213> ORGANISM: Artificial Sequence
<220> FEATURE:
<223> OTHER INFORMATION: recombinant human alpha-galactosidase A

<400> SEQUENCE: 15

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45

Gly Trp Lys Asp Ala Gly Tyr Glu Tyr Leu Cys Ile Asp Asp Cys Trp
    50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
    130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
    210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
        275                 280                 285

Asn Gln Asp Pro Leu Gly Lys Gln Gly Tyr Gln Leu Arg Gln Gly Asp
    290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

-continued

```
Ile Thr Gln Leu Leu Pro Val Lys Arg Lys Leu Gly Phe Tyr Glu Trp
        355                 360                 365
Thr Ser Arg Leu Arg Ser His Ile Asn Pro Thr Gly Thr Val Leu Leu
    370                 375                 380
Gln Leu Glu Asn Thr Met Gln Met Ser Leu Lys Asp Leu Leu
385                 390                 395
```

STABILIZED ALPHA-GALACTOSIDASE AND USES THEREOF

RELATED APPLICATIONS

This application is a National Phase of PCT Patent Application No. PCT/IL2011/000209 having International filing date of Mar. 2, 2011, which claims the benefit of priority under 35 USC §119(e) of U.S. Provisional Patent Application Nos. 61/309,487 filed on Mar. 2, 2010, 61/434,499 filed on Jan. 20, 2011 and 61/434,503 filed on Jan. 20, 2011, and which is also a Continuation-In-Part (CIP) of PCT Patent Application No. PCT/IL2010/000956 having International filing date of Nov. 17, 2010.

PCT Patent Application No. PCT/IL2010/000956 claims the benefit of priority under 35 USC §119(e) of U.S. Provisional Patent Application No. 61/261,787 filed on Nov. 17, 2009.

The contents of the above applications are all incorporated by reference as if fully set forth herein in their entirety.

FIELD AND BACKGROUND OF THE INVENTION

The present invention, in some embodiments thereof, relates to novel multimeric protein structures and, more particularly, but not exclusively, to multimeric protein structures of α-galactosidase and to uses thereof in treating Fabry disease.

The lysosomal enzyme α-galactosidase-A (α-GAL or α-Gal A; EC 3.2.1.22) catalyzes the removal of galactose from oligosaccharides, glycoproteins and glycolipids during the catabolism of macromolecules. Deficiencies in lysosomal enzymes lead to the accumulation of their substrates in the tissues, conditions known as lysosomal storage diseases. In humans, the absence of functional α-galactosidase-A leads to the accumulation of glycolipids containing terminal α-galactose residues (primarily globotriaosylceramide, which is also referred to as "ceramide trihexoside", "CTH" or "Gb$_3$") in the tissues, leading to Fabry disease. Fabry disease is an X-linked recessive disorder, first described in 1898, characterized by chronic pain, ocular opacities, liver and kidney impairment, skin lesions, vascular deterioration and/or cardiac deficiencies. Recombinant human α-galactosidase-A has the ability to restore enzyme function in patients, and enzyme replacement therapy (ERT) using α-GAL was approved in the United States in 2003 as a treatment for Fabry disease. α-GAL became the second recombinant protein approved for the treatment of a lysosomal storage disorder after β-glucosidase, a treatment for Gaucher disease.

Endogenous and recombinant α-GALs catalyze the hydrolysis of terminal galactosylated glycolipids in the lysosomes of cells of organs such as the liver, kidneys, spleen, heart, etc. This natural action site is characterized by its low pH, reaching as low as 4.5. Lysosomal enzymes, including α-GAL, are hence designed to exert their maximal activity at these low pH levels.

Current Fabry ERT treatments are based on mammalian-cell derived recombinant α-GAL which is considered to be a limited efficiency treatment. These treatments only decelerate the progress of the disease but are not able to stop its progress and do not offer a true and complete solution. Furthermore, in some cases, ERT with commercial recombinant α-GALs must be ceased due to development of an immunogenic response to the treatment and in some cases the treatment cannot be initiated in light of immunogenicity problems.

X-ray structure analysis reveals that human α-GAL is a homodimeric glycoprotein with each monomer composed of two domains, a $(\beta/\alpha)_8$ domain containing the active site and a C-terminal domain containing eight antiparallel β strands on two sheets in a β sandwich [Garman & Garboczi, *J Mol Biol* 2004, 337:319-335]. The two monomers are arranged in a head-to-tail assembly and the dimerization is non-covalent. The two monomers pack with an interface that extends the 75 Å width of the dimer and buries 2200 Å$^2$ of surface area. In the dimer interface, 30 residues from each monomer contribute to the interface. The two active sites of the dimer are separated by approximately 50 Å.

The crystal structure of α-Gal was solved for a non-liganded protein as well as for a galactose-liganded protein. These two structures exhibit little change between the liganded and non-liganded structures. Nevertheless, the use of galactose instead of the natural substrate, globotriaosylceramide (Gb$_3$), the latter characterized by long lipidic chains able to interact with the hydrophobic domain of one monomer while the terminal galactose interacts with the active site of the second monomer, may not lead to evidence of active site cooperativity. Furthermore, biochemical evidence does suggest such cooperativity, exemplifying the importance of the homodimeric quaternary structure [Bishop & Desnick, *J Biol Chem* 1981, 256:1307-1316]. Thus, the kinetic properties of human α-Gal were studied and cooperativity between the monomers of the homodimeric enzyme, each with an interacting catalytic site, was shown. It was therefore suggested that enzymatic activity and stability may be dependent on dimerization.

WO 2009/024977, by the present assignee, which is incorporated by reference as if fully set forth herein, teaches conjugates of a saccharide and a biomolecule, covalently linked therebetween via a non-hydrophobic linker, as well as medical uses utilizing such conjugates.

PCT International Patent Application No. PCT/IL2010/000956, by the present assignee, teaches methodologies which utilize α-galactosidase which exhibits a lysosomal activity at pH levels higher than lysosomal pH.

Additional background art include Bendele et al. [*Toxicological Sciences* 1998, 42:152-157], U.S. Pat. Nos. 5,256,804, 5,580,757 and 5,766,897, International Patent Application PCT/NL2007/050684 (published as WO 2008/075957), and Seely & Richey [*J Chromatography A* 2001, 908:235-241].

SUMMARY OF THE INVENTION

According to an aspect of some embodiments of the present invention there is provided a multimeric protein structure comprising at least two α-galactosidase monomers being covalently linked to one another via a linking moiety, the multimeric protein structure featuring a characteristic selected from the group consisting of:

(a) an α-galactosidase activity upon subjecting the multimeric protein structure to human plasma conditions for one hour, which is at least 10% higher than an activity of native α-galactosidase upon subjecting the native α-galactosidase to human plasma conditions for one hour;

(b) an α-galactosidase activity which decreases upon subjecting the multimeric protein structure to human plasma conditions for one hour by a percentage which is at least 10% less than the percentage by which an activity of the native α-galactosidase decreases upon subjecting the native α-galactosidase to human plasma conditions for one hour;

(c) an α-galactosidase activity which remains substantially unchanged upon subjecting the multimeric protein structure to human plasma conditions for one hour;

(d) an α-galactosidase activity, upon subjecting the multimeric protein structure to lysosomal conditions for one week, which is at least 10% higher than an activity of native α-galactosidase upon subjecting the native α-galactosidase to lysosomal conditions for one week;

(e) an α-galactosidase activity which decreases upon subjecting the multimeric protein structure to lysosomal conditions for one day by a percentage which is at least 10% less than the percentage by which an activity of the native α-galactosidase decreases upon subjecting the native α-galactosidase to lysosomal conditions for one day;

(f) an α-galactosidase activity which remains substantially unchanged upon subjecting the multimeric protein structure to lysosomal conditions for one day;

(g) an α-galactosidase activity, immediately upon subjecting the multimeric protein structure to lysosomal conditions, which is at least 10% higher than an activity of native α-galactosidase immediately upon subjecting the native form of the protein to lysosomal conditions;

(h) an α-galactosidase activity, immediately upon subjecting the multimeric protein structure to an aqueous solution having a pH of 7 and a temperature of 37° C., which is at least 10% higher than an activity of native α-galactosidase immediately upon subjecting the native α-galactosidase to an aqueous solution having a pH of 7 and a temperature of 37° C.; and (i) a circulating half-life in a physiological system which is higher by at least 20% than the circulating half-life of the native α-galactosidase.

According to an aspect of some embodiments of the present invention there is provided a multimeric protein structure comprising at least two α-galactosidase monomers being covalently linked to one another via a linking moiety, wherein the linking moiety is not present in native α-galactosidase.

According to an aspect of some embodiments of the present invention there is provided a pharmaceutical composition comprising a multimeric protein structure as described herein and a pharmaceutically acceptable carrier.

According to an aspect of some embodiments of the present invention there is provided a method of treating Fabry disease, the method comprising administering to a subject in need thereof a therapeutically effective amount of a multimeric protein structure as described herein, thereby treating the Fabry disease.

According to an aspect of some embodiments of the present invention there is provided a process of preparing a multimeric protein structure as described herein, the process comprising reacting α-galactosidase with a cross-linking agent which comprises the linking moiety described herein and at least two reactive groups.

According to some embodiments of the invention, the linking moiety described herein is not present in native α-galactosidase.

According to some embodiments of the invention, the multimeric protein structure features a characteristic selected from the group consisting of:

(a) an α-galactosidase activity, upon subjecting the multimeric protein structure to human plasma conditions for one hour, which is at least 10% higher than an activity of native α-galactosidase upon subjecting the native α-galactosidase to human plasma conditions for one hour;

(b) an α-galactosidase activity which decreases upon subjecting the multimeric protein structure to human plasma conditions for one hour by a percentage which is at least 10% less than the percentage by which an activity of the native α-galactosidase decreases upon subjecting the native α-galactosidase to human plasma conditions for one hour;

(c) an α-galactosidase activity which remains substantially unchanged upon subjecting the multimeric protein structure to human plasma conditions for one hour;

(d) an α-galactosidase activity, upon subjecting the multimeric protein structure to lysosomal conditions for one week, which is at least 10% higher than an activity of native α-galactosidase upon subjecting the native α-galactosidase to lysosomal conditions for one week;

(e) an α-galactosidase activity which decreases upon subjecting the multimeric protein structure to lysosomal conditions for one day by a percentage which is at least 10% less than the percentage by which an activity of the native α-galactosidase decreases upon subjecting the native α-galactosidase to lysosomal conditions for one day;

(f) an α-galactosidase activity which remains substantially unchanged upon subjecting the multimeric protein structure to lysosomal conditions for one day;

(g) an α-galactosidase activity, immediately upon subjecting the multimeric protein structure to lysosomal conditions, which is at least 10% higher than an activity of native α-galactosidase immediately upon subjecting the native α-galactosidase to lysosomal conditions;

(h) an α-galactosidase activity, immediately upon subjecting the multimeric protein structure to an aqueous solution having a pH of 7 and a temperature of 37° C., which is at least 10% higher than an activity of native α-galactosidase immediately upon subjecting the native α-galactosidase to an aqueous solution having a pH of 7 and a temperature of 37° C.; and (i) a circulating half-life in a physiological system which is higher than a circulating half-life of the native α-galactosidase.

According to some embodiments of the invention, the α-galactosidase activity of the multimeric protein structure which remains substantially unchanged upon subjecting the multimeric protein structure to lysosomal conditions for one day, further remains substantially unchanged upon subjecting the multimeric protein structure to lysosomal conditions for one week.

According to some embodiments of the invention, the circulating half-life of the multimeric protein structure which is higher than a circulating half-life of the native α-galactosidase, is higher by at least 20% than the circulating half-life of the native α-galactosidase.

According to some embodiments of the invention, the circulating half-life of the multimeric protein structure which is higher than a circulating half-life of the native α-galactosidase, is higher by at least 50% than the circulating half-life of the native α-galactosidase.

According to some embodiments of the invention, the multimeric protein structure is characterized by an α-galactosidase activity in an organ upon administration of the multimeric protein structure to a vertebrate, the organ being selected from the group consisting of a spleen, a heart and a kidney.

According to some embodiments of the invention, the multimeric protein structure comprises two α-galactosidase monomers, the protein structure being a dimeric protein structure.

According to some embodiments of the invention, the α-galactosidase is a human α-galactosidase.

According to some embodiments of the invention, the α-galactosidase is a plant recombinant α-galactosidase.

According to some embodiments of the invention, the α-galactosidase has an amino acids sequence selected from the group consisting of SEQ ID NO:1, SEQ ID NO:2 and SEQ ID NO:3.

According to some embodiments of the invention, the α-galactosidase is an alkaline α-galactosidase.

According to some embodiments of the invention, the α-galactosidase is an acid α-galactosidase.

According to some embodiments of the invention, the linking moiety comprises a poly(alkylene glycol).

According to some embodiments of the invention, the poly(alkylene glycol) comprises at least two functional groups, each functional group forming a covalent bond with one of the α-galactosidase monomers.

According to some embodiments of the invention, the at least two functional groups are terminal groups of the poly(alkylene glycol).

According to some embodiments of the invention, the at least one linking moiety has a general formula:

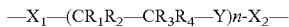

—$X_1$—$(CR_1R_2$—$CR_3R_4$—$Y)_n$-$X_2$— wherein each of $X_1$ and $X_2$ is a functional group that forms a covalent bond with at least one α-galactosidase monomer;
Y is O, S or $NR_5$;
n is an integer from 1 to 200; and
each of $R_1$, $R_2$, $R_3$, $R_4$ and $R_5$ is independently selected from the group consisting of hydrogen, alkyl, cycloalkyl, alkenyl, alkynyl, alkoxy, hydroxy, oxo, thiol and thioalkoxy.

According to some embodiments of the invention, at least one of the functional groups forms an amide bond with an α-galactosidase monomer.

According to some embodiments of the invention, n is an integer from 5 to 150.

According to some embodiments of the invention, n is an integer from 40 to 70.

According to some embodiments of the invention, the pharmaceutical composition further comprises a galactose.

According to some embodiments of the invention, the multimeric protein structure is for use as a medicament.

According to some embodiments of the invention, the medicament is for treating Fabry disease.

According to some embodiments of the invention, the multimeric protein structure is for use in treating Fabry disease.

According to some embodiments of the invention, the process comprises reacting dimeric α-galactosidase with the cross-linking agent.

According to some embodiments of the invention, the reactive groups comprise a leaving group.

According to some embodiments of the invention, the reactive group reacts with an amine group to form an amide bond.

According to some embodiments of the invention, each of the reactive groups is capable of forming a covalent bond between the linking moiety and at least one α-galactosidase monomer.

According to some embodiments of the invention, a molar ratio of the cross-linking agent to monomers of α-galactosidase is in a range of from 5:1 to 500:1.

According to some embodiments of the invention, the molar ratio is in a range of from 75:1 to 300:1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

(FIG. 26B);

Figure 29A:
FIGS. 29A and 29B present scans of SDS-PAGE gels showing plant recombinant human α-GAL-II (FIGS. 29A and 29B, lane 2), and plant recombinant human α-GAL-II which was reacted with bis-NHS-PEG$_{21}$ (FIG. 29A, lane 3), bis-NHS-PEG$_{45}$ (FIG. 29A, lane 4) or bis-NHS-PEG$_{68}$ (FIG.
Figure 29B:
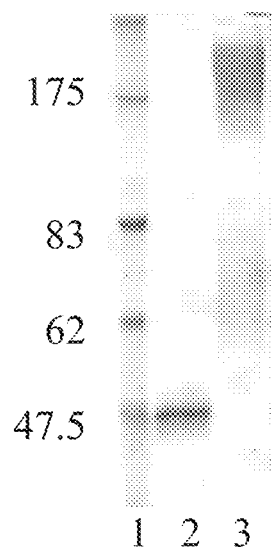
Figure 30A:
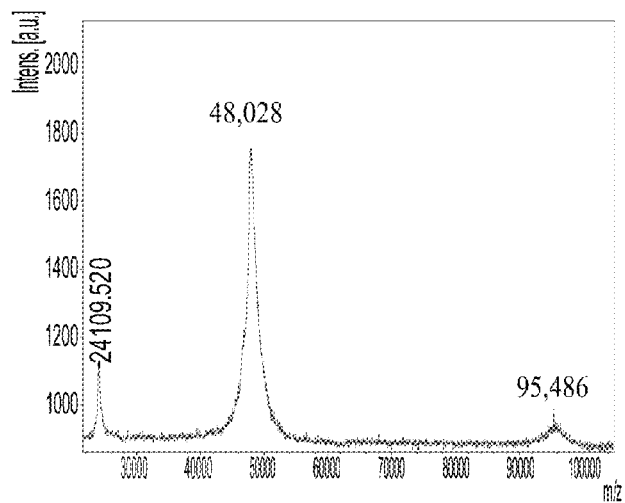
Figure 30B:
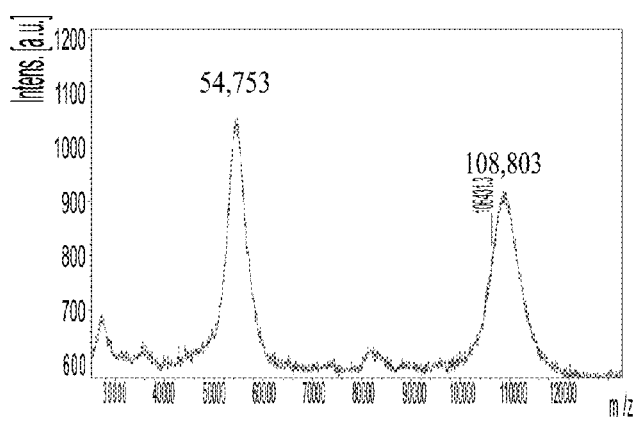
Figure 30C:
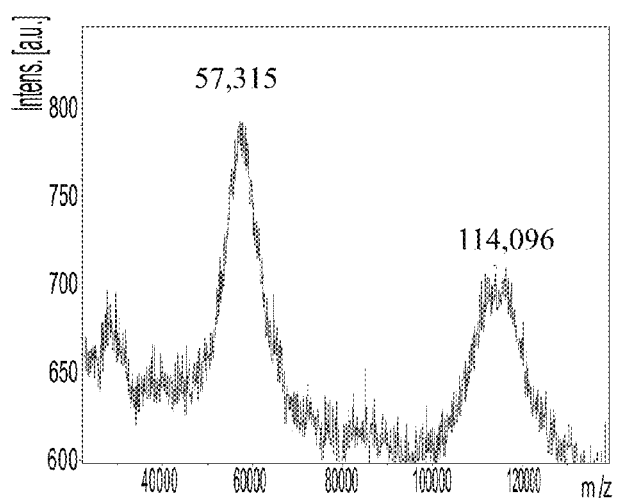
Figure 31A:
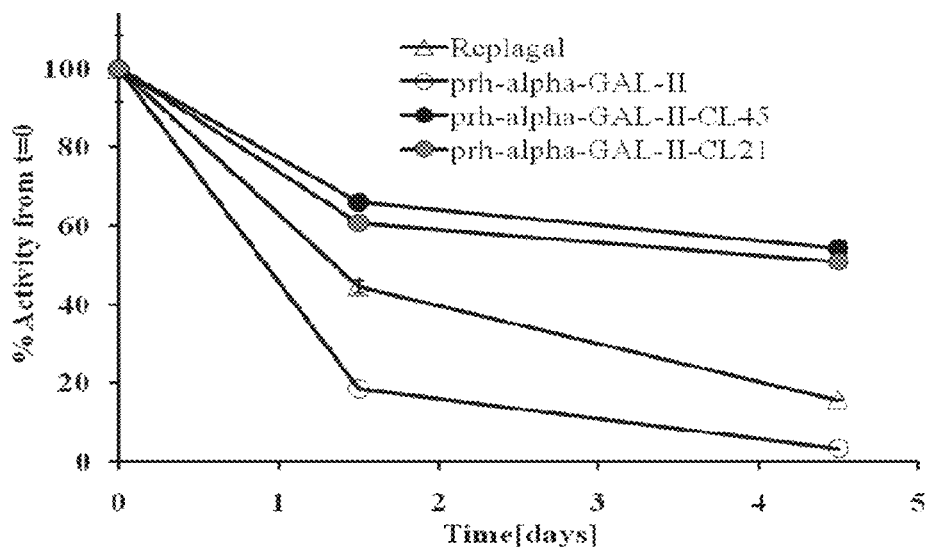
Figure 31B:
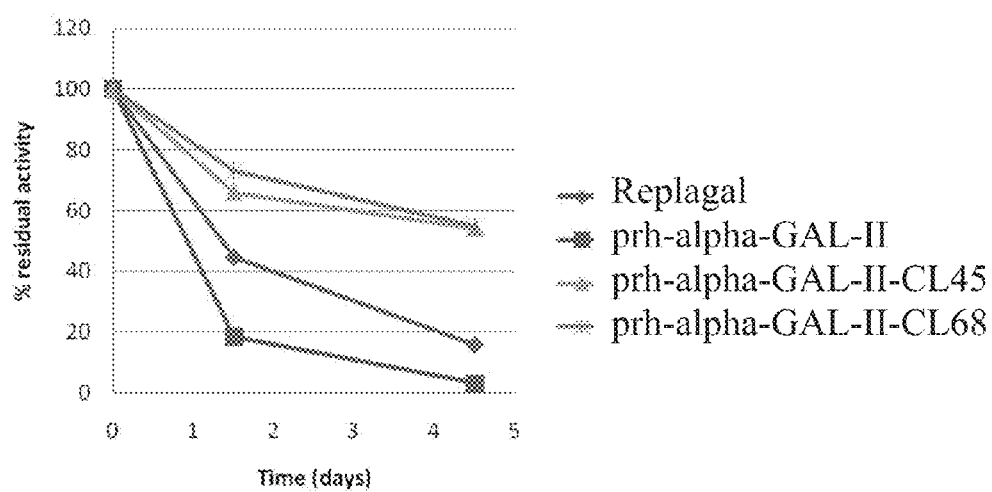
Figure 31C:
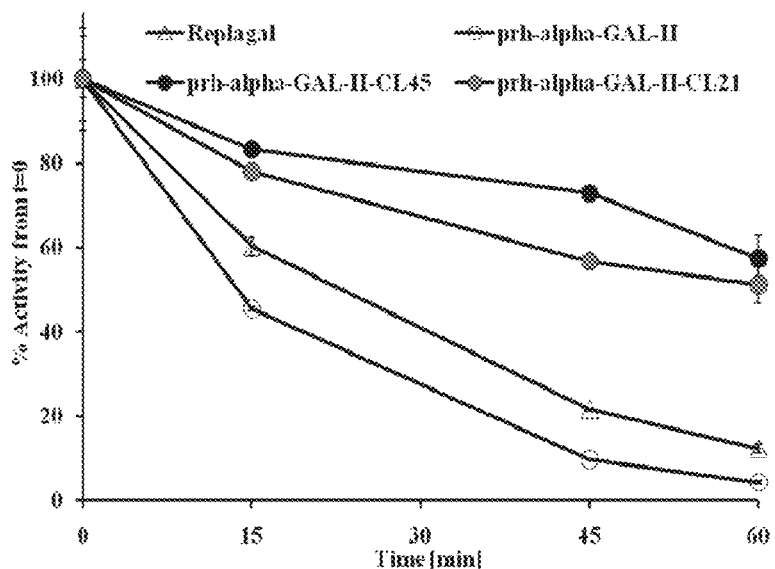
Figure 31D:
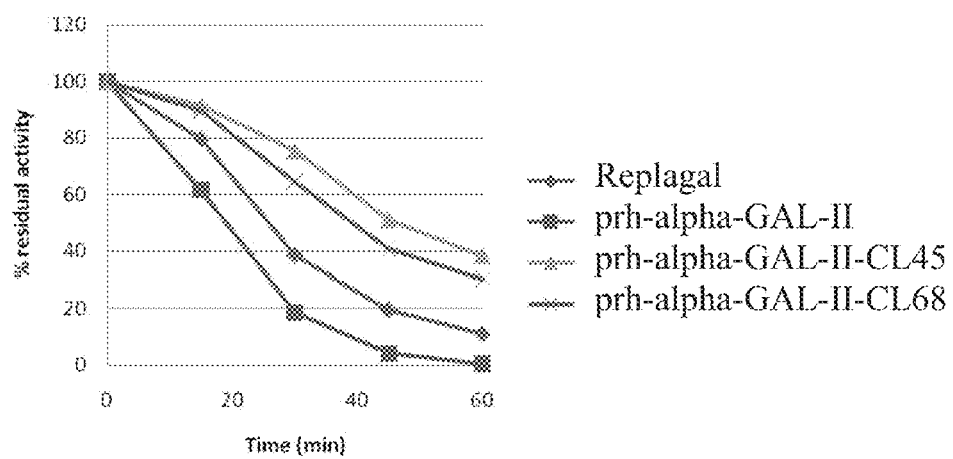
Figure 32A:
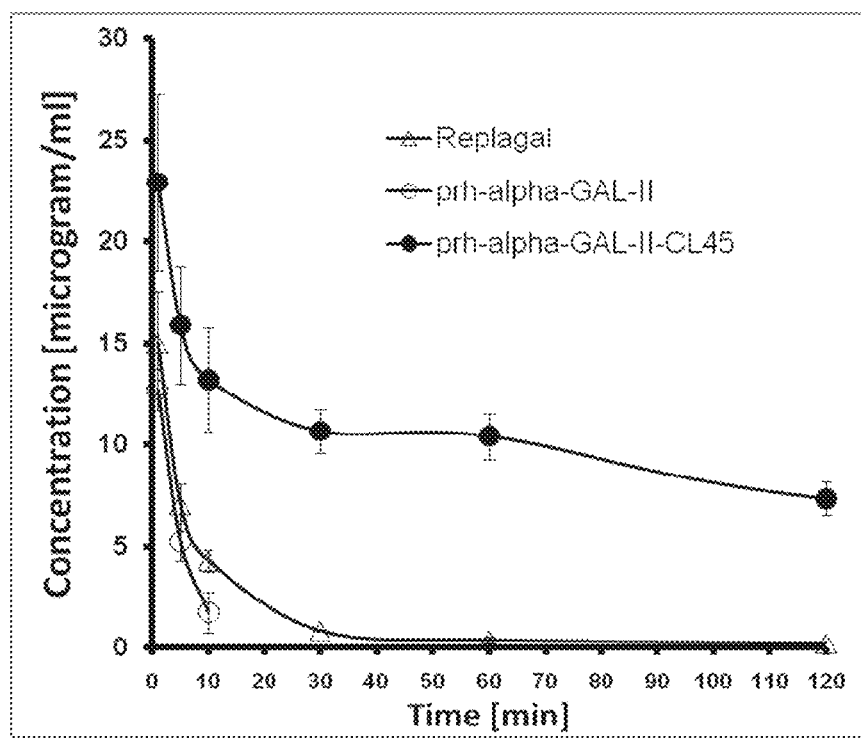
Figure 32B:
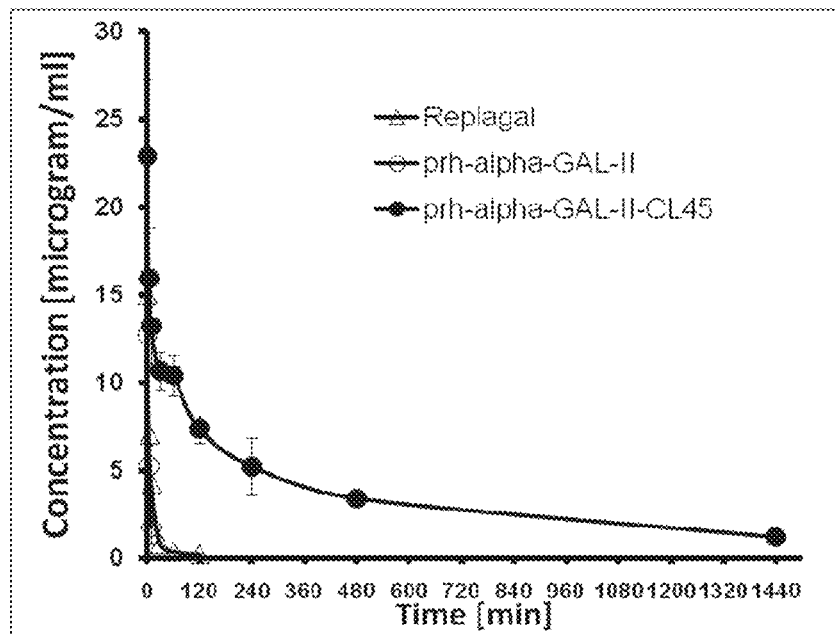
Figure 34A:
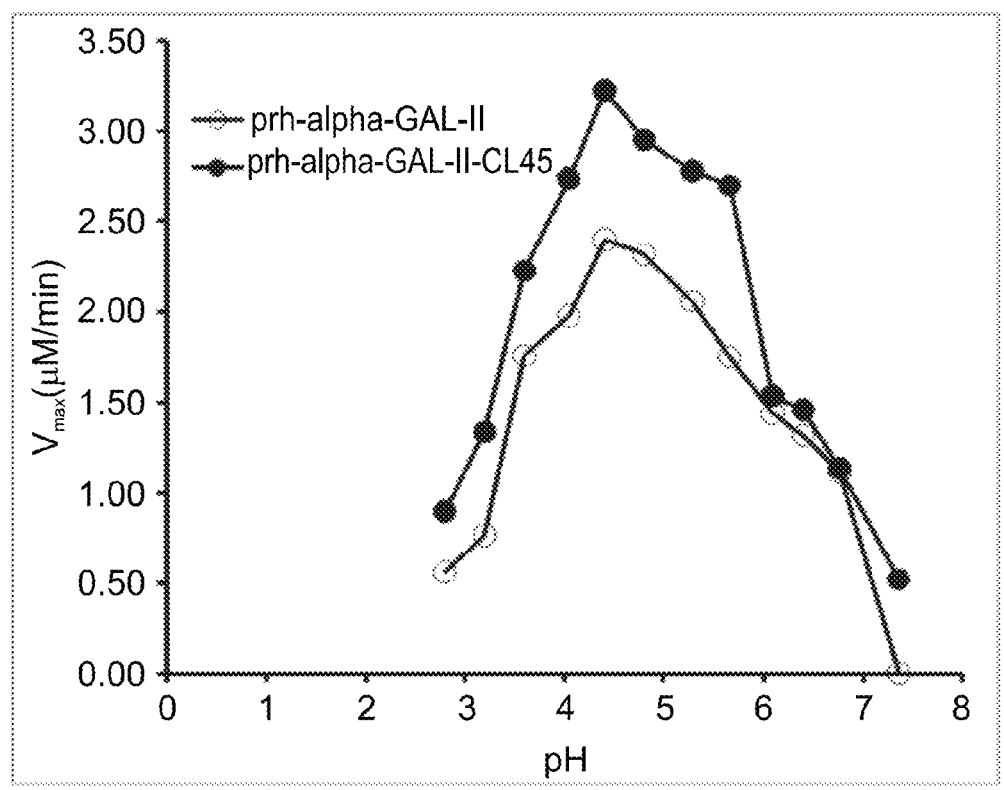
Figure 34B:
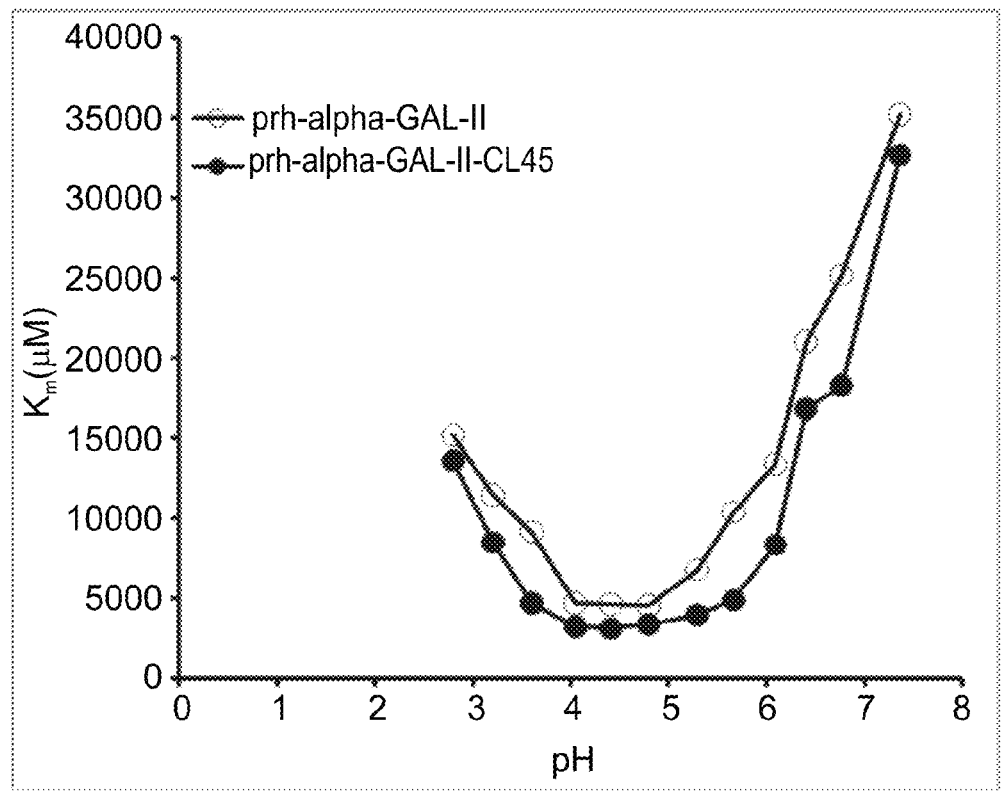
Figure 34C:
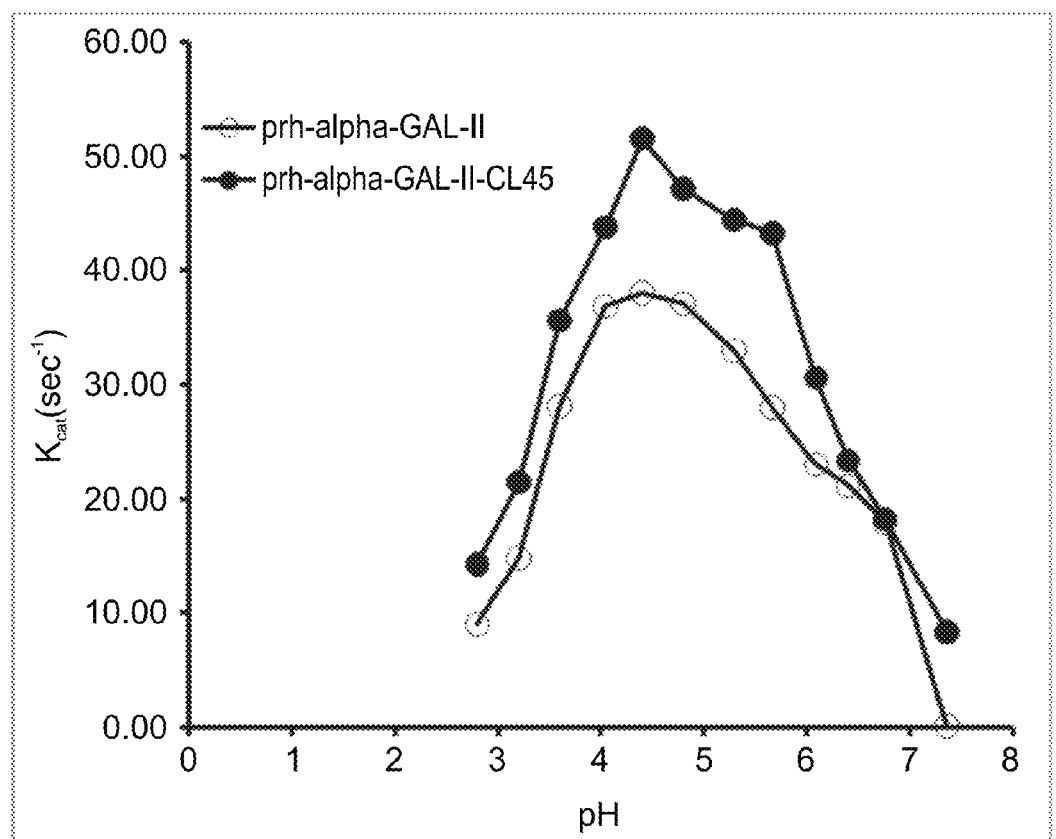
Figure 35:
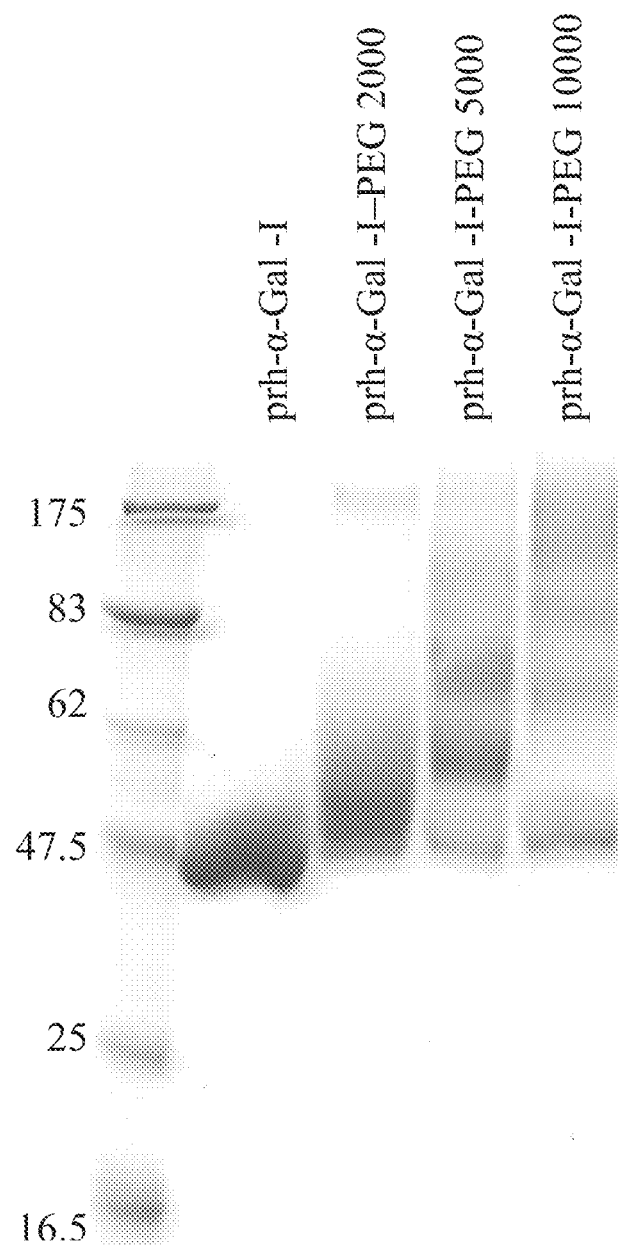
Figure 36A:
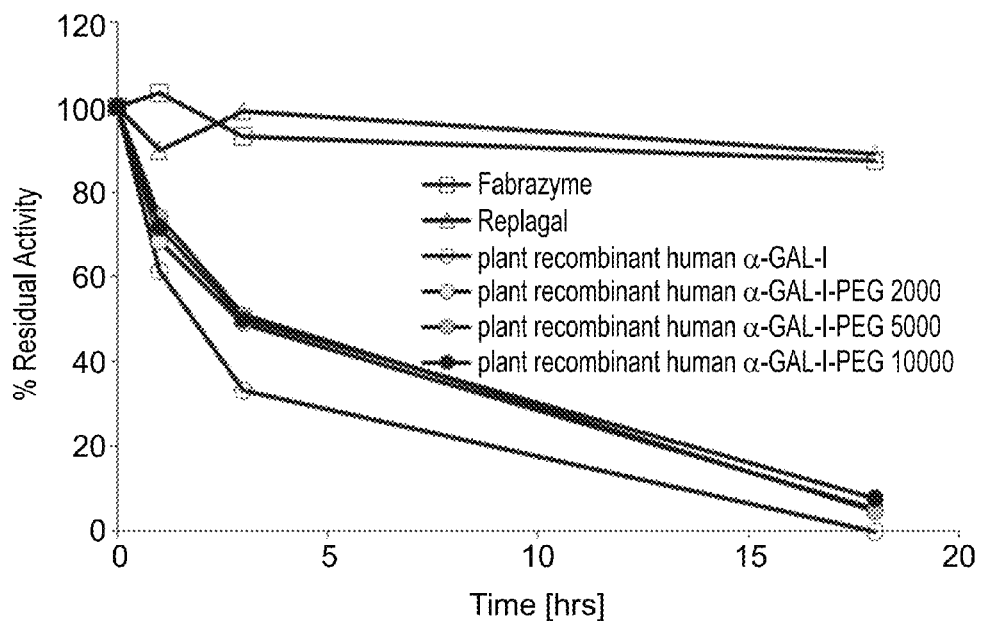
Figure 36B:
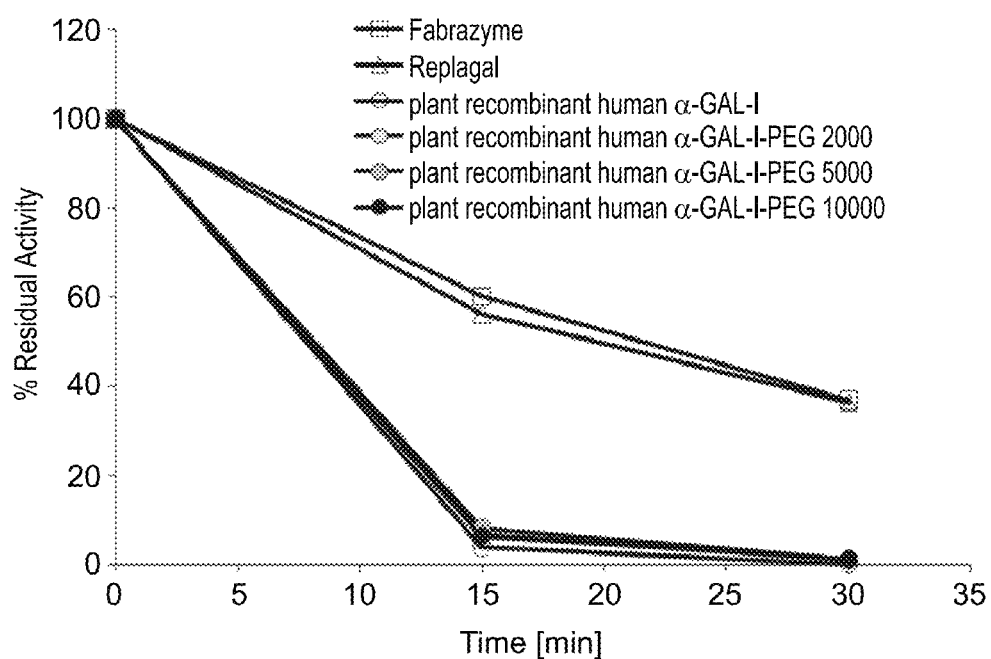
Figure 37:
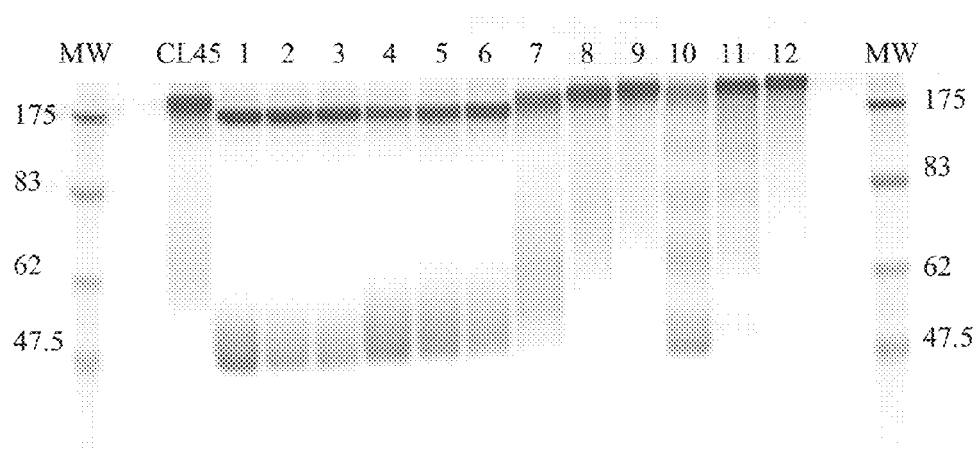
Figure 38:
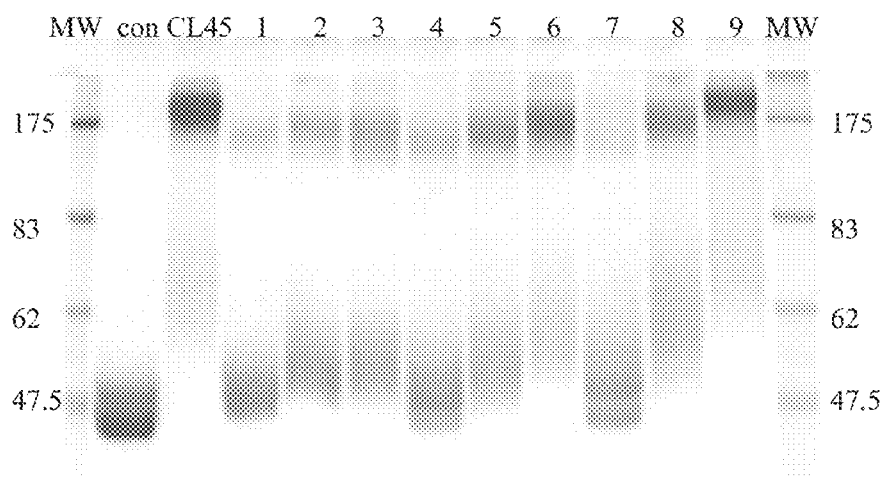
Figure 39:
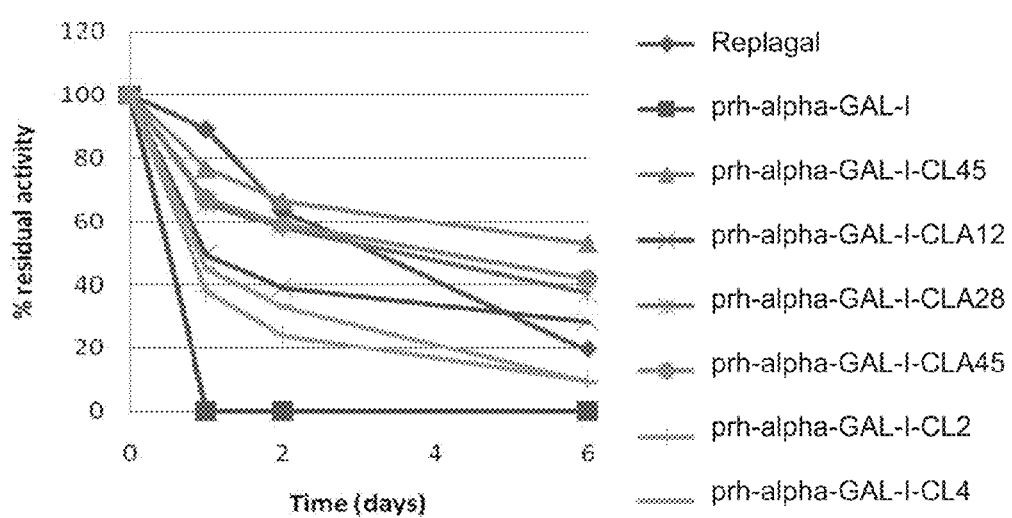
Figure 40A:
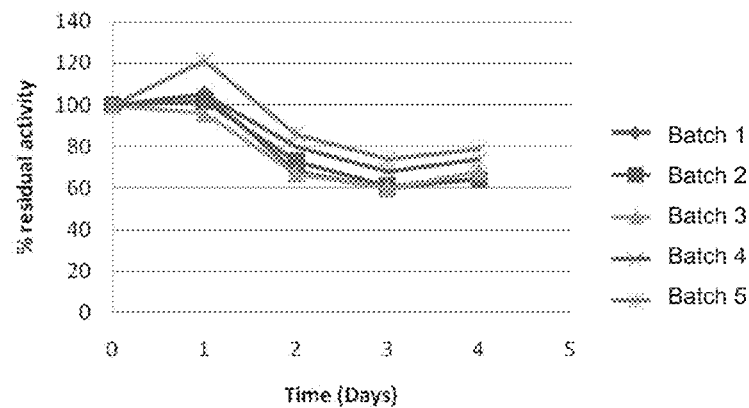
Figure 40B:
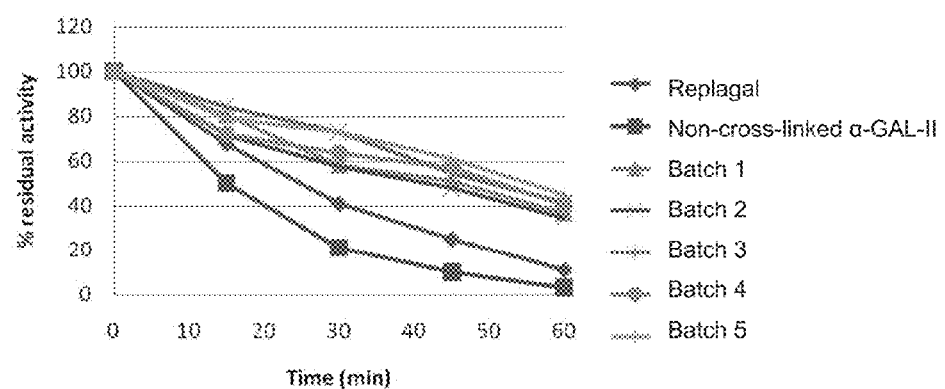
Figure 41:
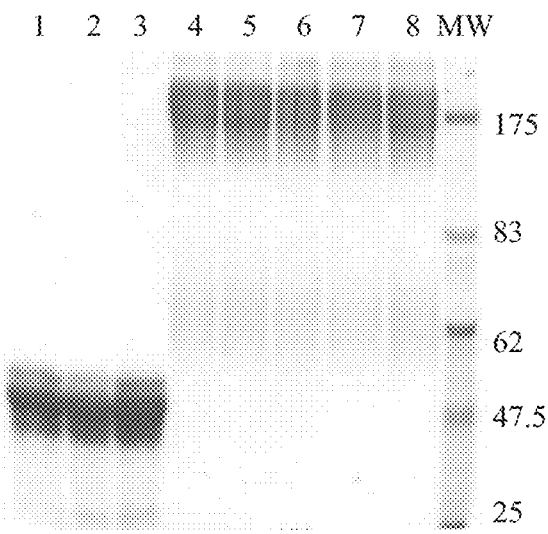
Figure 42:
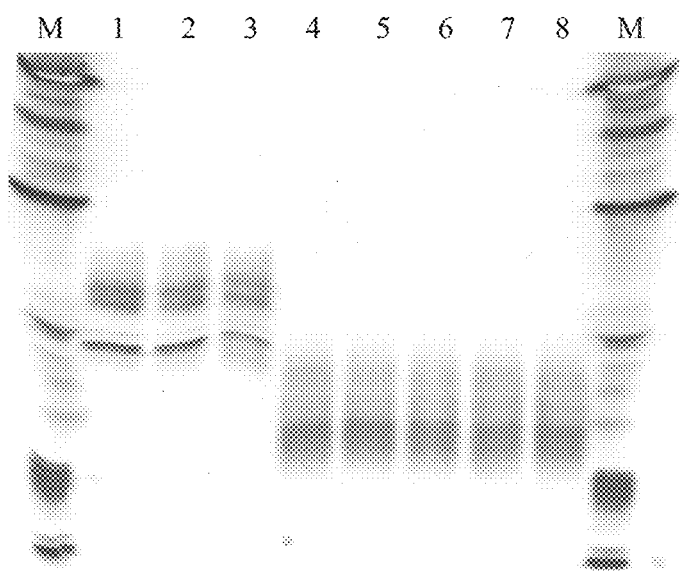
Figure 43A:
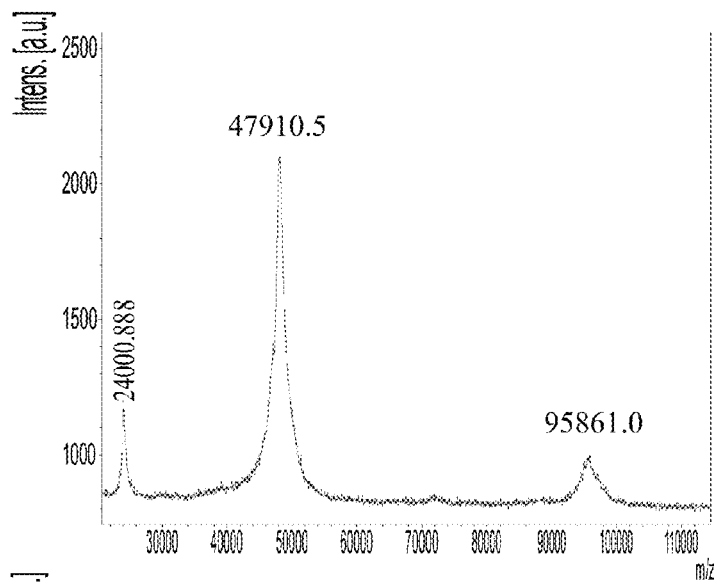
Figure 43B:
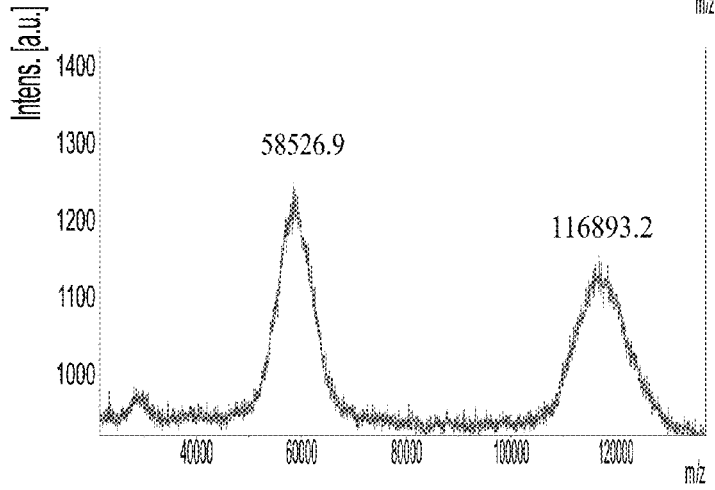
Figure 43C:
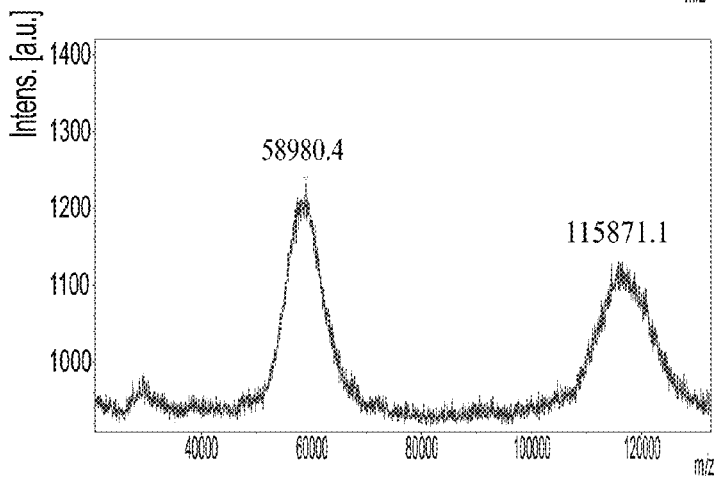
Figure 43D:
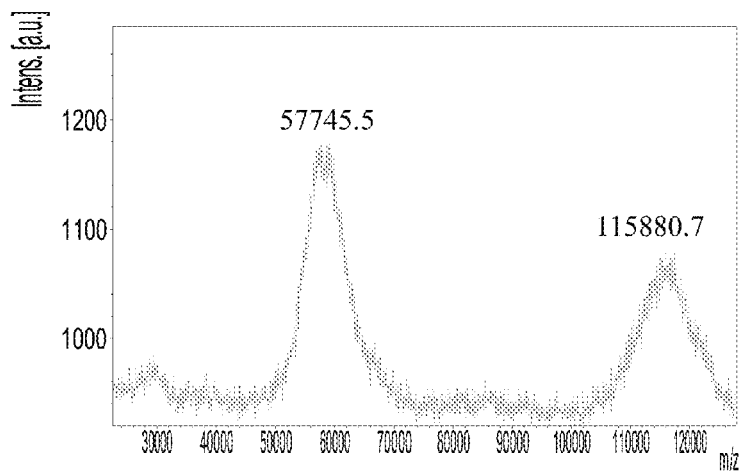
Figure 43E:
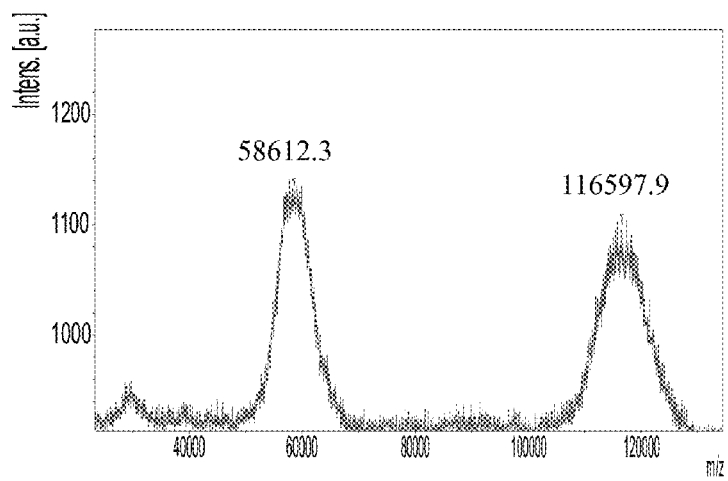
Figure 43F:
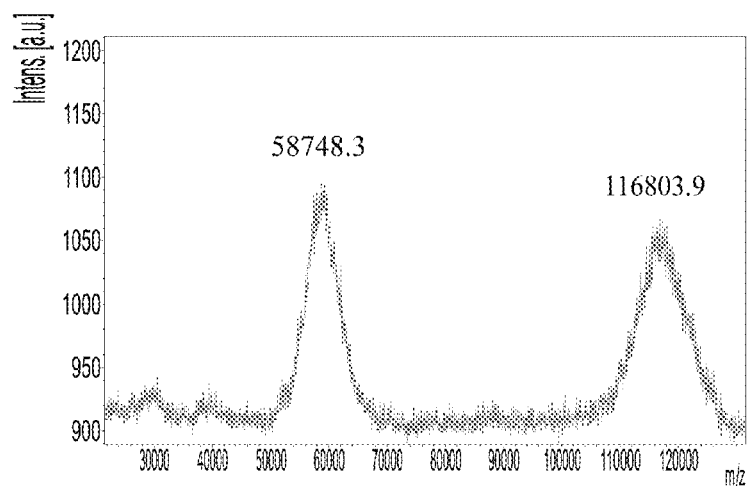
Figure 44:
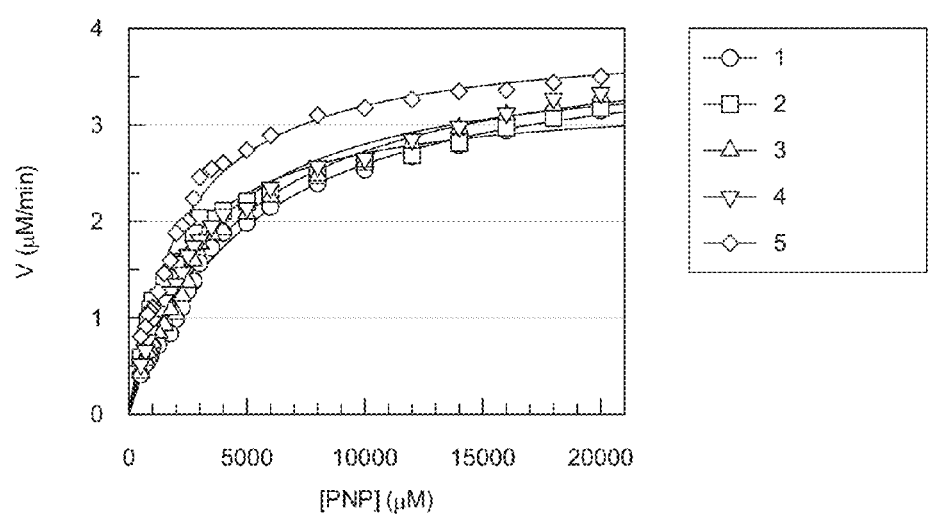

29B, lane 3), as well as molecular weight markers (FIGS. 29A and 29B, lane 1; molecular weights of markers are indicated in KDa units);

FIGS. 30A-30C are MALDI-TOF mass spectroscopy spectra of plant recombinant human α-GAL-II (FIG. 30A), and plant recombinant human α-GAL-II cross-linked by bis-NHS-PEG$_{21}$ (FIG. 30B) or bis-NHS-PEG$_{45}$ (FIG. 30C) (x-axis indicates m/z values, and m/z values (in Da units) of peaks are shown);

FIGS. 31A-31D are graphs showing the activity of Replagal® mammalian recombinant human α-GAL (Replagal), plant recombinant human α-GAL-II (prh-alpha-GAL-II) and plant recombinant human α-GAL-II cross-linked by bis-NHS-PEG$_{21}$ (prh-alpha-GAL-II-CL21; FIGS. 31A and 31C), bis-NHS-PEG$_{45}$ (prh-alpha-GAL-II-CL45; FIGS. 31A-31D) or bis-NHS-PEG$_{68}$ (prh-alpha-GAL-II-CL68; FIGS. 31B and 31D) as a function of incubation time under simulated lysosomal conditions (citrate phosphate buffer, pH 4.6, 37° C.) (FIGS. 31A and 31B) or in human plasma at 37° C. (FIGS. 31C and 31D) (data shown in FIGS. 31C and 31D are from different experiments);

FIGS. 32A and 32B are graphs showing the pharmacokinetic profiles of Replagal® α-GAL (Replagal), plant recombinant human α-GAL-II (prh-alpha-GAL-II), and plant recombinant human α-GAL-II cross-linked with bis-NHS-PEG$_{45}$ (prh-alpha-GAL-II-CL45) in the plasma of Fabry mice; concentration of each α-GAL is presented as a function of time following injection of α-GAL (FIGS. 32A and 32B present the same data at different time frames);

FIGS. 33A-33L are graphs showing the activity of Replagal® α-GAL (Replagal), plant recombinant human α-GAL-II (prh-alpha-GAL-II) and plant recombinant human α-GAL-II cross-linked with bis-NHS-PEG$_{45}$ (prh-alpha-GAL-II-CL45; FIGS. 33A-33L) or bis-NHS-PEG$_{21}$ (prh-alpha-GAL-II-CL21; FIGS. 33E-33L) in the hearts (FIGS. 33A, 33E and 33I), kidneys (FIGS. 33B, 33F and 33J), livers (FIGS. 33C, 33G and 33K) and spleens (FIGS. 33D, 33H and 33L) of Fabry mice 2 hours (FIGS. 33A-33H), 7 days (FIGS. 33A-33D and 33I-33L), 14 days (FIGS. 33A-33D) and 28 days (FIGS. 33A-33D) following injection of α-GAL;

FIGS. 34A-34C are graphs showing the kinetic parameters $V_{max}$ (FIG. 34A), $K_M$ (FIG. 34B) and $k_{cat}$ (FIG. 34C) for plant recombinant human α-GAL-II (prh-alpha-GAL-II) and plant recombinant human α-GAL-II cross-linked with bis-NHS-PEG$_{45}$ (prh-alpha-GAL-II-CL45), as a function of pH;

FIG. 35 presents a scan of an SDS-PAGE gel showing plant recombinant human α-GAL-I (prh-α-Gal-I), and plant recombinant human α-GAL-I which was reacted with methoxy-capped NHS-PEG having a molecular weight of 2 KDa (prh-α-Gal-1-PEG 2000), 5 KDa (prh-α-Gal-I-PEG 5000) or 10 KDa (prh-α-Gal-I-PEG 10000), as well as molecular weight markers (left lane; molecular weights of markers are indicated in KDa units);

FIGS. 36A and 36B are graphs showing the activity of Fabrazyme® mammalian recombinant human α-GAL (Fabrazyme), Replagal® mammalian recombinant human α-GAL (Replagal), plant recombinant human α-GAL-I and plant recombinant human α-GAL-I which was reacted with methoxy-capped NHS-PEG having a molecular weight of 2 KDa (α-Gal-1-PEG 2000), 5 KDa (α-Gal-1-PEG 5000) or 10 KDa (α-Gal-1-PEG 10000), as a function of incubation time under simulated lysosomal conditions (citrate phosphate buffer, pH 4.6, 37° C.) (FIG. 36A) or in human plasma at 37° C. (FIG. 36B);

FIG. 37 presents a scan of an SDS-PAGE gel showing plant recombinant α-GAL-I which was reacted with bis-NHS-PEG$_2$ (lanes 1-3), bis-NHS-PEG$_4$ (lanes 4-6), bis-NHS-PEG$_{68}$ (lanes 7-9), bis-NHS-PEG$_{150}$ (lanes 10-12) and bis-NHS-PEG$_{45}$ (CL45), at a molar ratio of 50:1 (lanes 1, 4, 7 and 10), 100:1 (lanes 2, 5, 8 and 11) and 200:1 (lanes 3, 6, 9 and 12) bis-NHS-PEG:α-GAL, as well as molecular weight markers (MW);

FIG. 38 presents a scan of an SDS-PAGE gel showing plant recombinant α-GAL-I which was reacted with bis-COOH-PEG$_{12}$ (lanes 1-3), bis-COOH-PEG$_{28}$ (lanes 4-6), bis-COOH-PEG$_{45}$ (lanes 7-9), and bis-NHS-PEG$_{45}$ (CL45), at a molar ratio of 50:1 (lanes 1, 4 and 7), 100:1 (lanes 2, 5 and 8) and 200:1 (lanes 3, 6 and 9) bis-NHS-PEG:α-GAL, as well as molecular weight markers (MW), and non-crosslinked plant recombinant α-GAL-I as a control (con);

FIG. 39 is a graph showing the activity of Replagal® α-GAL, plant recombinant human α-GAL-I (prh-α-GAL-I), and plant recombinant human α-GAL-I cross-linked with bis-NHS-PEG$_{45}$ (prh-α-GAL-1-CL45), bis-NHS-PEG$_4$ (prh-α-GAL-1-CL4), bis-NHS-PEG$_2$ (prh-α-GAL-1-CL2), bis-COOH-PEG$_{45}$ (prh-α-GAL-1-CLA45) bis-COOH-PEG$_{28}$ (prh-α-GAL-1-CLA28) or bis-COOH-PEG$_{12}$ (prh-α-GAL-1-CLA12) as a function of incubation time under simulated lysosomal conditions (citrate phosphate buffer, pH 4.6, 37° C.);

FIGS. 40A and 40B are graphs showing the activity of plant recombinant human α-GAL-II cross-linked by bis-NHS-PEG$_{45}$ as a function of incubation time under simulated lysosomal conditions (citrate phosphate buffer, pH 4.6, 37° C.) (FIG. 40A) or in human plasma at 37° C. (FIG. 40B) (FIG. 40B shows the activity of Replagal® mammalian recombinant α-GAL and non-cross-linked plant recombinant human α-GAL-II for comparison);

FIG. 41 presents a scan of an SDS-PAGE gel showing plant recombinant α-GAL-II from 3 different batches (lanes 1-3) and plant recombinant α-GAL-II which was reacted with bis-NHS-PEG$_{45}$ from 5 different batches (lanes 4-8), as well as molecular weight markers (MW);

FIG. 42 presents a scan of an isoelectric focusing gel showing plant recombinant α-GAL-II from 3 different batches (lanes 1-3) and plant recombinant α-GAL-II which was reacted with bis-NHS-PEG$_{45}$ from 5 different batches (lanes 4-8), as well as pH markers (M);

FIGS. 43A-43F are MALDI-TOF mass spectroscopy spectra of plant recombinant human α-GAL-II (FIG. 43A), and plant human α-GAL-II cross-linked by bis-NHS-PEG$_{45}$ from 5 different batches (FIGS. 43B-43F, respectively) (x-axis indicates m/z values, and m/z values (in Da units) of peaks are shown); and FIG. 44 is a graph showing the catalytic velocity (V) of α-GAL activity exhibited by plant human α-GAL-II cross-linked by bis-NHS-PEG$_{45}$ from 5 different batches, as a function of substrate (p-nitrophenyl-α-D-galactopyranoside) concentration.

DESCRIPTION OF SPECIFIC EMBODIMENTS OF THE INVENTION

The present invention, in some embodiments thereof, relates to novel multimeric protein structures and, more particularly, but not exclusively, to multimeric protein structures of α-galactosidase and to uses thereof in treating Fabry disease.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Deficiencies of a lysosomal protein (e.g., defects in a lysosomal protein or absence of a lysosomal protein) can cause considerable harm to the health of a subject (a lysosomal storage disease). Enzyme replacement therapy (ERT), in which the deficient protein is administered to a patient, has been used in attempts to treat lysosomal storage diseases. However, administration of the deficient protein does not necessarily result in a considerable and/or persistent increase in the activity of the protein in vivo.

Fabry disease is an example of an X-linked recessive (inherited) lysosomal storage disease which can cause a wide range of systemic symptoms. A deficiency of the lysosomal enzyme α-galactosidase A due to mutation causes a glycolipid known as globotriaosylceramide (also known as $Gb_3$ or ceramide trihexoside) to accumulate within the blood vessels, other tissues, and organs. This accumulation leads to an impairment of their proper function. Two enzyme replacement therapies (ERTs) are available to functionally compensate for α-galactosidase deficiency. Agalsidase alpha (Replagal®, Shire) and agalsidase beta (Fabrazyme®, Genzyme) are both recombinant forms of the human α-galactosidase A enzyme. These enzymes are difficult to manufacture and as such are expensive. Recently, contamination at Genzyme's Allston, Mass., plant caused a worldwide shortage of agalsidase beta, and supplies were rationed to patients at one-third the recommended dose.

As shown herein, α-galactosidases exert their maximal activity at low pH levels characteristic of lysosomes, while their activity at higher pH levels is compromised. Thus, for example, α-galactosidase used in ERT would have little ability to hydrolyze terminal galactosylated glycolipids in the serum of Fabry patients.

Moreover, as further shown herein, even under lysosomal conditions, the activity of α-galactosidases is gradually compromised, although at a slower rate than at higher pH levels.

Motivated by a need to solve the compromised activity of α-galactosidases, the present inventors have searched for stabilized forms of α-galactosidase (α-GAL). More specifically, the present inventors have envisioned that a stabilized form of α-galactosidase would exhibit longer lasting activity in general, including longer lasting activity in serum. The present inventors have thus designed and successfully prepared and practiced stabilized forms of native α-galactosidase and have indeed shown that such stabilized forms exhibit an improved performance, in terms of enhanced activity and/or a longer lasting activity under both lysosomal conditions and in a serum environment, which allows for an enhanced activity of the protein in vivo.

The present inventors have demonstrated a formation of stabilized forms of α-galactosidase which exhibit an improved performance by means of cross-linking native α-galactosidase, via formation of new covalent linkage between α-galactosidase monomers.

Figure 1:
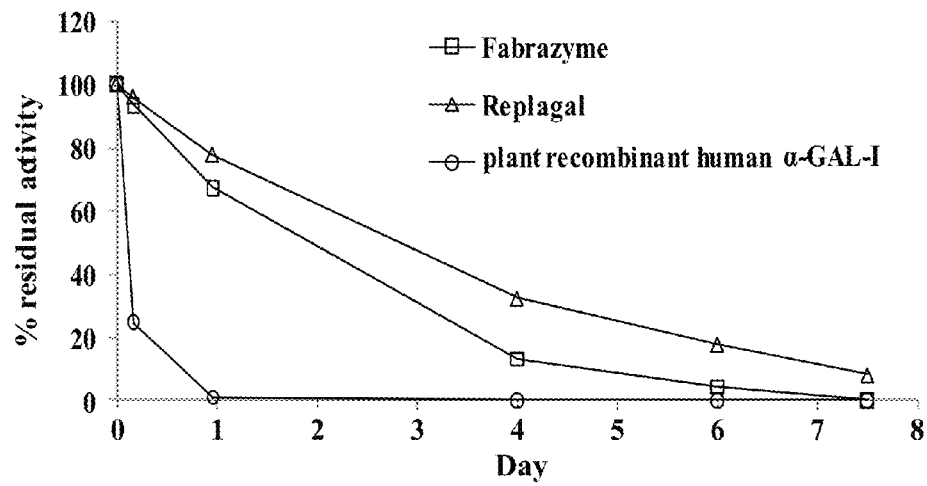
FIG. 1 is a graph showing the activity of Fabrazyme® α-GAL, Replagal® α-GAL and plant recombinant human α-GAL-I, as a function of incubation time under simulated lysosomal conditions (citrate phosphate buffer, pH 4.6, 37° C.)
Figure 2:
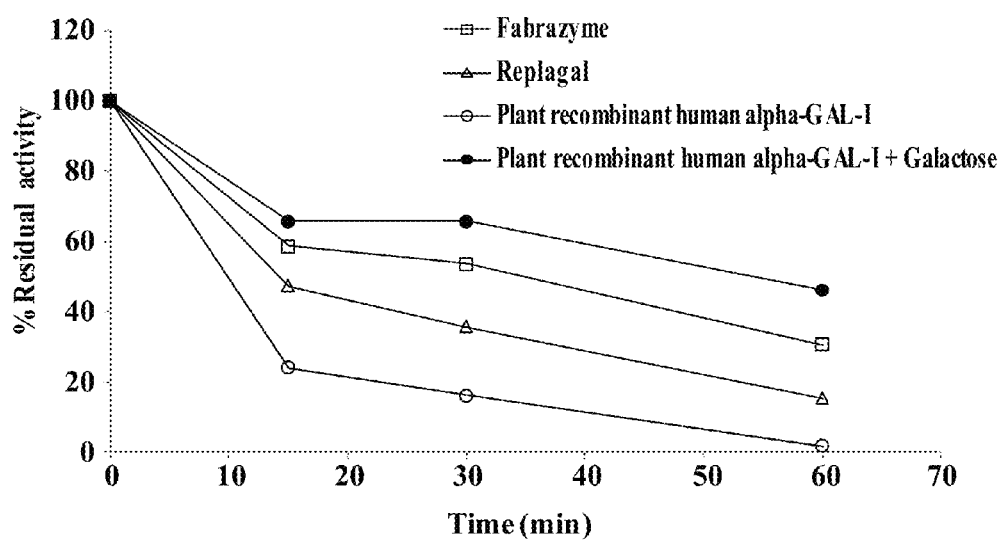
FIG. 2 is a graph showing the activity of Fabrazyme® α-GAL, Replagal® α-GAL, plant recombinant human α-GAL-I, and plant recombinant α-GAL-I with galactose (100 mg/mL), as a function of incubation time under simulated physiological conditions (pH 7.4, 37° C.)
Figure 3:
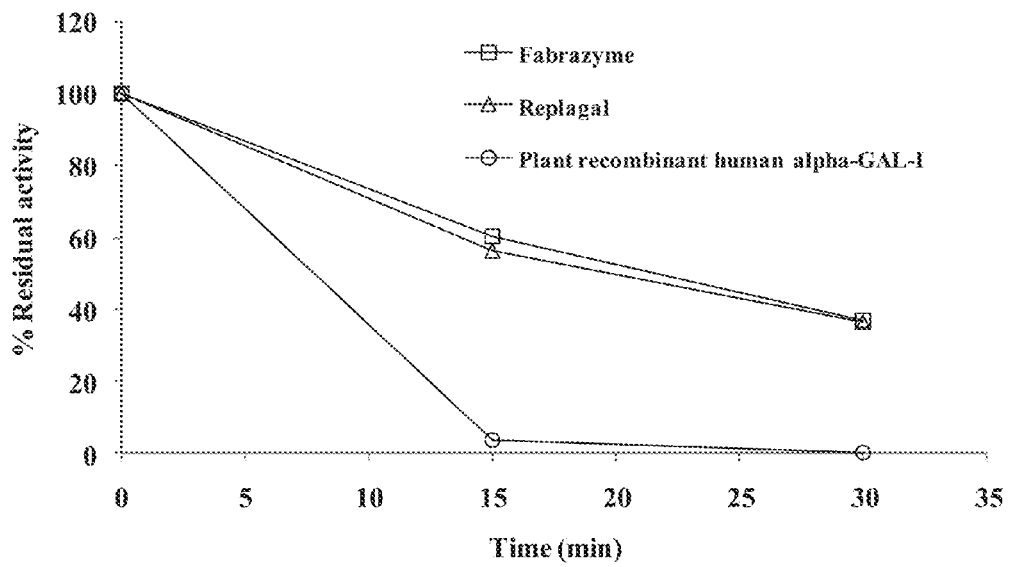
FIG. 3 is a graph showing the activity of Fabrazyme® α-GAL, Replagal® α-GAL and plant recombinant human α-GAL-I, as a function of incubation time in human plasma at 37° C.
Figure 4:
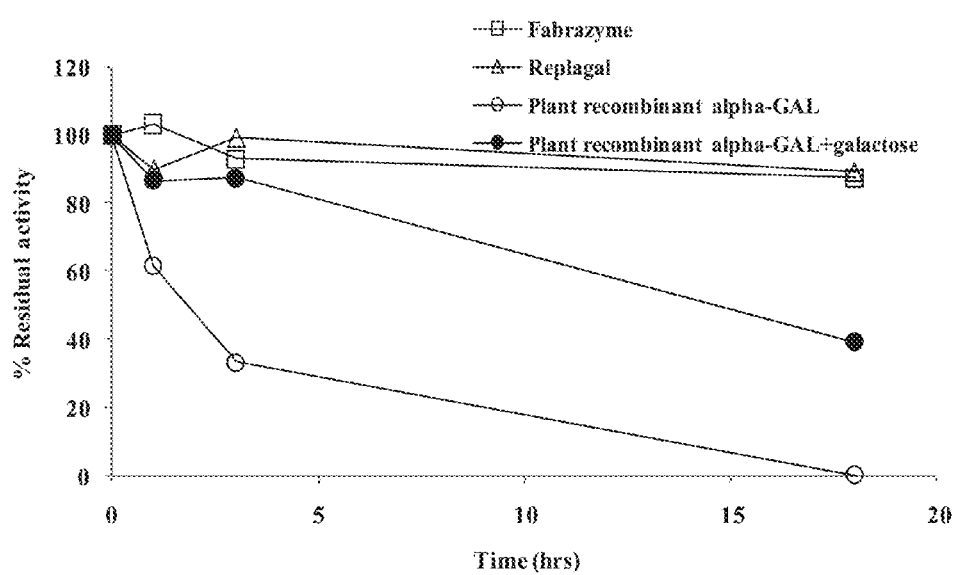
FIG. 4 is a graph showing the activity of Fabrazyme® α-GAL, Replagal® α-GAL, plant recombinant human α-GAL-I, and plant recombinant α-GAL-I with galactose (100 mg/mL), as a function of incubation time under simulated lysosomal conditions (citrate phosphate buffer, pH 4.6, 37° C.)

Referring now to the drawings, FIGS. 1 and 4 show the decline of enzyme activity under lysosomal conditions for plant recombinant human α-GAL I (prh-α-GAL I) and Fabrazyme® and Replagal® α-GAL. FIGS. 2 and 3 show the decline of enzyme activity under simulated physiological conditions or in human plasma, for the same α-GAL varieties. FIGS. 2 and 4 show that galactose decreases the rate of the decline in α-GAL activity.

Figure 5:
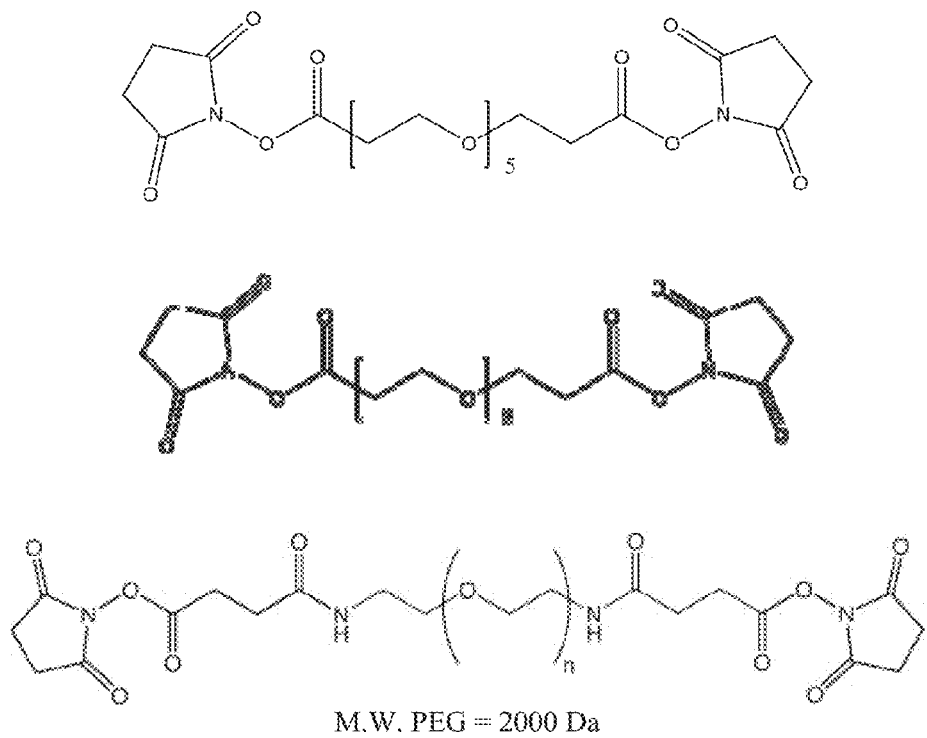
FIG. 5 is a scheme depicting the molecular structures of exemplary bis-N-hydroxysuccinimide-poly(ethylene glycol) (bis-NHS-PEG) cross-linking agents.
Figure 6:
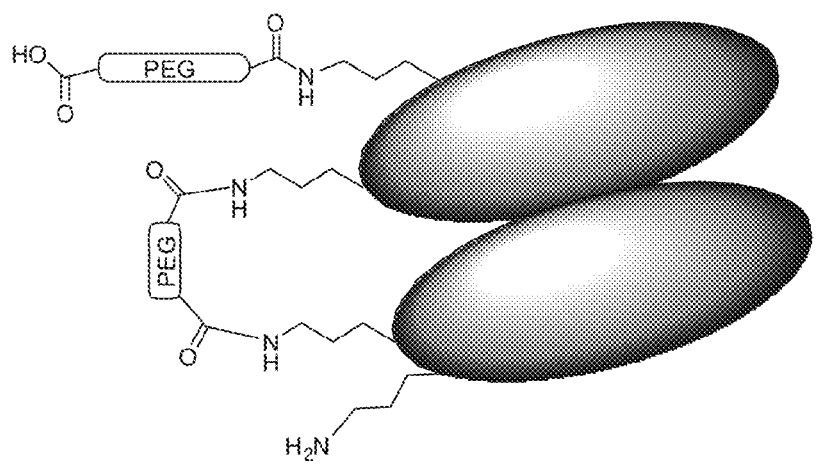
FIG. 6 is a scheme depicting a dimeric protein which has been reacted with bis-NHS-PEG cross-linking agents.

FIG. 5 shows exemplary PEG (polyethylene glycol) cross-linking agents, according to optional embodiments of the invention. FIG. 6 depicts a cross-linked α-GAL dimer according to optional embodiments of the invention.

Figure 7:
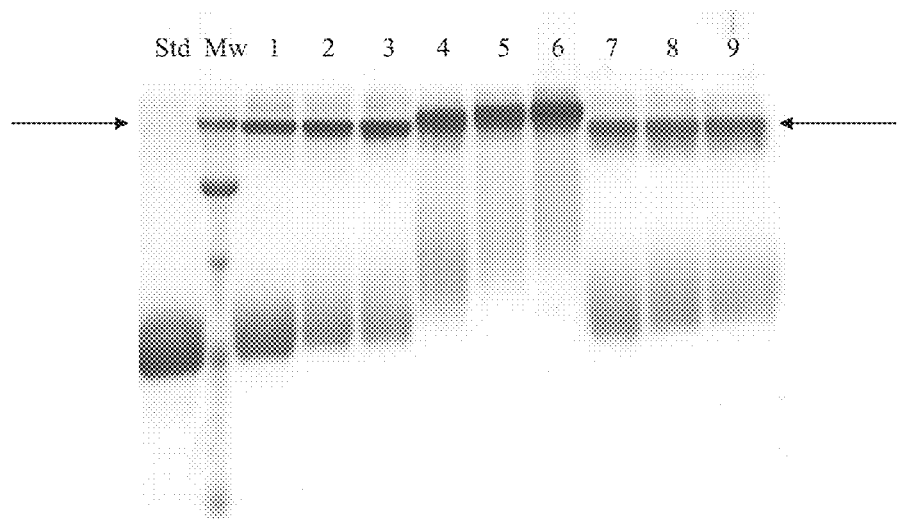
FIG. 7 presents a scan of an SDS-PAGE gel showing plant recombinant α-GAL-I which was reacted with bis-NHS-$PEG_5$ (lanes 1-3), bis-NHS-$PEG_8$ (lanes 7-9), and bis-NHS-$PEG_{45}$ (lanes 4-6), at a molar ratio of 50:1 (lanes 1, 4 and 7), 100:1 (lanes 2, 5 and 8) and 200:1 (lanes 3, 6 and 9) bis-NHS-PEG:α-GAL, as well as molecular weight markers (Mw) and non-reacted plant recombinant α-GAL-I standard (Std) (arrows show the band comprising an α-GAL dimer)

FIGS. 7-10 and 37 show that prh-α-GAL-I reacted with exemplary cross-linking agents comprising N-hydroxysuccinimide moieties. FIG. 38 shows that prh-α-GAL-I reacted with exemplary cross-linking agents comprising carboxyl groups, following in situ activation with N-hydroxysuccinimide. FIGS. 7, 37 and 38 show that the reaction with the cross-linking agent resulted in α-GAL appearing primarily in a dimeric form rather than a monomeric form under denaturing conditions, indicating that the quaternary structure of the α-GAL was maintained by covalent cross-linking. FIG. 11 shows that the cross-linked α-GAL retained its enzymatic activity.

Figure 19:
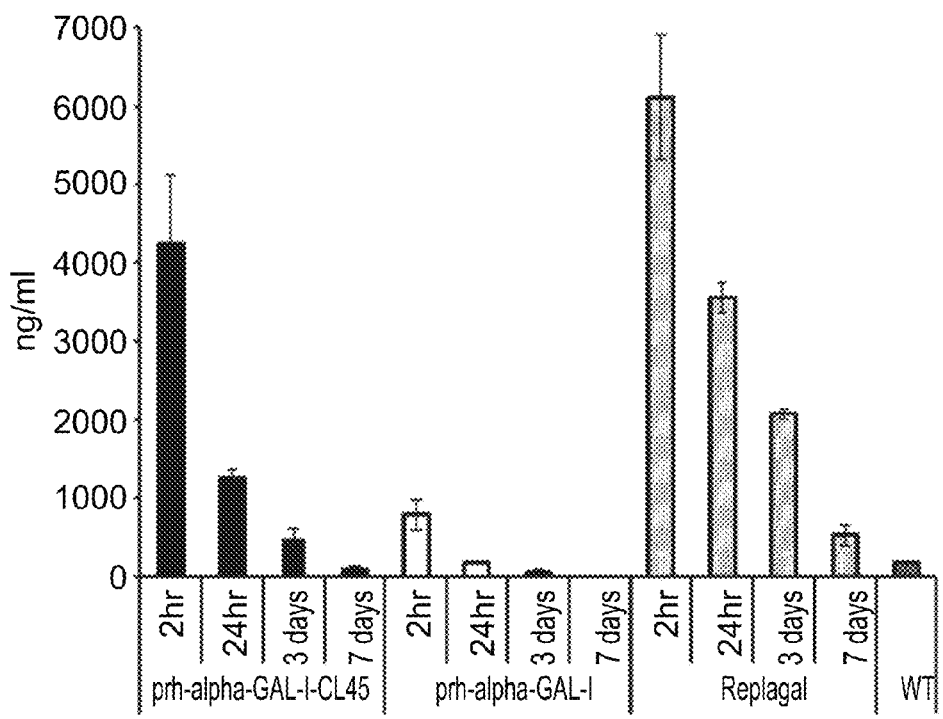
FIG. 19 is a graph showing the activity of Replagal® α-GAL and plant recombinant human α-GAL-I (prh-alpha-GAL-I), and plant recombinant human α-GAL I cross-linked with bis-NHS-PEG$_{45}$ (prh-alpha-GAL-1-CL45) in the livers of Fabry mice 2 hours, 24 hours, 3 days and 7 days following injection of α-GAL (endogenous wild type α-GAL (WT) is shown as a standard)
Figure 20:
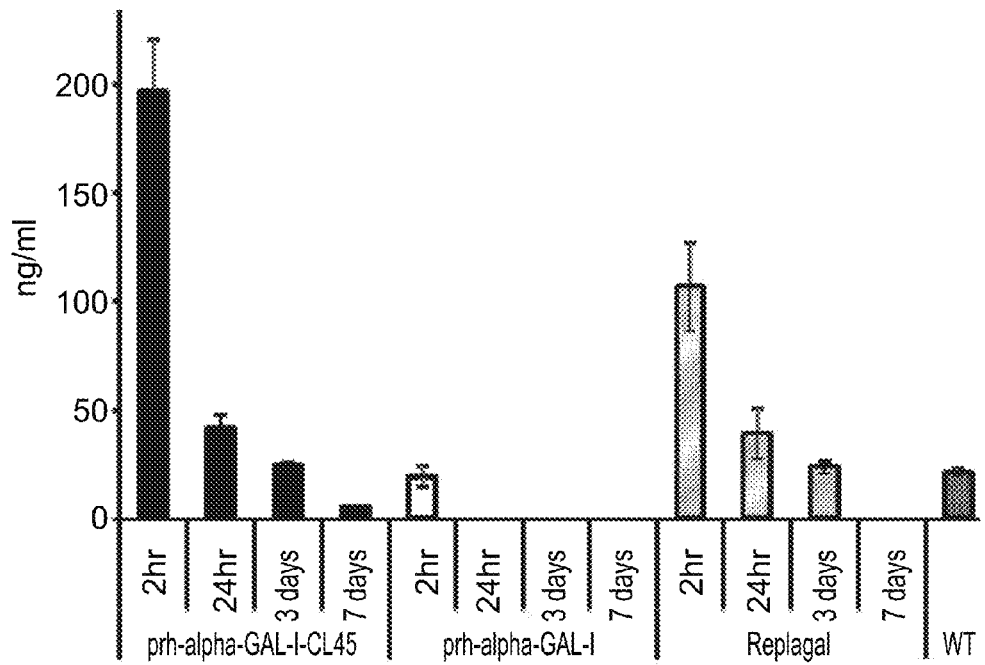
FIG. 20 is a graph showing the activity of Replagal® α-GAL and plant recombinant human α-GAL-I (prh-alpha-GAL-I), and plant recombinant human α-GAL-I cross-linked with bis-NHS-PEG$_{45}$ (prh-alpha-GAL-1-CL45) in the hearts of Fabry mice 2 hours, 24 hours, 3 days and 7 days following injection of α-GAL (endogenous wild type α-GAL (WT) is shown as a standard)
Figure 21:
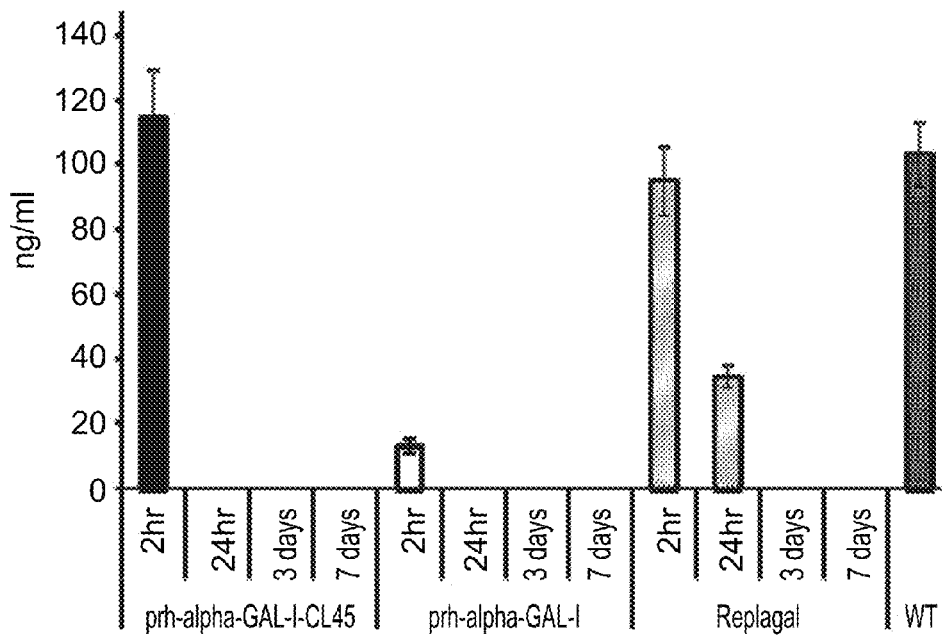
FIG. 21 is a graph showing the activity of Replagal® α-GAL and plant recombinant human α-GAL-I (prh-alpha-GAL-I), and plant recombinant human α-GAL-I cross-linked with bis-NHS-PEG$_{45}$ (prh-alpha-GAL-1-CL45) in the kidneys of Fabry mice 2 hours, 24 hours, 3 days and 7 days following injection of α-GAL (endogenous wild type α-GAL (WT) is shown as a standard)

FIGS. 12A-12C and 39 show that the cross-linked prh α-GAL-I exhibits a longer lasting activity than non-cross-linked α-GAL under simulated lysosomal conditions. The increase in stability is stronger for $PEG_{28}$ and $PEG_{45}$ linkers than for shorter PEG linkers. FIG. 13 shows that the cross-linked prh-α-GAL-I exhibits a longer lasting activity than non-cross-linked α-GAL in plasma in vivo. FIGS. 14A-21 show that cross-linked prh-α-GAL-I exhibits an enhanced activity in vivo in the spleen, liver, heart and kidneys. The enhancement of α-GAL activity is stronger for $PEG_{45}$ linkers than for shorter PEG linkers. FIGS. 15A, 15B and 19 show that although cross-linked prh-α-GAL-I exhibits an enhanced activity in vivo, the enhanced activity is not as concentrated in the liver as is Replagal® α-GAL activity.

The above results indicate that cross-linking plant recombinant human α-GAL-I results in a dimer with improved stability, which allows for a more effective increase of α-GAL activity when administered in vivo.

Similarly, FIGS. 22-28D show that cross-linking mammalian recombinant human α-GAL results in a covalently-linked dimer (FIGS. 22-24B), which exhibits normal enzymatic activity (FIG. 25), as well as longer lasting activity under both lysosomal conditions and in plama (FIGS. 26A-26B), and enhanced activity in vivo in the spleen, liver, heart and kidneys (FIGS. 27A-28D).

Similarly, FIGS. 29A-33L show that cross-linking plant recombinant human α-GAL II results in a covalently-linked dimer (FIGS. 29-30), which exhibits longer lasting activity under both lysosomal conditions and in plama (FIGS. 31A-31B), and enhanced activity in vivo in plasma and in the spleen, liver, heart and kidneys (FIGS. 32A-33L). As shown in FIGS. 33A-33L, cross-linking with a $PEG_{45}$ linker was particularly effective at enhancing in vivo activity.

These results indicate that the advantageous effects of cross-linking are applicable to a variety of α-GAL proteins.

FIGS. 34A-34C show that cross-linking α-GAL enhances parameters of α-GAL enzymatic catalysis, broadens the pH range for α-GAL activity, and allows for α-GAL activity at a pH of about 7 or more.

FIGS. 35-36B show that PEGylation without cross-linking has no significant effect on α-GAL activity, indicating that the advantageous effects of cross-linking are specifically due to cross-linking, rather than to an effect of PEGylation.

FIGS. 40-44 show that cross-linking of α-GAL according to embodiments of the invention allows for good reproducibility of the stability (FIGS. 40A-40B), degree of covalent cross-linking (FIGS. 41-43F) and enzymatic properties (FIG. 44) of the cross-linked α-GAL.

The results presented herein show that covalently cross-linked, multimeric protein structures of α-galactosidase are characterized by a higher stability and enhanced activity under physiologically relevant conditions, as compared to the native forms of α-galactosidase.

Thus, the covalently-linked multimeric protein structure may exhibit an activity which is higher than an activity of a native form of α-galactosidase, as a result of the activity of the native form decaying more rapidly over time than the activity of the cross-linked multimeric protein structure, which is stabilized by the covalent cross-linking.

The covalently cross-linked multimeric protein structure may exhibit an activity which is higher than an activity of a native form of α-galactosidase, also due to a higher initial activity (e.g., due to different parameters of activity), i.e., independently of any decay of activity over time.

Hence, according to an aspect of some embodiments of the present invention there is provided a multimeric protein structure comprising at least two α-galactosidase monomers being covalently linked to one another via a linking moiety. According to some embodiments, the multimeric protein structure features a stability higher than that of native α-galactosidase and/or an initial activity higher than that of native α-galactosidase, as described in detail below.

Herein, the term "monomer" with respect to α-galactosidase refers to an individual polypeptide of α-galactosidase. The polypeptide may include non-peptidic substituents (e.g., one or more saccharide moieties).

Herein, the term "native" with respect to α-galactosidase encompasses proteins comprising an amino acid sequence substantially identical (i.e., at least 95% homology, optionally at least 99% homology, and optionally 100%) to an amino acid sequence of a naturally occurring α-galactosidase protein. A native α-galactosidase may be a protein isolated from a natural source, or a recombinantly produced protein (e.g., derived from mammalian cells, plant cells, yeast cells, bacterial cells, insect cells).

The term "native", when used in reference to a quaternary structure of α-galactosidase (e.g., an α-galactosidase dimer), further comprises a quaternary structure substantially identical to that of a naturally occurring protein.

Herein, the phrase "naturally occurring protein" refers to a protein in a form which occurs in nature (e.g., in an organism), with respect to the protein's amino acid sequence, as well as the protein's quaternary structure if the protein is in a multimeric form.

Post-translational modifications (e.g., glycosylation) of naturally occurring α-galactosidase proteins (e.g., in an organism which expresses the naturally occurring α-galactosidase protein) may be present, absent or modified in the native form of α-galactosidase referred to herein. A native form of α-galactosidase (e.g., a recombinantly produced α-galactosidase) may optionally comprise different post-translational modifications than those of the naturally occurring α-galactosidase, provided that the native form of the α-galactosidase retains a substantially similar amino acid sequence and structure as the naturally occurring α-galactosidase, as described hereinabove.

Herein, the native form of a protein may refer to a monomeric structure (e.g., an α-galactosidase monomer) and/or a multimeric structure (e.g., an α-galactosidase dimer). For example, a dimeric protein can be described as a native form of α-galactosidase, and a monomeric polypeptide in a dimeric protein can be described as a native form of the α-galactosidase monomer.

Optionally, the multimeric protein structure described herein is a dimeric structure, as is the native form of α-galactosidase.

Alternatively, the multimeric protein structure comprises more than two α-galactosidase monomers. For example, the multimeric protein structure may be a tetramer, a hexamer, or an octamer comprised of α-galactosidase monomers.

The multimeric protein structures described herein comprise covalent bonds which link the α-galactosidase monomers therein, and which are absent from the native form of the α-galactosidase.

Optionally, the linking moiety which links the α-galactosidase monomers is a moiety which is not present in a native form of α-galactosidase (e.g., a synthetic linking moiety).

Thus, for example, the linking moiety is optionally a moiety which is covalently attached to a side chain, an N-terminus or a C-terminus, or a moiety related to post-translational modifications (e.g., a saccharide moiety) of an α-galactosidase monomer, as well as to a side chain, an N-terminus or a C-terminus, or a moiety related to post-translational modifications (e.g., a saccharide moiety) of another α-galactosidase monomer. Exemplary such linking moieties are described in detail hereinunder.

Alternatively, the linking moiety forms a part of the α-galactosidase monomers being linked (e.g., a part of a side chain, N-terminus or C-terminus, or a moiety related to post-translational modifications (e.g., a saccharide moiety) of an α-galactosidase monomer, as well as of a side chain, an N-terminus or a C-terminus, or a moiety related to post-translational modifications (e.g., a saccharide moiety) of another α-galactosidase monomer).

Thus, for example, the linking moiety can be a covalent bond (e.g., an amide bond) between a functional group of a side chain, N-terminus, C-terminus or moiety related to post-translational modifications of a monomer (e.g., an amine), and a complementary functional group of a side chain, N-terminus, C-terminus or moiety related to post-translational modifications of another monomer (e.g., carboxyl), wherein such a covalent bond is absent from the native form of the α-galactosidase. Other covalent bonds, such as, for example, an ester bond (between a hydroxy group and a carboxyl); a thioester bond; an ether bond (between two hydroxy groups); a thioether bond; an anhydride bond (between two carboxyls); a thioamide bond; a carbamate or thiocarbamate bond, are also contemplated.

Optionally, the linking moiety is devoid of a disulfide bond. However, a linking moiety which includes a disulfide bond at a position which does not form a link between monomers (e.g., cleavage of the disulfide bond does not cleave the link between the monomers) is within the scope of this embodiment of the invention. A potential advantage of linking moiety devoid of a disulfide bond is that it is not susceptible to cleavage by mildly reducing conditions, as are disulfide bonds.

Optionally, the linking moiety is a non-peptidic moiety (e.g., the linking moiety does not consist of an amide bond, an amino acid, a dipeptide, a tripeptide, an oligopeptide or a polypeptide).

Alternatively, the linking moiety may be, or may comprise, a peptidic moiety (e.g., an amino acid, a dipeptide, a tripeptide, an oligopeptide or a polypeptide).

Optionally, the linking moiety is not merely a linear extension of any of the α-galactosidase monomers attached thereto (i.e., the N-terminus and C-terminus of the peptidic moiety is not attached directly to the C-terminus or N-terminus of any of the α-galactosidase monomers).

Alternatively, the linking moiety is formed by direct covalent attachment of an N-terminus of an α-galactosidase monomer with a C-terminus of another α-galactosidase monomer, so as to produce a fused polypeptide. Such a polypeptide will not be a native form of α-galactosidase, although it may comprise two α-galactosidase monomers essentially in their native form.

However, the covalent linking of α-galactosidase monomers described herein is preferably in a form other than direct linkage of an N-terminus to a C-terminus.

The linking moiety is also referred to herein as a cross-linking moiety. The linking of α-galactosidase monomers by a linking moiety is referred to herein as "cross-linking".

The cross-linking moiety can be a covalent bond, a chemical atom or group (e.g., a C(=O)—O— group, —O—, —S—, NR—, —N=N—, —NH—C(=O)—NH—, and the like) or a bridging moiety (composed of a chain of chemical groups).

A bridging moiety can be, for example, a polymeric or oligomeric group.

The bridging moiety is a multifunctional moiety (e.g., biradical, triradical, etc.) that is attached to side chains, moieties related to post-translational modifications (e.g., saccharide moieties) and/or termini (i.e., N-termini, C-termini) of two or more of the monomers.

As exemplified herein in the Examples section, relatively short linking moieties (e.g., $PEG_2$, $PEG_4$, $PEG_5$) may be less effective than longer linking moieties (e.g., $PEG_{28}$, $PEG_{45}$) at cross-linking between different α-galactosidase monomers.

Hence, according to some embodiments, the linking moiety is not a covalent bond, a chemical atom or group, but is rather a bridging moiety.

Hence, according to some embodiments, the linking moiety is at least 10 atoms long, optionally at least 20 atoms long, optionally at least 30 atoms long, optionally at least 50 atoms long, optionally at least 100 atoms long, and optionally at least 200 atoms long.

Herein, the length of a linking moiety (when expressed as a number of atoms) refers to length of the backbone of the linking moiety, i.e., the number atoms forming a linear chain between residues of each of two monomers linked via the linking moiety.

Optionally, the linking moiety is below a certain size, so as to avoid an unnecessarily excessive part of the linking moiety in the formed cross-linked protein, which may interfere with the function of the protein.

Hence, according to some embodiments, each linking moiety is characterized by a molecular weight of less than 20 KDa, optionally less than 10 KDa, optionally less than 5 KDa, and optionally less than 3 KDa.

In order to facilitate cross-linking, the linking moiety is optionally substantially flexible, wherein the bonds in the backbone of the linking moiety are mostly rotationally free, for example, single bonds which are not coupled to a double bond (e.g., unlike an amide bond) and wherein rotation is not sterically hindered. Optionally, at least 70%, optionally at least 80%, and optionally at least 90% (e.g., 100%) of the bonds in the backbone of the linking moiety are rotationally free.

In some embodiments, the linking moiety comprises a poly(alkylene glycol) chain.

The phrase "poly(alkylene glycol)", as used herein, encompasses a family of polyether polymers which share the following general formula: —O—[$(CH_2)_m$—O—]$_n$—, wherein m represents the number of methylene groups present in each alkylene glycol unit, and n represents the number of repeating units, and therefore represents the size or length of the polymer. For example, when m=2, the polymer is referred to as a polyethylene glycol, and when m=3, the polymer is referred to as a polypropylene glycol.

In some embodiments, m is an integer greater than 1 (e.g., m=2, 3, 4, etc.).

Optionally, m varies among the units of the poly(alkylene glycol) chain. For example, a poly(alkylene glycol) chain may comprise both ethylene glycol (m=2) and propylene glycol (m=3) units linked together.

The poly(alkylene glycol) optionally comprises at least two functional groups (e.g., as described herein), each functional group forming a covalent bond with one of the α-galactosidase monomers. The functional groups are optionally terminal groups of the poly(alkylene glycol), such that the entire length of the poly(alkylene glycol) lies between the two functional groups.

The phrase "poly(alkylene glycol)" also encompasses analogs thereof, in which the oxygen atom is replaced by another heteroatom such as, for example, S, —NH— and the like. This term further encompasses derivatives of the above, in which one or more of the methylene groups composing the polymer are substituted. Exemplary substituents on the methylene groups include, but are not limited to, alkyl, cycloalkyl, alkenyl, alkynyl, alkoxy, hydroxy, oxo, thiol and thioalkoxy, and the like.

The phrase "alkylene glycol unit", as used herein, encompasses a —$(CH_2)_m$—O— group or an analog thereof, as described hereinabove, which forms the backbone chain of the poly(alkylene glycol), wherein the $(CH_2)_m$ (or analog thereof) is bound to a heteroatom belonging to another alkylene glycol unit or to an α-galactosidase monomer moiety (in cases of a terminal unit), and the O (or heteroatom analog thereof) is bound to the $(CH_2)_m$ (or analog thereof) of another alkylene glycol unit, or to a functional group which forms a bond with an α-galactosidase monomer.

An alkylene glycol unit may be branched, such that it is linked to 3 or more neighboring alkylene glycol units, wherein each of the 3 or more neighboring alkylene glycol units are part of a poly(alkylene glycol) chain. Such a branched alkylene glycol unit is linked via the heteroatom thereof to one neighboring alkylene glycol unit, and heteroatoms of the remaining neighboring alkylene glycol units are each linked to a carbon atom of the branched alkylene glycol unit. In addition, a heteroatom (e.g., nitrogen) may bind more than one carbon atom of an alkylene glycol unit of which it is part, thereby forming a branched alkylene glycol unit (e.g., [—$(CH_2)_m$]$_2$N— and the like).

In exemplary embodiments, at least 50% of alkylene glycol units are identical, e.g., they comprise the same heteroatoms and the same m values as one another. Optionally, at least 70%, optionally at least 90%, and optionally 100% of the alkylene glycol units are identical. In exemplary embodiments, the heteroatoms bound to the identical alkylene glycol units are oxygen atoms. In further exemplary embodiments, m is 2 for the identical units.

In one embodiment, the linker is a single, straight chain linker, preferably being polyethylene glycol (PEG).

As used herein, the term "poly(ethylene glycol)" describes a poly(alkylene glycol), as defined hereinabove, wherein at least 50%, at least 70%, at least 90%, and preferably 100%, of the alkylene glycol units are —$CH_2CH_2$—O—. Similarly, the phrase "ethylene glycol units" is defined herein as units of —$CH_2CH_2O$—.

According to optional embodiments, the linking moiety comprises a poly(ethylene glycol) or analog thereof, having a general formula:

wherein each of $X_1$ and $X_2$ is a functional group (e.g., as described herein) that forms a covalent bond with at least one α-galactosidase monomer;

Y is O, S or $NR_5$ (optionally O);

n is an integer, optionally from 1 to 200 (optionally from 5 to 150, and optionally from 40 to 70), although higher values of n are also contemplated; and each of $R_1$, $R_2$, $R_3$, $R_4$, and $R_5$ is independently selected from the group consisting of hydrogen, alkyl, cycloalkyl, alkenyl, alkynyl, alkoxy, hydroxy, oxo, thiol and thioalkoxy.

In some embodiments, n is at least 5, optionally at least 8, optionally at least 15, optionally at least 25, and optionally at least 40.

In some embodiments, n is no more than 200, optionally no more than 150, and optionally no more than 70.

The poly(ethylene glycol) or analog thereof may optionally comprise a copolymer, for example, wherein the $CR_1R_2$—$CR_3R_4$—Y units in the above formula are not all identical to one another.

In some embodiments, at least 50% of $CR_1R_2$—$CR_3R_4$—Y units are identical. Optionally, at least 70%, optionally at least 90%, and optionally 100% of the $CR_1R_2$—$CR_3R_4$—Y units are identical.

Optionally, the linking moiety is branched, for example, such that for one or more $CR_1R_2$—$CR_3R_4$—Y units in the above formula, at least of one of $R_1$, $R_2$, $R_3$, $R_4$, and $R_5$ is —$(CR_1R_2$—$CR_3R_4$—$Y)_p$—$X_3$—, wherein $R_1$-$R_4$ and Y are as defined hereinabove, p is an integer as defined herein for n (e.g., from 1 to 200), and $X_3$ is as defined herein for $X_1$ and $X_2$.

The functional groups may optionally form a bond such as, but not limited to, an amide bond, an amide bond, an ester bond, and/or an ether bond.

For example, the functional group may optionally comprise a carbonyl group which forms an amide bond with a nitrogen atom in a polypeptide (e.g., in a lysine residue or N-terminus), or an ester bond with an oxygen atom in a polypeptide (e.g., in a serine, threonine or tyrosine residue).

Alternatively or additionally, the functional group may optionally comprise a heteroatom (e.g., N, S, O) which forms an amide bond, ester bond or thioester bond with a carbonyl group in a polypeptide (e.g., in a glutamate or aspartate residue or in a C-terminus).

Alternative or additionally, the functional group may comprise an alkyl or aryl group attached to a polypeptide (e.g., to a heteroatom in the polypeptide).

Alternatively or additionally, the functional group may optionally comprise a nitrogen atom which forms an amine bond with an alkyl group in an α-galactosidase monomer, or an α-galactosidase monomer may optionally comprise a nitrogen atom which forms an amine bond with an alkyl group in the functional group. Such an amine bond may be formed by reductive amination (e.g., as described hereinbelow).

In some embodiments, at least one of the functional groups forms an amide bond with a polypeptide (e.g., with a lysine residue therein).

The functional groups may be identical to one another or different.

In some embodiments, at least one of the functional groups is attached to one functionality of a polypeptide (e.g., an amine group of a lysine residue or N-terminus), and at least one of the functional groups is attached to a different functionality of a polypeptide (e.g., a thiol group of a cysteine residue).

According to optional embodiments, the multimeric protein structure described herein exhibits a high stability in human plasma conditions and/or in lysosomal conditions.

As used herein, the phrase "human plasma conditions" refers to human plasma as a medium, at a temperature of 37° C.

As used herein, the phrase "lysosomal conditions" refers to an aqueous solution having a pH of 4.6 as a medium (e.g., a citrate phosphate buffer described herein), at a temperature of 37° C.

Enhanced stability under lysosomal conditions is advantageous because the lysosome is a target for replacement therapy for α-galactosidase, as lysosomes are the normal location for α-galactosidase activity in a body, and lysosomal conditions (e.g., acidic pH) represent optimal conditions for activity of α-galactosidase.

Without being bound by any particular theory, it is believed that enhanced stability in serum-like conditions (e.g., the human plasma conditions described herein) is also advantageous because stable α-galactosidase in the blood can act on metabolites (e.g., $Gb_3$) present in the blood due to efflux from cells. A serum-active multimeric protein structure could optionally be efficient in removing and preventing glycosphinglipids deposited within blood vessel walls which promote inflammation [Bodary et al., TCM 17(4):129-133]. For example, in Fabry disease, the major pathogenesis results from the accumulation of $Gb_3$ in the vascular endothelium, leading to vascular occlusion of small vessels, ischemia and infarction of these vessels and ischemia and infarction of the kidney, heart and brain [Desnick et al., 2003, Annals of Internal Medicine, 138(4):338-346]. Additionally, enhanced stability in serum can negate the need for lysosomal trafficking. ERT can thereby become much more accessible, as robust cost-effective host systems e.g., plants, can be employed.

According to optional embodiments, the high stability of the multimeric protein structure in human plasma conditions is such that the multimeric protein structure exhibits, upon being subjected to human plasma conditions for one hour, an α-galactosidase activity which is at least 10% higher, optionally 20% higher, optionally 50% higher, and optionally 100% higher, than an α-galactosidase activity of native α-galactosidase upon subjecting the native α-galactosidase to the human plasma conditions for one hour.

Alternatively or additionally, the high stability of the multimeric protein structure in human plasma conditions is such that an α-galactosidase activity of the multimeric protein structure decreases more slowly in human plasma conditions than a corresponding activity of the native α-galactosidase. Optionally, the multimeric protein structure exhibits an activity which decreases upon subjecting the protein structure to human plasma conditions for one hour by a percentage which is at least 10% less, optionally 20% less, optionally 50% less, and optionally 80% less, than the percentage by which a corresponding activity of the native α-galactosidase decreases upon subjecting the native α-galactosidase to human plasma conditions for one hour.

It is to be understood that herein, a decrease which is "10% less" than a decrease of 50% refers to a decrease of 45% (45 being 10% less than 50), and not to a decrease of 40% (50%-10%).

Alternatively or additionally, the high stability of the multimeric protein structure in human plasma conditions is such that an α-galactosidase activity of the multimeric protein structure remains substantially unchanged upon subjecting the multimeric protein structure to human plasma conditions for one hour, and optionally for 2, 4 or even 6 hours.

As used herein, the phrase "substantially unchanged" refers to a level (e.g., of activity) which remains in a range of from 50% to 150% of the initial level, and optionally a level which remains at least 60%, optionally at least 70%, optionally at least 80%, and optionally at least 90% of the initial level.

Optionally, the high stability of the multimeric protein structure in lysosomal conditions is such that the multimeric protein structure exhibits, upon being subjected to lysosomal conditions for a predetermined time period (e.g., one day, two days, 3 days, one week), an α-galactosidase activity which is at least 10% higher, optionally 20% higher, optionally 50% higher, and optionally 100% higher, than an activity of native α-galactosidase upon subjecting the native α-galactosidase to the lysosomal conditions for the same predetermined time period.

Alternatively or additionally, the high stability of the multimeric protein structure in lysosomal conditions is such that an α-galactosidase activity of the multimeric protein structure decreases more slowly in lysosomal conditions than a corresponding activity of the native α-galactosidase. Optionally, the multimeric protein structure exhibits an activity which decreases upon subjecting the protein structure to lysosomal conditions for a predetermined time period (e.g., one day, 2 days, 3 days, one week), by a percentage which is at least 10% less, optionally 20% less, optionally 50% less, and optionally 80% less, than the percentage by which a corresponding activity of the native α-galactosidase decreases upon subjecting the native α-galactosidase to lysosomal conditions for the same time period.

Alternatively or additionally, the high stability of the multimeric protein structure in lysosomal conditions is such that an α-galactosidase activity of the multimeric protein structure remains substantially unchanged upon subjecting the multimeric protein structure to lysosomal conditions for one day, for 2 days, for 3 days, for one week, for two weeks, and/or for one month.

As exemplified in the Examples section herein, in addition to exhibiting more stability over time, the multimeric protein structure may exhibit parameters of α-galactosidase activity which are different than those of the native α-galactosidase.

Hence, according to optional embodiments, the multimeric protein structure is characterized as exhibiting, independently of any decay of activity over time, an α-galactosidase activity which is higher than an α-galactosidase activity of a native form of the protein. Optionally, the activity is 10% higher, and optionally 20% higher, than the corresponding activity of the native form.

In order to characterize such an activity, the activity is preferably determined immediately (e.g., within 1 hour, within 15 minutes) upon subjecting the native α-galactosidase or multimeric protein structure to conditions (e.g., as described herein) in which the activity decreases substantially, so that the measured activity will reflect the activity per se, and not a degree of stability.

Optionally, the multimeric protein structure is characterized as exhibiting an α-galactosidase activity in lysosomal conditions which is higher than a corresponding activity of native α-galactosidase.

Alternatively or additionally, the multimeric protein structure is characterized as exhibiting an α-galactosidase activity in simulated physiological conditions at a neutral pH which is higher than a corresponding activity of native α-galactosidase. The simulated physiological conditions comprise an aqueous solution (e.g., phosphate buffer saline) at a temperature of 37° C. The pH is optionally 7. Alternatively, the pH is 7.4.

The α-galactosidase activity described herein is a biological activity which is characteristic of α-galactosidase (e.g., a catalytic activity characteristic of α-galactosidase, such as hydrolysis of a terminal α-galactosyl moiety of a substrate).

In some embodiments, a catalytic activity of α-galactosidase is characterized by a rate of catalysis at saturation (i.e., a $V_{max}$ value).

Alternatively, the α-galactosidase activity is a therapeutic activity (e.g., an enzymatic activity having a therapeutic effect), such as a therapeutic activity in the context of Fabry disease. Optionally, the therapeutic activity is determined in experimental animals (e.g., Fabry mice), and optionally in human Fabry patients.

Techniques for determining an activity of α-galactosidase will be known to a skilled person. Typically, the α-galactosidase (i.e., the native form or a multimeric protein structure described herein) is contacted with a compound recognized in the art as a substrate of α-galactosidase, and the degree of activity is then determined quantitatively. Compounds which allow for particularly convenient detection of α-galactosidase activity are known in the art and are commercially available.

In some embodiments, α-galactosidase activity is determined by assaying hydrolysis of 4-methylumbelliferyl-α-D-galactopyranoside (e.g., as described in the Examples section herein).

In some embodiments, α-galactosidase activity is determined by assaying hydrolysis of p-nitrophenyl-α-D-galactopyranoside (e.g., as described in the Examples section herein).

When comparing an activity of a multimeric protein structure described herein with an activity of native α-galactosidase, the native α-galactosidase preferably comprises α-galactosidase monomers substantially identical (e.g., with respect to amino acid sequence and glycosylation pattern) to the α-galactosidase monomers of the multimeric structure.

According to some embodiments, the multimeric protein structure is characterized by a circulating half-life in a physiological system (e.g., blood, serum and/or plasma of a human or laboratory animal) which is higher (e.g., at least 20%, at least 50% higher, at least 100% higher, at least 400% higher, at least 900% higher) than a circulating half-life of native α-galactosidase.

An increased circulating half-life may optionally be associated with a higher in vitro stability (e.g., as described herein), a higher in vivo stability (e.g., resistance to metabolism) and/or with other factors (e.g., reduced renal clearance).

Circulating half-lives can be determined by taking samples (e.g., blood samples, tissue samples) from physiological systems (e.g., humans, laboratory animals) at various intervals, and determining a level of α-galactosidase in the sample, using techniques known in the art.

Optionally, the half-life is calculated as a terminal half-life (e.g., as described in the Examples section), wherein half-life is the time required for a concentration (e.g., a blood concentration) to decrease by 50% after pseudo-equilibrium of distribution has been reached. The terminal half-life may be calculated from a terminal linear portion of a time vs. log concentration, by linear regression of time vs. log concentration (see, for example, Toutain & Bousquet-Melou [*J Vet Pharmacol Ther* 2004, 27:427-39]). Thus, the terminal half-life is a measure of the decrease in drug plasma concentration due to drug elimination and not of decreases due to other reasons, and is not necessarily the time necessary for the amount of the administered drug to fall by one half.

Determining a level of α-galactosidase (e.g., the multimeric protein structure or the native α-galactosidase) may comprise detecting the physical presence of α-galactosidase (e.g., via an antibody against α-galactosidase) and/or detecting a level of an α-galactosidase activity (e.g., as described herein).

According to some embodiments, the multimeric protein structure is characterized by an α-galactosidase activity in an organ (e.g., spleen, heart, kidney, brain, liver) upon administration (e.g., intravenous administration) of the protein structure to a vertebrate (e.g., a human, a mouse), for example, a vertebrate with an α-galactosidase deficiency (e.g., a human Fabry disease patient, a Fabry mouse). Optionally, the α-galactosidase activity in the organ is higher than an α-galactosidase activity of native α-galactosidase in the organ, upon an equivalent administration to a vertebrate.

The activity in an organ may be a function of uptake of the α-galactosidase and/or retention of α-galactosidase activity following uptake.

Optionally, α-galactosidase activity in the organ is determined 2 hours after administration, and optionally 24 hours, optionally 3 days, optionally 7 days, and optionally 14 days, after administration.

As increased activity of α-galactosidase in a liver may in some cases be associated with a lower activity in other parts of a body, and hence, with a reduced biological effect of the α-galactosidase.

Hence, in some embodiments, the multimeric protein structure is characterized by an enhanced α-galactosidase activity in an organ other than a liver. Exemplary organs include the spleen, heart and kidneys.

In some embodiments, the multimeric protein structure is characterized by an enhanced α-galactosidase activity in an organ after administration (as described herein) which is at least 20% higher, optionally at least 50% higher, optionally at least 100% higher, and optionally at least 300% higher, than the activity of native α-galactosidase after an equivalent administration. As noted hereinabove, the present inventors have devised and successfully prepared and practiced stabilized forms of α-galactosidase by means of multimeric structures of cross-linked α-galactosidase monomers.

Optionally, the α-galactosidase is a human α-galactosidase (e.g., a recombinant human α-galactosidase), for example, in order to facilitate optimal biocompatibility for administration to human subjects. Human α-galactosidase is commercially available, for example, as Replagal® (agalsidase alpha, Shire) and Fabrazyme® (agalsidase beta, Genzyme).

Herein, "human α-galactosidase" refers to an α-galactosidase comprising an amino acid sequence substantially identical (e.g., as described hereinabove) to an amino acid sequence of an α-galactosidase protein which naturally occurs in humans.

In some embodiments, the α-galactosidase is a plant recombinant α-galactosidase. Exemplary α-galactosidases include plant recombinant human α-galactosidases.

Examples of α-GAL include, without limitation, α-GAL having an amino acid sequence selected from the group consisting of SEQ ID NO: 1, SEQ ID NO: 2, and SEQ ID NO: 3. Optionally, the α-GAL has an amino acid sequence selected from the group consisting of SEQ ID NO: 2 and SEQ ID NO: 3.

As used herein, "α-galactosidase" refers to any protein which exhibits an enzymatic activity (e.g., hydrolysis) towards galactose moieties in $Gb_3$ (e.g., α-galactosidase A). Optionally, "α-galactosidase" refers to E.C. 3.2.1.22.

The α-galactosidase of embodiments of the invention can be purified (e.g., from plants or animal tissue) or generated by recombinant DNA technology.

As described herein, activity of α-galactosidase in serum may be highly advantageous, for example, for reducing $Gb_3$ levels in serum.

Hence, in some embodiments, the α-galactosidase is an alkaline α-galactosidase.

As used herein the phrase "alkaline α-galactosidase" refers to α-GAL characterized by an ability to hydrolyse terminal-linked α-galactose moieties from galactose-containing oligosaccharides under neutral to basic pH conditions (e.g., about pH 7-7.5), particularly at a normal serum pH (e.g., about 7.35-7.45).

It will be appreciated that an alkaline α-GAL of some embodiments of the invention may be active under neutral to basic pH conditions but may still display activity under acidic pH conditions (i.e., about 4.6).

In a specific embodiment the enzyme is active under acidic to basic pH conditions (i.e., about pH 4.2-7.5).

In yet another specific embodiment the enzyme is active under pH of about 6.5-7.5.

Specific examples of alkaline α-galactosidases which can be used in accordance with the present teachings are provided in US Patent Application 20070036883, WO03/097791, and in PCT/IL2010/000956, each of which is hereby incorporated by reference in its entirety.

Thus, alkaline α-galactosidase can be a member of the plant family selected from the group consisting of Cucurbitaceae, Lamiaceae, Piperaceae, Solanaceae, Leguminosae, Cruciferae and Gramineae families.

According to a specific embodiment, the alkaline α-galactosidase is from melon.

P.-R. Gaudreault and J. A. Webb have described in several publications, (such as "Alkaline alpha-galactosidase in leaves of *Cucurbita* pepo", Plant Sci. Lett. 24, 281-288, 1982, "Partial purification and properties of an alkaline alpha-galactosidase from mature leaves of *Cucurbita* pepo", Plant Physiol., 71, 662-668, 1983, and "Alkaline alpha-galactosidase activity and galactose metabolism in the family Cucurbitaceae", Plant Science, 45, 71-75, 1986), a novel α-galactosidase purified from young leaves of *Cucurbita* pepo, that has an optimal activity at alkaline conditions (pH 7.5). In addition to the alkaline α-galactosidase, they also reported three acid forms of the enzyme, and distinct substrate preferences were found for the acid and alkaline forms α-Galactosidase activity at alkaline pH has been observed in other cucurbit tissue, such as cucumber fruit pedicels, young squash fruit and young melon fruit ("Melons: Biochemical and Physiological Control of Sugar Accumulation", In: Encyclopedia of Agricultural Science, vol. 3, pp. 25-37, Arntzen, C. J., et al., eds. Academic Press, New York, 1994).

Bachmann et al. ("Metabolism of the raffinose family oligosaccharides in leaves of *Ajuga reptens* L.", Plant Physiology 105:1335-1345, 1994) that *Ajuga reptens* plants (common bugle), a stachyose translocator from the unrelated Lamiaceae family also contains an alkaline α-galactosidase. This enzyme was partially characterized and found to have high affinity to stachyose. Also, leaves of the *Peperomia camptotricha* L. plant, from the family Piperaceae, show α-galactosidase activity at alkaline pH, suggesting that they also contain an alkaline α-galactosidase enzyme (Madore, M., "Catabolism of raffinose family oligosaccharides by vegetative sink tissues", In: Carbon Partitioning and Source-Sink Interactions in Plants, Madore, M. and Lucas, W. J. (eds.) pp. 204-214, 1995, American Society of Plant Physiologists, Maryland). Similarly, Gao and Schaffer (Plant Physiol. 1999; 119:979-88, which is incorporated fully herein by reference) have reported an α-galactosidase activity with alkaline pH optimum in crude extracts of tissues from a variety of species including members of the Cucurbit and Coleus (Lamiaceae) families.

Specific examples of plant alkaline α-galactosidase sequences are provided in SEQ ID NOs: 4, 5 and 13 (*Cucumis melo*), 6 (*T. tetragonioides*), 7 and 12 (*Cucumis sativus*), 8 and 9 (*Zea mays*), 10 (*Oruza sativa*), 11 (*Pisum sativum*) and 14 (*Coffea arabica*).

In some embodiments, the α-galactosidase is an acid α-galactosidase.

As used herein, "acid α-galactosidase" refers to α-galactosidase characterized by an ability to hydrolyse terminal-linked α-galactose moieties from galactose-containing oligosaccharides under acidic pH conditions (e.g., about pH 4.2-5), such as occur in a lysosome.

The α-galactosidase of embodiments of the invention can be of any human, animal or plant source, provided no excessively adverse immunological reaction is induced upon in vivo administration (e.g., plant to human).

To reduce immunological reaction, a non-human α-galactosidase preparation (e.g., of plant α-galactosidase) can be co-administered with a human α-galactosidase (i.e., acid human α-galactosidase).

Optionally, the multimeric protein structure further comprises at least one mannose-6-phosphate (M6P) moiety. The M6P moiety (or moieties) may be linked to one or more of the α-galactosidase monomers of the multimeric protein structure (e.g., via a linker).

Techniques and reagents for introducing M6P-containing moieties to a biomolecule (e.g., a polypeptide) are described in WO 2009/024977.

As exemplified in the Examples section herein, a multimeric protein structure described herein may be conveniently prepared by reacting α-galactosidase with a cross-linking agent.

Hence, according to another aspect of embodiments of the invention, there is provided a process of preparing a multimeric protein structure described herein. The process comprises reacting α-galactosidase, so as to introduce at least one linking moiety which covalently links at least two α-galactosidase monomers.

Optionally, the linking moiety is a bond (e.g., an amide bond, a disulfide bond) which links one α-galactosidase monomer to another α-galactosidase monomer. Optionally, the bond is introduced by using suitable conditions and/or reagents. For example, reagents which are suitable for forming an amide bond from a carboxylic acid group and an amine group are known in the art.

Optionally, the linking moiety is a moiety which is not derived from a part of the α-galactosidase. For example, the linking moiety may be an oligomer, a polymer, a residue of a small molecule (e.g., an amino acid).

In some embodiments, the linking moiety is introduced by reacting the α-galactosidase with a cross-linking agent which comprises the linking moiety (e.g., as described herein) and at least two reactive groups.

Optionally, the α-galactosidase is reacted under conditions in which the native α-galactosidase is in a dimeric form.

In some embodiments, the cross-linking agent is reacted with the α-galactosidase at a molar ratio in a range of from 5:1 to 500:1 (cross-linking agent: α-galactosidase monomer), optionally in a range of from 50:1 to 400:1, and optionally in a range of from 75:1 to 300:1 (e.g., about 100:1, about 200:1).

The process optionally further comprises purifying the cross-linked protein, for example, removing excess cross-linking agent. Common purification methods may be used, such as dialysis and/or ultra-filtration using appropriate cut-off membranes and/or additional chromatographic steps, including size exclusion chromatography, ion exchange chromatography, affinity chromatography, hydrophobic interaction chromatography, and the like.

The reactive group is selected suitable for undergoing a chemical reaction that leads to a bond formation with a complementary functionality in the α-galactosidase monomer. Optionally, each reactive group is capable of forming a covalent bond between the linking moiety described herein and at least one polypeptide (e.g., so as to form a functional group bound to the polypeptide, as described herein).

The reactive groups of a cross-linking agent may be identical to one another or different.

As used herein, the phrase "reactive group" describes a chemical group that is capable of undergoing a chemical reaction that typically leads to a bond formation. The bond, according to the present embodiments, is preferably a covalent bond (e.g., for each of the reactive groups). Chemical reactions that lead to a bond formation include, for example, nucleophilic and electrophilic substitutions, nucleophilic and electrophilic addition reactions, alkylations, addition-elimination reactions, cycloaddition reactions, rearrangement reactions and any other known organic reactions that involve a functional group, as well as combinations thereof.

The reactive group may optionally comprise a non-reactive portion (e.g., an alkyl) which may serve, for example, to attach a reactive portion of the reactive group to a linking moiety (e.g., poly(alkylene glycol) or analog thereof) described herein.

The reactive group is preferably selected so as to enable its conjugation to α-galactosidase. Exemplary reactive groups include, but are not limited to, carboxylate (e.g., —CO$_2$H), thiol (—SH), amine (—NH$_2$), halo, azide (—N$_3$), isocyanate (—NCO), isothiocyanate (—N═C═S), hydroxy (—OH), carbonyl (e.g., aldehyde), maleimide, sulfate, phosphate, sulfonyl (e.g. mesyl, tosyl), etc. as well as activated groups, such as N-hydroxysuccinimide (NHS) (e.g. NHS esters), sulfo-N-hydroxysuccinimide, anhydride, acyl halide (—C(═O)-halogen) etc.

In some embodiments, the reactive group comprises a leaving group, such as a leaving group susceptible to nucleophilic substitution (e.g., halo, sulfate, phosphate, carboxylate, N-hydroxysuccinimide).

Optionally, the reactive group may be in an activated form thereof.

As used herein, the phrase "activated form" describes a derivative of a chemical group (e.g., a reactive group) which is more reactive than the chemical group, and which is thus readily capable of undergoing a chemical reaction that leads to a bond formation. The activated form may comprise a particularly suitable leaving group, thereby facilitating substitution reactions. For example, a —C(═O)—NHS group (N-hydroxysuccinimide ester, or —C(═O)—O-succinimide) is a well-known activated form of —C(═O)OH, as NHS (N-hydroxysuccinimide) can be reacted with a —C(═O)OH to form —C(═O)—NHS, which readily reacts to form products characteristic of reactions involving —C(═O)OH groups, such as amides and esters.

The reactive group can be attached to the rest of the linking moiety (e.g., a poly(alkylene glycol) or analog thereof) via different groups, atoms or bonds. These may include an ether bond [e.g., —O-alkyl-], an ester bond [e.g., —O—C(═O)-alkyl-], a carbamate [e.g., O—C(═O)—NH-alkyl-], etc. Thus, a variety of terminal groups can be employed.

The following are non-limiting examples of the different groups that may constitute a reactive group as described herein: —CH$_2$CO$_2$H, —CH$_2$CH$_2$CO$_2$H, —CH$_2$CH$_2$SH, —CH$_2$CH$_2$NH$_2$, —CH$_2$CH$_2$N$_3$, —CH$_2$CH$_2$NCO, —CH$_2$—C(═O)—NHS, —CH$_2$CH$_2$—C(═O)—NHS, —C(═O)—CH$_2$—C(═O)—NHS, —CH$_2$CH$_2$—NHC(═O)CH$_2$CH$_2$-maleimide, etc.

The number of methylene groups in each of the above reactive groups is merely exemplary, and may be varied.

The reactive group may also comprise the heteroatom at the end of a poly(alkylene glycol) chain (e.g., —OH).

In exemplary embodiments of the present invention, the reactive group comprises a carboxylate (e.g., an activated carboxylate such as an N-hydroxysuccinimide ester).

Optionally, the reactive group reacts with an amine group in the α-galactosidase (e.g., in a lysine residue and/or an N-terminus) to form an amide bond.

In some embodiments, the reaction of the reactive group comprises reductive amination, wherein an amine group reacts with an aldehyde group to form an imine, and the imine is reduced (e.g., by addition of a reducing agent, such as sodium cyanoborohydride) to form an amine bond. The reactive group may be an amine group which reacts with an aldehyde group of the α-galactosidase (e.g., on a saccharide moiety attached to the polypeptide of the protein), or the reactive group may be an aldehyde group which reacts with an amine group of the α-galactosidase (e.g., on a lysine residue). Optionally, a saccharide moiety of α-galactosidase is oxidized by an oxidizing agent to form an aldehyde group, prior to reaction of the reactive group with the α-galactosidase. For example, reaction of a saccharide with sodium periodate may be used to produce a pair of aldehyde groups in a saccharide moiety.

In some embodiments, at least one of the reactive groups is selected so as to react with one functionality of an α-galactosidase monomer (e.g., an amine group of a lysine residue or N-terminus), and at least one of the reactive groups is selected so as to react with a different functionality of an α-galactosidase monomer (e.g., a thiol group of a cysteine residue).

Optionally, one or more polypeptides described herein are reacted with a glycosylation reagent for introducing one or more M6P moieties, in order to obtain an M6P-containing multimeric protein structure (e.g., as described herein). Suitable M6P-containing glycosylation reagents and their use are described, for example, in WO 2009/024977.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, and amino, as these terms are defined herein. Representative examples are piperidine, piperazine, tetrahydrofuran, tetrahydropyran, morpholine and the like.

A "hydroxy" group refers to an —OH group.

An "azide" group refers to a —N=N$^+$=N$^-$ group.

An "alkoxy" group refers to both an —O-alkyl and an —O-cycloalkyl group, as defined herein.

An "aryloxy" group refers to both an —O-aryl and an —O-heteroaryl group, as defined herein.

An "ether" refers to both an alkoxy and an aryloxy group, wherein the group is linked to an alkyl, alkenyl, alkynyl, cycloalkyl, aryl, heteroaryl or heteroalicyclic group.

An ether bond describes a —O— bond.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "thioether" refers to both a thioalkoxy and a thioaryloxy group, wherein the group is linked to an alkyl, alkenyl, alkynyl, cycloalkyl, aryl, heteroaryl or heteroalicyclic group.

A thioether bond describes a —S— bond.

A "disulfide" group refers to both a —S-thioalkoxy and a —S-thioaryloxy group. A disulfide bond describes a —S—S— bond.

A "carbonyl" group refers to a —C(=O)—R' group, where R' is defined as hereinabove.

A "thiocarbonyl" group refers to a —C(=S)—R' group, where R' is as defined herein.

A "carboxyl" refers to both "C-carboxy" and O-carboxy".

A "C-carboxy" group refers to a —C(=O)—O—R' groups, where R' is as defined herein.

An "O-carboxy" group refers to an R'C(=O)—O— group, where R' is as defined herein.

An "oxo" group refers to a =O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(=S)—O—R' and —O—C(=S)R' groups.

An "ester" refers to a C-carboxy group wherein R' is not hydrogen.

An ester bond refers to a —O—C(=O)— bond.

A thioester bond refers to a —O—C(=S)— bond or to a —S—C(=O) bond.

A "halo" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both S-sulfonamido and N-sulfonamido groups, as defined herein.

An "S-sulfonamido" group refers to a —S(=O)$_2$—NR'R" group, with each of R' and R" as defined herein.

An "N-sulfonamido" group refers to an R'S(=O)$_2$—NR" group, where each of R' and R" is as defined herein.

An "O-carbamyl" group refers to an —OC(=O)—NR'R" group, where each of R' and R" is as defined herein.

An "N-carbamyl" group refers to an R'OC(=O)—NR"— group, where each of R' and R" is as defined herein.

A "carbamyl" or "carbamate" group encompasses O-carbamyl and N-carbamyl groups.

A carbamate bond describes a —O—C(=O)—NR'— bond, where R' is as described herein.

An "O-thiocarbamyl" group refers to an —OC(=S)—NR'R" group, where each of R' and R" is as defined herein.

An "N-thiocarbamyl" group refers to an R'OC(=S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(=S)—NR'— bond, where R' is as described herein.

A "C-amido" group refers to a —C(=O)—NR'R" group, where each of R' and R" is as defined herein.

An "N-amido" group refers to an R'C(=O)—NR"— group, where each of R' and R" is as defined herein.

An "amide" group encompasses both C-amido and N-amido groups.

An amide bond describes a —NR'—C(=O)— bond, where R' is as defined herein.

An amine bond describes a bond between a nitrogen atom in an amine group (as defined herein) and an R' group in the amine group.

A thioamide bond describes a —NR'—C(=S)— bond, where R' is as defined herein.

A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

As described herein, multimeric protein structures described herein may exhibit improved stability and stronger and/or longer lasting α-galactosidase activity at therapeutically important sites in vivo. Such multimeric protein structures are therefore highly beneficial for use in various medical applications in which α-galactosidase activity is desirable, including therapeutic and research applications.

Hence, according to some embodiments, the multimeric protein structure described herein is for use as a medicament, for example, a medicament for treating Fabry disease.

According to another aspect of embodiments of the invention, there is provided a method of treating Fabry disease, the method comprising administering to a subject in need thereof a therapeutically effective amount of a multimeric protein structure described herein.

According to another aspect of embodiments of the invention, there is provided a pharmaceutical composition that comprises a multimeric protein structure as described herein and a pharmaceutically acceptable carrier.

As used herein a "pharmaceutical composition" refers to a preparation of one or more of the multimeric protein structures described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The pharmaceutical composition optionally comprises an additional ingredient which further stabilizes the α-galactosidase of the multimeric protein structure. Optionally, the additional ingredient is galactose.

Alternatively, a galactose derivative (e.g., a galactose-containing glycoside) may be used instead of galactose. Optionally, a non-reducing galactose derivative is used.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the multimeric protein structure into preparations which can be used pharmaceutically. Proper formulation is dependent upon the route of administration chosen.

For injection or infusion, the multimeric protein structures of embodiments of the invention may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

For oral administration, the multimeric protein structures of the invention can be formulated readily by combining the multimeric protein structures with pharmaceutically acceptable carriers well known in the art. Such carriers enable the multimeric protein structures described herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of doses of active multimeric protein structure.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the multimeric protein structures may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the multimeric protein structures for use according to embodiments of the present invention are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the multimeric protein structures and a suitable powder base such as, but not limited to, lactose or starch.

The multimeric protein structures described herein may be formulated for parenteral administration, e.g., by bolus injection or continuous infusion. Formulations for injection or infusion may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the multimeric protein structure preparation in water-soluble form. Additionally, suspensions of the multimeric protein structures may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the multimeric protein structures to allow for the preparation of highly concentrated solutions.

Alternatively, the multimeric protein structures may be in powder form for constitution with a suitable vehicle, e.g., sterile, pyrogen-free water, before use.

The multimeric protein structure of embodiments of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in the context of the present invention include compositions wherein the active ingredients are contained in an amount effective to achieve the intended purpose. More specifically, a therapeutically effective amount means an amount of multimeric protein structures effective to prevent, alleviate or ameliorate symptoms of disease or prolong the survival of the subject being treated.

For any multimeric protein structures used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test protein structures, which achieves a half-maximal increase in a biological activity of the multimeric protein structure). Such information can be used to more accurately determine useful doses in humans.

As is demonstrated in the Examples section that follows, a therapeutically effective amount for the multimeric protein structures of embodiments of the present invention may range between about 1 μg/kg body weight and about 500 mg/kg body weight.

Toxicity and therapeutic efficacy of the multimeric protein structures described herein can be determined by standard pharmaceutical procedures in experimental animals, e.g., by determining the $EC_{50}$, the $IC_{50}$ and the $LD_{50}$ (lethal dose causing death in 50% of the tested animals) for a subject protein structure. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active moiety which are sufficient to maintain the desired effects, termed the minimal effective concentration (MEC). The MEC will vary for each preparation, but can be estimated from in vitro data; e.g., the concentration necessary to achieve the desired level of activity in vitro. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a multimeric protein structure of embodiments of the invention formulated in a compatible pharmaceutical carrier may also be prepared, placed in an appropriate container, and labeled for treatment of an indicated condition or diagnosis, as is detailed herein.

Thus, according to an embodiment of the present invention, depending on the selected multimeric protein structures, the pharmaceutical composition described herein is packaged in a packaging material and identified in print, in or on the packaging material, for use in the treatment of a condition in which the activity of the multimeric protein structure is beneficial, as described hereinabove.

As used herein the term "about" refers to ±10% The terms "comprises", "comprising", "includes", "including", "having" and their conjugates mean "including but not limited to".

The term "consisting of means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:
bis-N-hydroxysuccinimide-poly(ethylene glycol) (bis-NHS-PEG) was obtained from Iris Biotech GmbH in $PEG_8$ and 2000 Dalton ($PEG_{45}$) PEG forms, and from Pierce in $PEG_5$ form, and dissolved in dimethyl sulfoxide (DMSO) at a concentration of 25 mg/mL;

Citric acid was obtained from Sigma;
Coomassie Blue G250 was obtained from Bio-Rad;
Dimethyl sulfoxide was obtained from Sigma;
D-(+)-galactose was obtained from Sigma;
Human plasma (K3 EDTA) was obtained from Bioreclamation Inc.;
4-Methylumbelliferone was obtained from Sigma;
4-Methylumbelliferyl-α-D-galactopyranoside was obtained from Sigma;
N-dodecanoyl-nitrobenzoxadiazole-ceramide trihexoside ($Gb_3$-NBD) was obtained from Matreya;
2-(N-morpholino)ethanesulfonic acid was obtained from Merck;
Phosphate buffered saline was obtained from Sigma;
p-Nitrophenyl-α-D-galactopyranoside was obtained from Sigma;
Primuline was obtained from Sigma; Primuline spray reagent was prepared by dissolving 12.5 mg primuline in 200 ml acetone:water (8:2 volume ratio);
Pyridine was obtained from Sigma;
Sinapinic acid was obtained from Sigma;
Sodium carbonate was obtained from Sigma;
Sodium phosphate was obtained from Sigma;
Sodium taurocholate was obtained from Sigma;
Trifluoroacetic acid was obtained from Sigma.

Plant Recombinant Human α-GAL-I:
Plant recombinant human α-GAL (prh-α-GAL) having SEQ ID NO: 1, referred to herein as plant recombinant human α-GAL-I (prh-α-GAL-I), was prepared as described in International Patent Application PCT/IL2008/000576 (published as WO 2008/132743).

Transgenic plant material was generated using *Nicotiana benthamiana* plants infiltrated with genetic construct containing the expression cassette for α-GAL-A, for expressing the human α-GAL-A protein. This was performed in a growth chamber under controlled conditions. This was followed by harvest of plant material and extraction of soluble proteins from the plant cells. prh-α-GAL-A was then purified by a purification process involving standard methods for protein purification followed by a chemical modification step to manufacture the cross-linked protein. The current prh-α-GAL-A was extracted from plant material using homogenizers. The plant debris was removed by centrifugation and the protein was further purified using ammonium sulfate precipitation and acidification steps. The supernatant was filtered and loaded onto a hydrophobic column, followed by desalting and loading onto a cation exchange column. The pool of the cation exchange column was concentrated.

Plant Recombinant Human α-GAL-II:
Plant recombinant human α-GAL comprising a mixture of α-GAL having SEQ ID NO: 2 and α-GAL having SEQ ID NO: 3 (without the N-terminal amino acids EF present in SEQ ID NO: 1), referred to herein as prh-α-GAL-II, was prepared by a process similar to that described above for prh-α-GAL-I, using a different genetic construct.

cDNA encoding the human α-galactosidase protein (EC 3.2.1-22 GenBank: X05790) was optimized and synthesized by GENEART AG (Regensburg, Germany). The codon usage without the leader peptide (endoplasmic reticulum target signal peptide) was adapted to the codon bias of *Nicotiana tobaccum* genes. During the optimization process the following cis-acting sequence motifs were avoided: internal TATA-boxes, chi-sites and ribosomal entry sites, AT-rich or GC-rich sequence stretches, RNA instability elements ("killer motifs"), repeat sequences and RNA secondary structures, splice donor (cryptic) and acceptor sites, branch points. In addition, regions of very high (>80%) or very low (<30%) GC content has been avoided.

The nucleotide sequence of the native human α-galactosidase leader peptide (endoplasmic reticulum target signal peptide) of full length human α-galactosidase protein (GenBank: X05790) was replaced with a nucleotide sequence encoding the 33 amino acid endoplasmic reticulum targeting signal peptide (leader peptide) of the *Arabidopsis* ABPI protein. This signal peptide provides efficient targeting of α-galactosidase to the secretory pathway and is cleaved from the polypeptide, by signal peptidase, once the protein has been translocated into the endoplasmic reticulum. A nucleotide sequence encoding the endoplasmic reticulum retention signal SEKDEL was added to the cDNA sequence at the 3' terminus, allowing retrieval of the expressed protein from the Golgi apparatus, effectively maintaining the protein in the endoplasmic reticulum.

The protein of interest was expressed from a strong subgenomic viral promoter of the coat protein. The system relies on transient amplification (by agroinfection) of viral vectors delivered to a plant by *Agrobacterium*. In agroinfection, a plant functional promoter and the cDNA encoding a viral replicon are transferred as T-DNA from *Agrobacterium* into plant cells. The T-DNA is transcribed in-planta by the plant promoter to generate biologically active viral RNA that initiates self replication.

For the transient expression a 3 vector recombination system based on the system previously developed as described [Gleba et al., *Vaccine* 2005, 23:2042-2048]. One of the vectors was inserted with α-galactosidase cDNA and the two other vectors containing genes for construction of the whole viral replicon (RdRp and Integrase), thus generating the biologically active viral RNA that can initiate self replication

*N. benthamiana* plants were germinated and grown in commercial mix soil (Givaat Ada, Ill.) supplemented with granular slow release fertilizer (Scott Marysville, Ohio) under a long day (16 hours light/8 hours dark) light regime at 24-25° C.

*Agrobacteria* were transformed with the pICH20866-alpha-GAL based replicon vector system using electroporation (2500 V, 5 milliseconds) [den Dulk-Ra and Hooykaas, *Methods Mol Biol* 1995, 55:63-72]. Plants were infiltrated with *Agrobacteria* containing the 3 ICON plasmids by vacuum infiltration with standard methods known in the art. Briefly, *N. benthamiana* plants, 5-6 week old, were infiltrated by immersing all aerial plant organs into a bacterial suspension and were placed in a vacuum chamber. A minus (−) 0.8 bar vacuum was applied for 1 minute, followed by a quick return to atmospheric pressure. Plants were returned to the greenhouse for additional 5-7 days under the same growth conditions.

Samples of *Nicotiana benthamiana* leaves were harvested 5 days post infiltration and extracted in Laemmli buffer for SDS-PAGE, or in activity assay buffer (20 mM citric acid, 30 mM sodium phosphate, 0.1% bovine serum albumin and 0.67% ethanol, pH 4.6.) for assay of catalytic activity of the plant expressed protein.

Human α-galactosidase protein from plant extracts was purified by a two-step ammonium sulfate differential precipitation ("salting out": $1^{st}$ step 0.57 M; $2^{nd}$ step 2.27 M), followed by hydrophobic interaction chromatography (Phenyl 650 M resin) and cation exchange chromatography.

Two sequences (i.e., SEQ ID NO: 2 and SEQ ID NO: 3), which differ in the presence or absence of an N-terminal glycine, were obtained due to different leader sequence processing.

4-Methylumbelliferyl-α-D-galactopyranoside Assay of α-GAL Activity:

α-GAL activity was measured using 4-methylumbelliferyl-α-D-galactopyranoside as a hydrolysis substrate. The assay was performed in citrate-phosphate buffer (20 mM citric acid, 30 mM sodium phosphate, pH 4.6). 10 µL of sample containing the tested α-GAL was incubated with 40 µL assay buffer containing 5 mM 4-methylumbelliferyl-α-D-galactopyranoside. The reaction mixture was incubated at 37° C. for 60 minutes. 10 µL of the reaction mixture were transferred into a black 96-well plate (Greiner), 90 µL of stop solution (2 M sodium carbonate) was added, and fluorescence was measured at an excitation wavelength of 365 nm and an emission wavelength of 450 nm. Fluorescence was translated to product concentration, and further to activity, using a calibration curve of 4-methylumbelliferone, the reaction product.

N-Dodecanoyl-nitrobenzoxadiazole-ceramide trihexoside ($Gb_3$-NBD) Assay of α-GAL Activity The fluorescently labeled substrate N-dodecanoyl-nitrobenzoxadiazole-ceramide trihexoside ($Gb_3$-NBD) is less lipophilic than $Gb_3$, facilitating its use in in-vitro enzymatic reactions.

10 µL of 0.1 µg/µL $Gb_3$-NBD (in water with 10% ethanol), and 5 µL of 0.2 mg/mL α-GAL were added to 85 µL of citrate-phosphate buffer at a pH of 4.6. The final α-GAL concentration was 10 µg/mL. The background or non-catalyzed reaction, without α-GAL, was composed of 90 µL of citrate-phosphate buffer at a pH of 4.6 with 10 µL of 0.1 µg/µL $Gb_3$-NBD (in water with 10% ethanol). The reaction mixtures were incubated for 60 minutes at 37° C. Following the incubation, 50 µL methanol was added to the reaction mixture, and the solutions were vortexed for 1 minute. 100 µL chloroform was then added, and the solutions were further vortexed for 1 minute. Water and organic solvents were removed under vacuum using a Speed Vac system. The residues were dissolved in 80 µL of chloroform:methanol (1:1). 30 µL of each sample was loaded on HPTLC (high performance thin layer chromatography) Silica Gel 60 plates (Merck) using a Linomat V system (CAMAG). HPTLC plates were developed using a chloroform:methanol:$H_2O$ solution at a ratio of 100:42:6 as a solvent system. Plates were then allowed to dry and the substrate and product spots were visualized by irradiation under UV light at a wavelength of 365 nm.

p-Nitrophenyl-α-D-galactopyranoside (p-NP-G) Assay of α-GAL Activity:

p-Nitrophenyl-α-D-galactopyranoside was used as a hydrolysis substrate for α-GAL activity assays. The assay buffer contained 20 mM citric acid, 30 mM sodium phosphate, 0.1% BSA (bovine serum albumin) and 0.67% ethanol at pH 4.6. The assay was performed in 96 well ELISA plates (Greiner). 50 µL of sample were incubated with 150 µL assay buffer and 30 µL substrate was added to obtain a final concentration of 8 mM p-nitrophenyl-α-D-galactopyranoside. The reaction mixture was incubated at 37° C. for 90 minutes. After 90 minutes, 100 µL of 1.98 M sodium carbonate was added to each well in order to terminate the reaction. The amount of reaction product was determined by measuring absorbance at 405 nm.

Measurement of α-GAL Stability In Vitro:

The stability of α-GAL from various sources was determined by adding α-GAL to one of the following conditions:

1) simulated lysosomal conditions: citrate-phosphate buffer (20 mM citric acid, 30 mM sodium phosphate), pH 4.6, 37° C.;

2) simulated physiological conditions: phosphate buffered saline (PBS), pH 7.4, 37° C.;

3) human plasma at 37° C.

The α-GAL was added at a concentration of 1 µg/mL, as determined by the activity of α-GAL in the solution, and the solution was incubated at 37° C. Samples of each solution were withdrawn at predetermined time points and the α-GAL activity was measured as described hereinabove. The value of the enzymatic activity immediately after addition of the tested α-GAL to each environment was defined as 100%, and further activity results at the tested time points were calculated as a percentage of that initial activity.

Pharmacokinetics of α-GAL:

Individual Fabry (α-Gal-A −/0) mice were placed in an illuminated plexiglass restraining device, and the enzyme was injected into the tail vein. Blood samples were obtained at the indicated times after injection by either tail bleed or retro-orbital eye bleed, using heparinized microhematocrit tubes. Plasma was diluted in 4-methylumbelliferyl-α-D-galactopyranoside activity buffer. A 4-methylumbelliferyl-α-D-galactopyranoside assay was performed as described above.

Terminal elimination half-life ($T_{1/2}$) was calculated based on plasma activity results. The terminal half-life (elimination half-life) is the time required for the plasma concentration to decrease by 50% after pseudo-equilibrium of distribution has been reached. The terminal half-life was calculated from the terminal (log-linear) portion of the curve, by linear regression of time vs. log concentration [Toutain & Bousquet-Melou, *J Vet Pharmacol Ther* 2004, 27:427-39].

Bio-Distribution of α-GAL:

Fabry (α-Gal-A −/0) mice were injected intravenously (in the tail vein) with α-GAL at a dose of 2 mg/Kg. Tissues (livers, kidneys, hearts, and spleens) were harvested 2 hours, 24 hours, 3 days, 7 days, 14 days or 28 days post-injection of the enzyme. α-GAL levels in normal control mice and in saline-administered (untreated) Fabry mice were compared with the levels in Fabry mice that received exogenous α-GAL. To determine the α-GAL activity in tissues, thawed tissue samples were placed in 2 mL polypropylene tubes containing lysis buffer (28 mM citric acid, 44 mM dibasic sodium phosphate, 0.5% sodium taurocholate, pH 4.4) as described in Oshima et al. [*PNAS* 1997, 94:2540-2544]. The samples were homogenized by use of a Tissuelyzer (Retsch MM400) for 10 minutes. Debris was pelleted by centrifugation at 4° C., and the resulting supernatants were assayed for α-GAL activity by a 4-methylumbelliferyl-α-D-galactopyranoside assay, as described above. The same samples were also subjected to Western blot analysis.

In Vivo $Gb_3$ Assay:

The end point efficacy of injected α-GAL was measured by assay of $Gb_3$ levels of the animal tissues, in order to determine whether $Gb_3$ levels were decreased by α-GAL activity.

To measure $Gb_3$ hydrolysis, neutral glycosphingolipids were extracted from target organs (e.g., liver, kidney, heart and spleen). 100 mg tissue samples were homogenized in 1 mL of 2:1 (v/v) chloroform:methanol and centrifuged for 20 minutes at 13,500 rpm. 62 µL of water was added to 1 mL homogenate to yield a solution of 20:10:2 chloroform:methanol:water. 10 µL pyridine was added to the homogenate to give a final pyridine concentration of 1%. The sample was agitated for 24 hours at 48° C. Solvents and water were removed under vacuum using a SpeedVac system. The sample was resuspended in 2.5 mL methanol and 250 µL of 1 M KOH in methanol was then added. The sample was then shaken for 2 hours at 37° C. The saponification reaction was stopped by the addition of 10 µL of acetic acid. 2.5 mL chloroform was then added to the sample, followed by the addition of 2.5 mL cold water. The sample was vigorously shaken for 5 minutes and was allowed to rest for 5 minutes to allow phase separation. The upper phase, composed of methanol and water, was discarded, and the lower phase, composed of chloroform and methanol, was evaporated under vacuum (SpeedVac), and the residue was resuspended in 300 µL of 1:1 (v/v) chloroform:methanol for analysis of the glycosphingolipids by HPTLC.

Qualitative and semiquantitative analyses of tissue glycolipids were performed by high performance thin layer chromatography (HPTLC) (CAMAG, Switzerland). HPTLC analysis was performed on HPTLC silica gel 60 glass coated plates (Merck). Samples were loaded on the plates using a Linomat 5 system (CAMAG, Switzerland). Plates were developed using chloroform-methanol-water (60:35:4) as the solvent system. Neutral glycosphingolipids were detected with primuline spray reagent. $Gb_3$ was identified using porcine red blood cell $Gb_3$ (Matreya) as a standard, and quantified using a calibration curve of N-heptadecanoyl ceramide trihexoside (Matreya), a semi-synthetic standard. Plates were visualized and relevant spots were quantified using a TLC Scanner 111 (CAMAG, Switzerland) supported by winCATS software (CAMAG, Switzerland).

SDS-PAGE:

SDS-PAGE was carried out under reduced conditions using a Bio-Rad Criterion™ system and in-house casted 12% acrylamide gel. The gel was stained by Coomassie Blue G250 stain.

IEF (Isoelectric Focusing):

IEF was carried out using an Invitrogen Novex® mini-cell and precasted IEF gels having a pH range of 3-7 (Invitrogen). The gel was stained by Coomassie Blue G250.

Mass Spectrometry (MALDI-TOF):

MALDI-TOF was performed using a Bruker Reflex IV MALDI-ToF Mass-spectrometer system (Bruker-Franzen Analytik GmbH, Germany) and a sinapinic acid/trifluoroacetic acid (TFA) (0.1% TFA/acetonitrile (2:1, v/v)) saturated matrix solution.

Example I

In Vitro Stability of Recombinant α-GAL

The in vitro stability of recombinant α-GAL was measured in various conditions as described hereinabove in the Materials and Methods Section. Plant recombinant human α-GAL-I, as well as Fabrazyme® and Replagal® commercial recombinant human α-GAL, were tested.

As shown in FIG. 1, all of the tested types of α-GAL exhibited a loss of activity under simulated lysosomal conditions.

In addition, as shown in FIG. 2, all of the tested types of α-GAL exhibited a loss of activity under simulated physiological conditions. As further shown therein, the presence of 100 mg/mL galactose partially protected the activity of plant recombinant α-GAL-I under such conditions.

Similarly, as shown in FIG. 3, all of the tested types of α-GAL exhibited a loss of activity in human plasma at 37° C.

As shown in FIG. 4, the presence of 100 mg/mL galactose partially protected the activity of plant recombinant α-GAL-I under simulated lysosomal conditions.

Size exclusion chromatography (SEC) experiments at lysosomal and neutral pH levels demonstrated changes in the protein structure (data not shown), while SDS-PAGE and Western blot analyses did not exhibit any degradation of the primary amino acid sequence (data not shown).

These results indicate that α-GAL loses activity under lysosomal conditions and physiological conditions due to alteration of the α-GAL protein structure, and that galactose partially prevents this loss of activity.

Example II

Cross-Linking of Plant Recombinant Human α-GAL-I with Bis-N-Hydroxysuccinimide-poly(ethylene glycol) (bis-NHS-PEG) Agents Plant recombinant human α-GAL-I (prh-α-GAL-I) was cross-linked at 50:1, 100:1 and 200:1 molar ratios with bis-N-hydroxysuccinimide-poly(ethylene glycol) (bis-NHS-PEG) of various molecular weights, namely bis-NHS-PEG$_5$, bis-NHS-PEG$_8$ or bis-NHS-PEG$_{45}$ (bis-NHS-PEG with 2,000 Dalton PEG), the structures of which are shown in FIG. 5.

The bis-NHS-PEG may attach to the protein at two sites on a protein (e.g., lysine residues), thereby forming cross-linking, or at one site on a protein. These two forms of attachment are depicted in FIG. 6.

100 µg α-GAL-I in 28.5 µL of 2-(N-morpholino)ethanesulfonic acid (MES) buffer (25 mM, pH 6) was added to 13.5 µL of phosphate buffer (100 mM, pH 8) containing 100 mg/ml galactose.

α-GAL-I was cross-linked with bis-NHS-PEG$_5$ at 1:50, 1:100, and 1:200 protein:reagent molar ratios, by adding bis-NHS-PEG$_5$ in 8 µL DMSO to the α-GAL-I solution (27.4 µg α-GAL-I solution for a 1:50 molar ratio, 54.8 µg α-GAL-I solution for a 1:100 molar ratio, and 109.7 µg α-GAL-I solution for a 1:200 molar ratio).

α-GAL-I was cross-linked with bis-NHS-PEG$_{45}$ at 1:50, 1:100, and 1:200 protein:reagent molar ratios, by adding bis-NHS-PEG$_{45}$ in 8 μL DMSO to the α-GAL-I solution (103 μg α-GAL-I solution for a 1:50 molar ratio, 206 μg α-GAL-I solution for a 1:100 molar ratio, and 412 μg α-GAL-I solution for a 1:200 molar ratio) α-GAL-I was crosslinked with bis-NHS-PEG$_8$ at 1:50, 1:100, and 1:200 protein:reagent molar ratios, by adding bis-NHS-PEG$_8$ in 11.5 μL DMSO to the α-GAL-I solution (37 μg α-GAL-I for a 1:50 molar ratio, 73 μg α-GAL-I solution for a 1:100 molar ratio, and 146 μg α-GAL-I solution for a 1:200 molar ratio).

After adding the bis-NHS-PEG agent to the α-GAL-I, the reactions were pipetted and agitated on an orbital shaker for 2 hours at room temperature.

In all reactions the excess of bis-NHS-PEG cross-linking reagent was removed by dialysis against saline (50 KDa cut off).

The yield of dimer increased with increasing protein concentration and DMSO concentration, reaching up to 30%.

The reaction products were analyzed by SDS-PAGE (sodium dodecyl sulfate-polyacrylamide gel electrophoresis), IEF (isoelectric focusing), Western blot, and MALDI-TOF mass spectrometry, as described hereinabove.

As shown in FIG. 7, the standard native prh-α-GAL-I was observed as a monomer (having a molecular weight of 48 KDa) following gel electrophoresis, whereas following reaction of prh-α-GAL-I with bis-NHS-PEG, prh-α-GAL-I appeared primarily in the form of a dimer (with some monomer present), indicating that the two monomers were covalently linked by cross-linking with bis-NHS-PEG.

As is further shown in FIG. 7, a higher proportion of monomeric prh-α-GAL-I was observed with the shorter cross-linkers, bis-NHS-PEG$_5$ and bis-NHS-PEG$_8$, than with the longer cross-linker bis-NHS-PEG$_{45}$. The bis-NHS-PEG$_{45}$ yielded a high proportion of cross-linked protein. These results indicate that the shorter cross-linkers are less effective at covalently linking monomers.

As is further shown in FIG. 7, for each of the tested cross-linkers, the molecular weight of the monomeric portion of prh-α-GAL-I increased following reaction with the cross-linker. The increase in molecular weight was greater when a higher ratio of cross-linker to protein was used (e.g., 200:1), and when the molecular weight of the cross-linker was greater (e.g., bis-NHS-PEG$_{45}$). These results indicate that protein monomers which were not dimerized by cross-linking, were covalently attached to the bis-NHS-PEG cross-linker, i.e., the proteins were PEGylated.

The above results indicate that the use of higher molar excess of cross-linker to protein yields higher levels of α-GAL modification, including both cross-linking to form a dimer and PEGylation of the proteins. However, a molar ratio of 100:1 provided a high level of cross-linking, especially in the reactions using the bis-NHS-PEG$_{45}$ reagent, such that a molar ratio of 200:1 provided only a marginal addition to the cross-linking efficiency.

Figure 8:
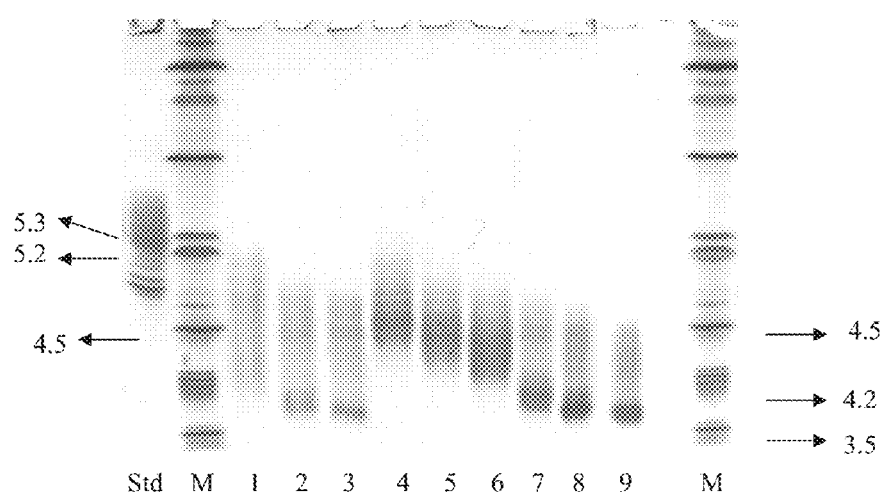
FIG. 8 presents a scan of an isoelectric focusing gel showing plant recombinant α-GAL-I which was reacted with bis-NHS-$PEG_5$ (lanes 1-3), bis-NHS-$PEG_8$ (lanes 7-9), and bis-NHS-$PEG_{45}$ (lanes 4-6), at a molar ratio of 50:1 (lanes 1, 4 and 7), 100:1 (lanes 2, 5 and 8) and 200:1 (lanes 3, 6 and 9) bis-NHS-PEG:α-GAL, as well as pH markers (M) and non-reacted plant recombinant α-GAL-I standard (Std) (arrows show pH values for various bands)

As shown in FIG. 8, reacting prh-α-GAL-I with bis-NHS-PEG reduced the isoelectric point (pI) of prh-α-GAL-I, thereby confirming that the bis-NHS-PEG is covalently attached to the prh-α-GAL-I. Attachment of bis-NHS-PEG to prh-α-GAL-I converts basic amine groups in lysine residues to neutral amide groups, thereby reducing the pI. The reduction in pI was more pronounced when a greater molar excess (e.g., 200:1) of bis-NHS-PEG was used, confirming the above results obtained with SDS-PAGE.

As is further shown in FIG. 8, the pI is reduced more by bis-NHS-PEG$_5$ and bis-NHS-PEG$_8$ than by bis-NHS-PEG$_{45}$.

This result indicates that bis-NHS-PEG$_5$ and bis-NHS-PEG$_8$ are more likely than bis-NHS-PEG$_{45}$ to result in PEGylation in which only one terminus of the cross-linker is attached to α-GAL. A cross-linker attached to α-GAL at only one terminus is more effective at reducing the pI because such a cross-linker comprises an acidic carboxylic (—CO$_2$H) group at the non-attached terminus, in addition to converting a lysine amine group to an amide group at the attached terminus.

Figure 9:
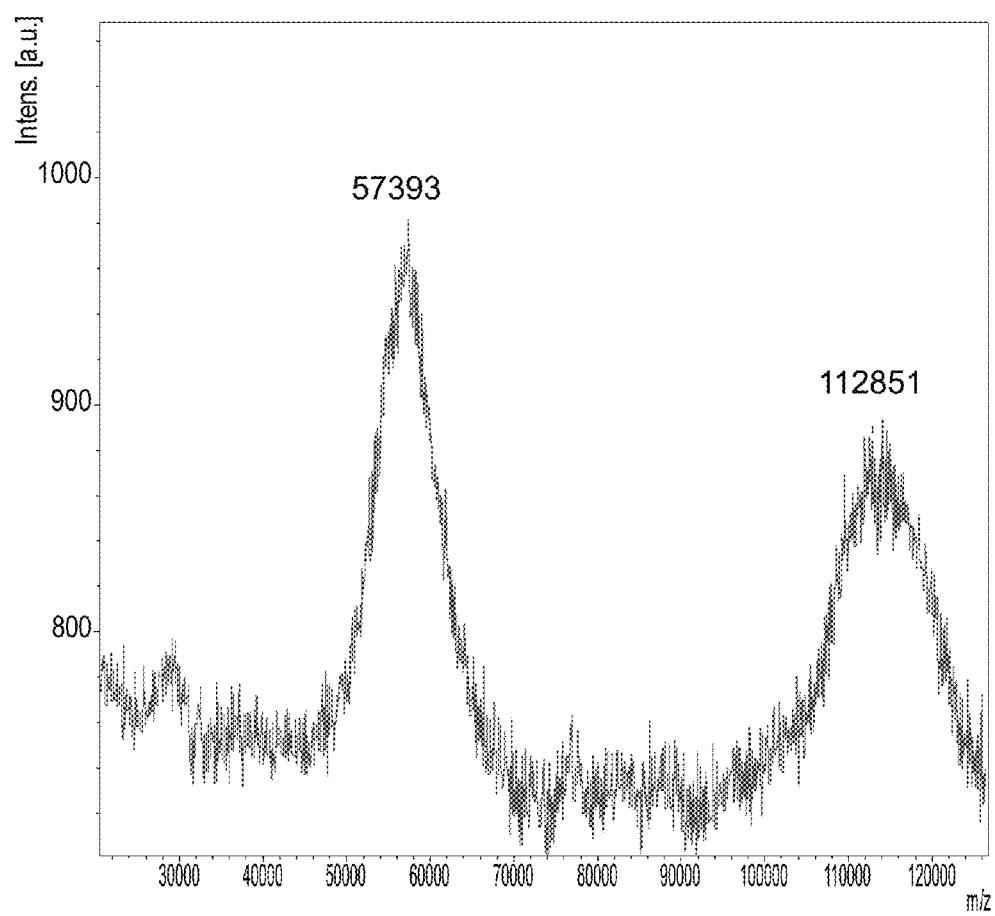
FIG. 9 is a MALDI-TOF mass spectroscopy spectrum of plant recombinant α-GAL-I cross-linked by bis-NHS-$PEG_{45}$ (x-axis indicates m/z values, and m/z values of peaks are shown)

As shown in FIG. 9, reacting prh-α-GAL-I with bis-NHS-PEG$_{45}$ cross-linker increased the molecular weight of the prh-α-GAL-I dimer from 97 KDa to 113 KDa, as determined by MALDI-TOF mass spectrometry. The increase in molecular weight indicates an addition of approximately 8 molecules of bis-NHS-PEG$_{45}$ to the prh-α-GAL-I dimer.

Figure 10:
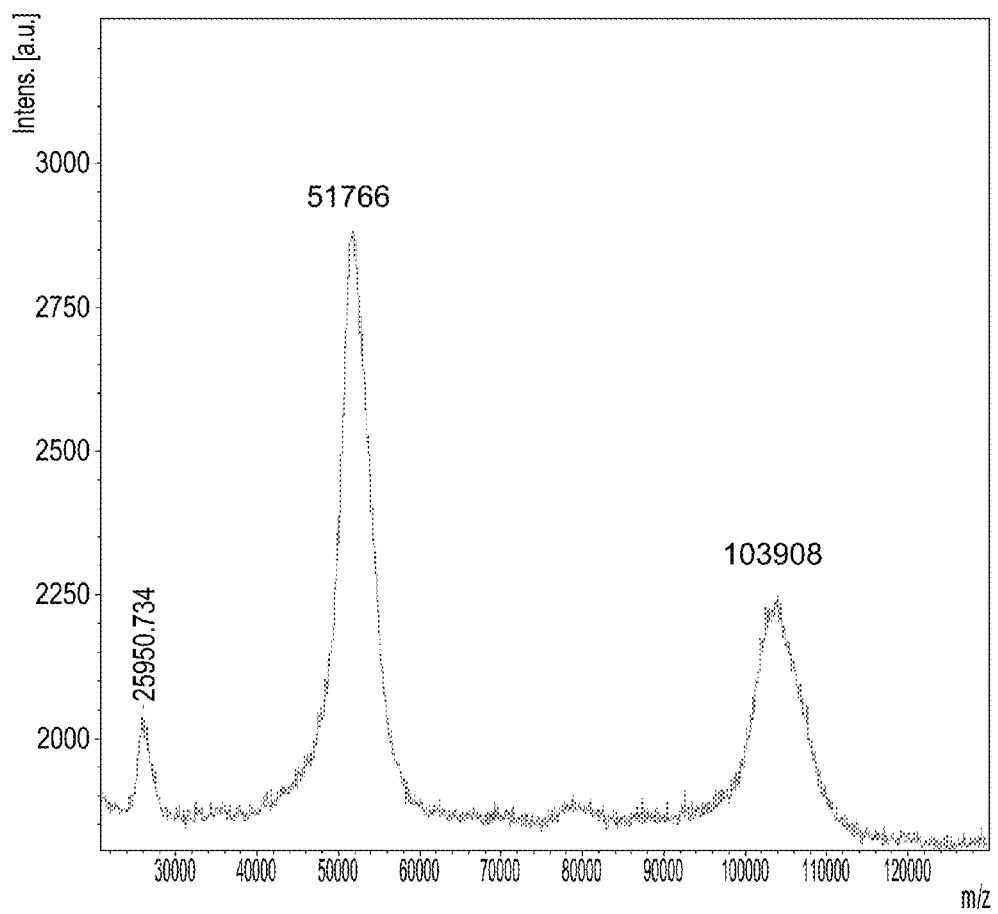
FIG. 10 is a MALDI-TOF mass spectroscopy spectrum of plant recombinant α-GAL-I cross-linked by bis-NHS-$PEG_8$ (x-axis indicates m/z values, and m/z values of peaks are shown)
Figure 11:
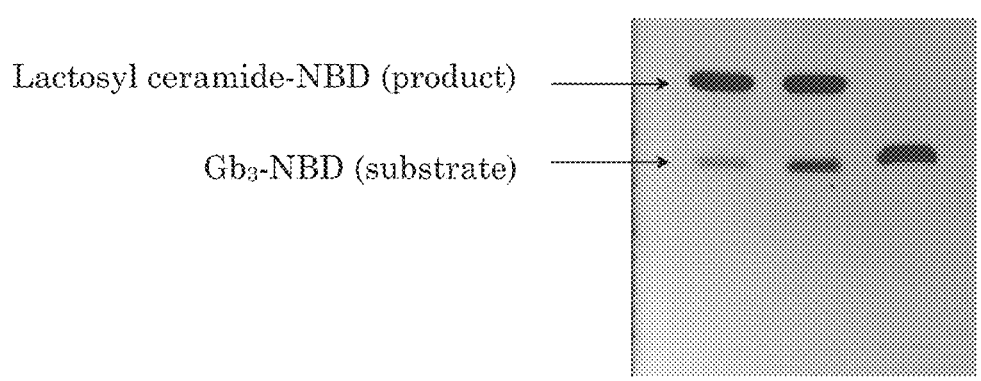
FIG. 11 presents a photograph showing the α-GAL substrate N-dodecanoyl-nitrobenzoxadiazole-ceramide trihexoside ($Gb_3$-NBD) and the α-GAL reaction product lactosyl ceramide-nitrobenzoxadiazole (lactosyl ceramide-NBD), as visualized by irradiation under UV light (365 nm) following high performance thin layer chromatography, following incubation of the substrate $Gb_3$-NBD with plant recombinant human α-GAL-I cross-linked with bis-NHS-PEG$_{45}$ (left lane), Replagal® α-GAL (middle lane) and without α-GAL (right lane)

As shown in FIG. 10, reacting prh-α-GAL-I with a bis-NHS-PEG$_8$ cross-linker increased the molecular weight of the prh-α-GAL-I dimer from 97 KDa to 104 KDa, as determined by MALDI-TOF mass spectrometry. The increase in molecular weight indicates an addition of approximately 10 molecules of bis-NHS-PEG$_8$ to the prh-α-GAL-I dimer.

Example III

Activity of Cross-Linked Plant Recombinant Human α-Gal-I

In order to determine whether the cross-linked plant recombinant α-GAL-I (prh-α-GAL-I) described in Example II retained enzymatic activity, the cross-linked prh-α-GAL-I was assayed for its enzymatic activity using the 4-methylumbelliferyl-α-D-galactopyranoside assay described hereinabove.

As shown in Table 1 below, prh-α-GAL-I which was reacted with bis-NHS-PEG$_5$, bis-NHS-PEG$_8$ or bis-NHS-PEG$_{45}$ at molar excesses of 50:1, 100:1 and 200:1 bis-NHS-PEG reagent in all cases exhibited a level of enzymatic activity similar to that of native prh-α-GAL-I. As shown therein, both moderate decreases and moderate increases in activity were observed in some cases, which may be a result of formulation effects. These results indicate that the cross-linking did not reduce the activity of prh-α-GAL-I.

TABLE 1

Activity results of cross-linked plant recombinant human α-GAL I

| Sample | Reagent | Molar excess | Activity mg/mL |
|---|---|---|---|
| standard | — | — | 2 |
| 1 | Bis-NHS-PEG$_5$ | 50:1 | 2.25 |
| 2 | Bis-NHS-PEG$_5$ | 100:1 | 1.30 |
| 3 | Bis-NHS-PEG$_5$ | 200:1 | 1.24 |
| 4 | Bis-NHS-PEG$_{45}$ | 50:1 | 2.82 |
| 5 | Bis-NHS-PEG$_{45}$ | 100:1 | 2.76 |
| 6 | Bis-NHS-PEG$_{45}$ | 200:1 | 3.48 |
| 7 | Bis-NHS-PEG$_8$ | 50:1 | 2.18 |
| 8 | Bis-NHS-PEG$_8$ | 100:1 | 2.43 |
| 9 | Bis-NHS-PEG$_8$ | 200:1 | 1.82 |

The activity of the bis-NHS-PEG$_{45}$ cross-linked prh-α-GAL-I was further verified using the N-dodecanoyl-NBD-ceramide trihexoside assay described hereinabove, which assays the activity of α-GAL towards its natural substrate, ceramide trihexoside (Gb$_3$). Replagal® mammalian recombinant human α-GAL was assayed for comparison.

As shown in FIG. 11, following incubation of the cross-linked plant recombinant human α-GAL-I with the fluorescent substrate, almost all substrate was converted to the product, N-dodecanoyl-nitrobenzoxadiazole-lactosyl ceramide, similarly to the reaction catalyzed by the mammalian recombinant α-GAL (Replagal®). This result confirms that the cross-linking did not impair the enzymatic hydrolytic efficiency of the prh-α-GAL-I, using a close analog of the natural substrate.

Example IV

In Vitro Stability of Cross-Linked Plant Recombinant Human α-GAL-I

The in vitro stability of the cross-linked plant recombinant human α-GAL-I (prh-α-GAL-I), obtained as described in Example II, was measured in various conditions as described hereinabove in the Materials and Methods Section. The stability of Fabrazyme® and Replagal® commercial recombinant human α-GALs was measured for comparison.

Figure 12A:
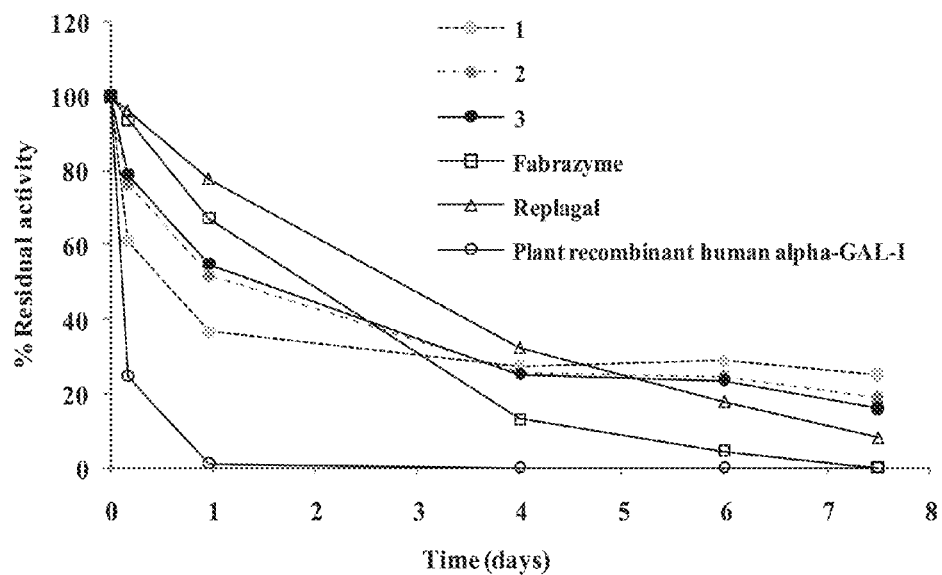
FIGS. 12A, 12B and 12C, are graphs showing the activity of Fabrazyme® α-GAL, Replagal® α-GAL, plant recombinant human α-GAL-I, and plant recombinant human α-GAL-I cross-linked with bis-NHS-PEG$_5$ (FIG. 12A), bis-NHS-PEG$_8$ (FIG. 12B) and bis-NHS-PEG$_{45}$ (FIG. 12C) at a molar ratio of 50:1 ("1" in FIG. 12A, "7" in FIG. 12B and "4" in FIG. 12C), 100:1 ("2" in FIG. 12A, "8" in FIG. 12B and "5" in FIG. 12C) and 200:1 ("3" in FIG. 12A, "9" in FIG. 12B and "6" in FIG. 12C) bis-NHS-PEG:α-GAL as a function of incubation time under simulated lysosomal conditions (citrate phosphate buffer, pH 4.6, 37° C.)
Figure 12B:
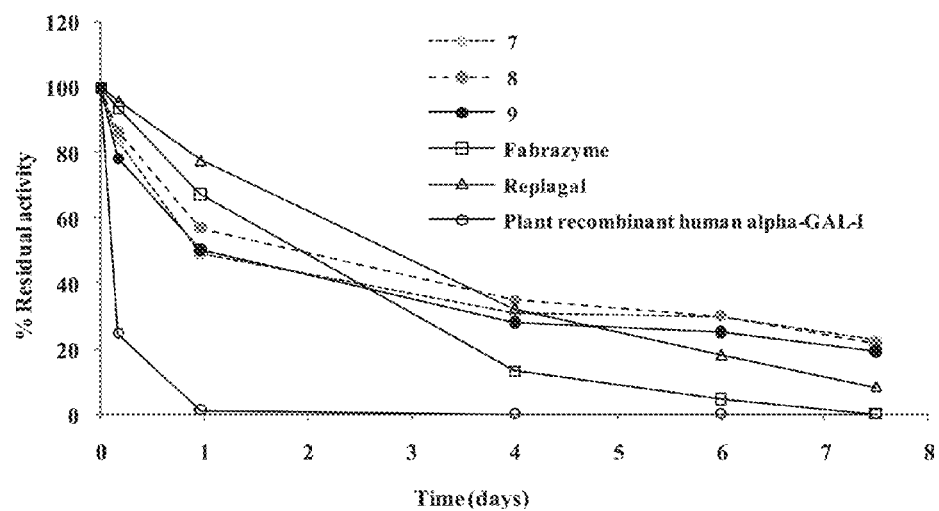
Figure 12C:
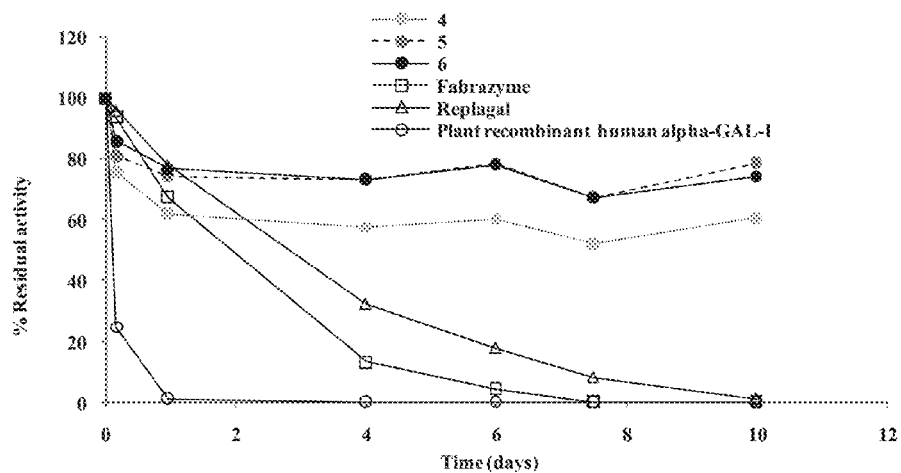
Figure 13:
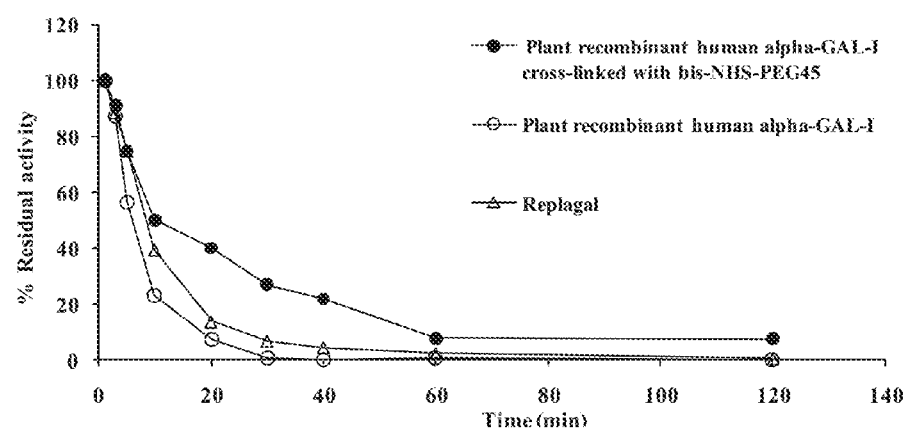
FIG. 13 is a graph showing the pharmacokinetic profile of Replagal® α-GAL, plant recombinant human α-GAL-I, and plant recombinant human α-GAL-I cross-linked with bis-NHS-PEG$_{45}$ in the plasma of Fabry mice; the residual activity of each α-GAL is presented as a percentage of the maximal residual activity of each α-GAL, as a function of time following injection of the α-GALs.

As shown in FIGS. 12A-12C, the stability of plant recombinant human α-GAL-I under simulated lysosomal conditions was enhanced by cross-linking with bis-NHS-PEG$_5$ (FIG. 12A), bis-NHS-PEG$_8$ (FIG. 12B) and bis-NHS-PEG$_{45}$ (FIG. 12C). As further shown therein, the stability of the cross-linked prh-α-GAL-I over the course of one week compared favorably to the stability of the commercial recombinant human α-GAL. After a small decrease in residual activity during the first 24 hours, the cross-linked prh-α-GAL-I maintained activity, even after 10 days. The initial decrease in activity, observed during the first 24 hours, may reflect the portion of plant recombinant human α-GAL-I that did not undergo cross-linking.

As further shown in FIGS. 12A-12C, prh-α-GAL-I cross-linked by bis-NHS-PEG$_{45}$ exhibited the highest stability under simulated lysosomal conditions.

The stability of plant recombinant human α-GAL-I in human plasma at 37° C. was also enhanced by cross-linking with bis-NHS-PEG$_{45}$ (data not shown).

These results indicate that cross-linking α-GAL as described herein can increase the efficacy of α-GAL in vivo by increasing the stability of α-GAL in lysosomes, thereby allowing α-GAL to act for a longer period of time in the lysosomes, and by increasing the stability of α-GAL in the blood, thereby increasing the circulatory half-life of α-GAL.

Example V

In Vivo Pharmacokinetics and Bio-Distribution of Cross-Linked Plant Recombinant Human α-GAL-I The pharmacokinetics and bio-distribution of plant recombinant human α-GAL-I (prh-α-GAL-I) cross-linked with bis-NHS-PEG$_{45}$ or bis-NHS-PEG$_8$ as described in Example II was determined in Fabry mice injected with 2 mg/Kg of α-GAL, as described hereinabove in the Materials and Methods Section. The pharmacokinetics and bio-distribution of non-cross-linked plant recombinant human α-GAL-I and of Replagal® recombinant human α-GAL was determined for comparison. Blood samples were collected for pharmacokinetic analysis 1, 3, 5, 10, 20, 30, 40, 60 and 120 minutes post-injection. For each type of α-GAL, the treatment group consisted of six mice.

As shown in Table 2 below, cross-linking prh-α-GAL-I with bis-NHS-PEG$_8$ and with bis-NHS-PEG$_{45}$ increased the circulatory terminal half-life of plant recombinant human α-GAL-I, with the latter exhibiting a more pronounced effect.

TABLE 2

Circulatory terminal half-lives of recombinant α-GAL

| α-GAL sample | $t_{1/2}$ (minutes) |
| --- | --- |
| Replagal® mammalian recombinant human α-GAL | 8.1 |
| Plant recombinant human α-GAL-I | 4.8 |
| Plant recombinant human α-GAL I cross-linked with bis-NHS-PEG$_8$ | 6.2 |
| Plant recombinant human α-GAL-I cross-linked with bis-NHS-PEG$_{45}$ | 90 |

As shown in FIG. 13 and in Table 2, the terminal half-life of prh α-GAL-I cross-linked by bis-NHS-PEG$_{45}$ was considerably greater than the terminal half-life of Replagal® α-GAL.

As further shown in FIG. 13, the activity of plant recombinant human α-GAL-I cross-linked with bis-NHS-PEG$_{45}$ at 20 minutes was about 40% of the activity at 1 minute. Furthermore, the cross-linked prh-α-GAL-I exhibited an active plasma presence even 4 hours post-injection.

These results indicate that the cross-linked prh-α-GAL-I remains active in vivo for a relative long time, which can allow the enzyme to reach additional tissues and organs.

Figure 14A:
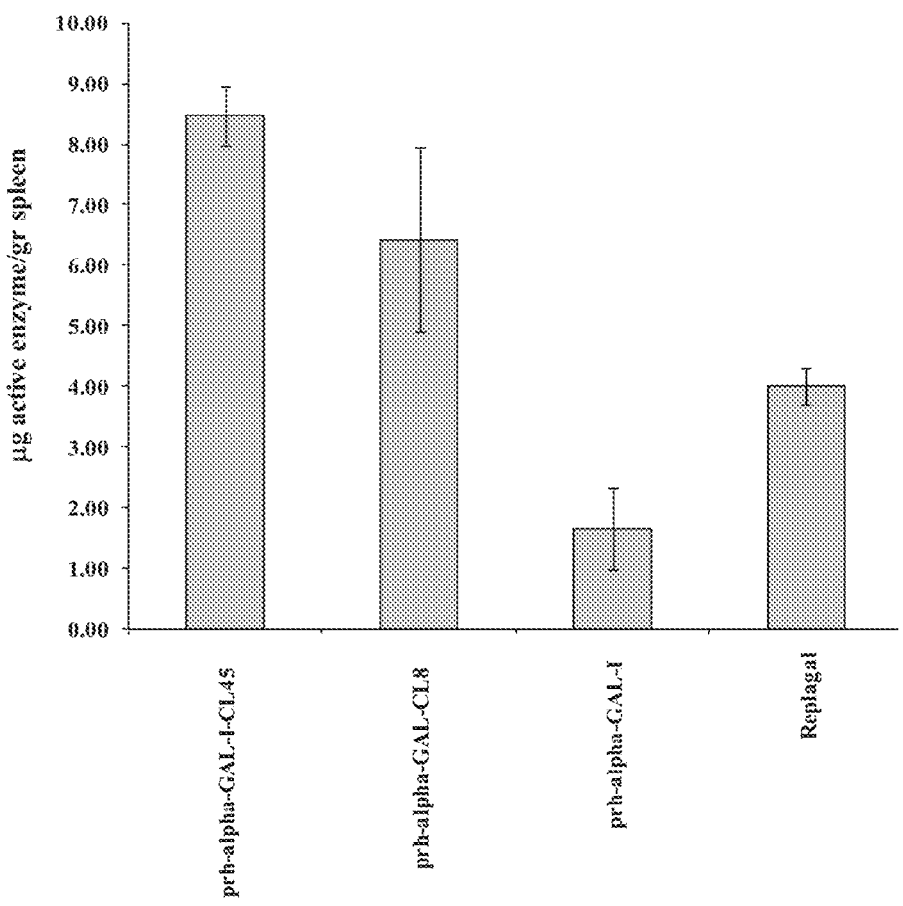
FIGS. 14A and 14B present a graph (FIG. 14A) showing the activity of Replagal® α-GAL, plant recombinant human α-GAL-I (prh-alpha-GAL-I), and plant recombinant human α-GAL-I cross-linked with bis-NHS-PEG$_8$ (prh-alpha-GAL-1-CL8) or bis-NHS-PEG$_{45}$ (prh-alpha-GAL-1-CL45) in the spleens of Fabry mice 2 hours following injection of α-GAL, and a photograph of a Western blot (FIG. 14B) showing Replagal® α-GAL (lanes 10-12 and 15), plant recombinant human α-GAL-I (lanes 7-9 and 13), and plant recombinant human α-GAL-I cross-linked with bis-NHS-PEG$_8$ (lanes 4-6) or bis-NHS-PEG$_{45}$ (lanes 1-3 and 14) in the spleens of Fabry mice following injection of α-GAL (lanes 1-12) or as a standard consisting of 50 ng α-GAL (lanes 13-15)
Figure 14B:
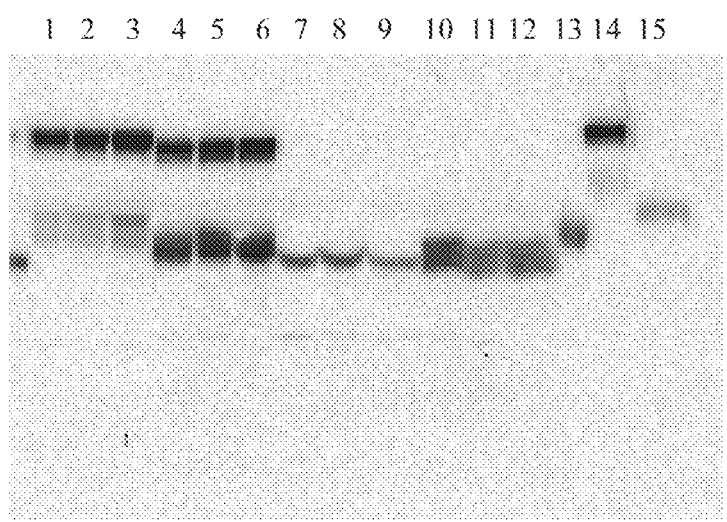
Figure 15A:
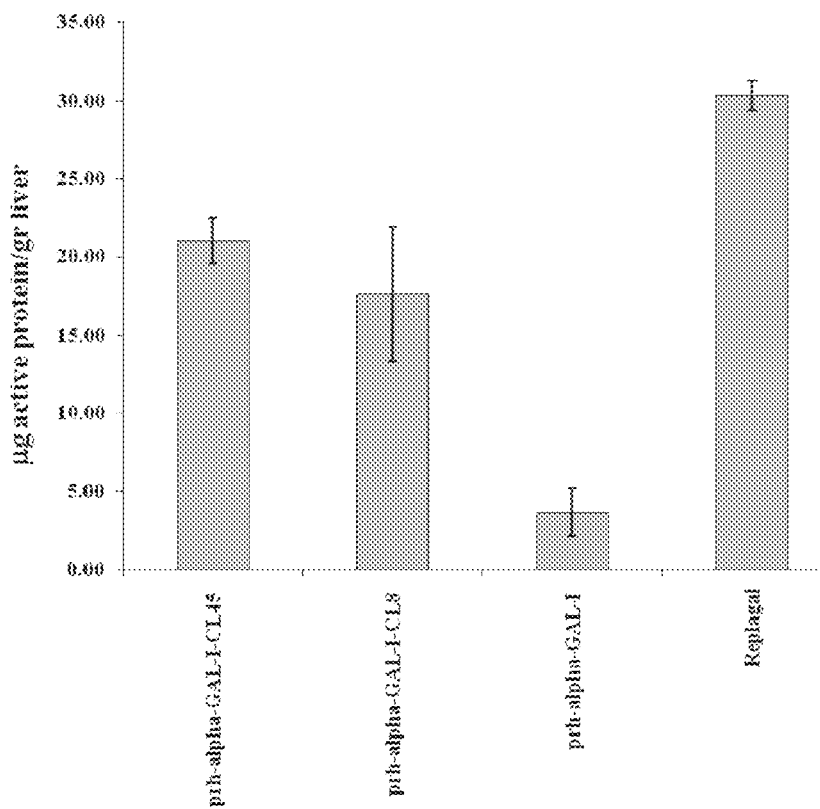
FIGS. 15A and 15B present a graph (FIG. 15A) showing the activity of Replagal® α-GAL, plant recombinant human α-GAL-I (prh-alpha-GAL-I), and plant recombinant human α-GAL-I cross-linked with bis-NHS-PEG$_8$ (prh-alpha-GAL-1-CL8) or bis-NHS-PEG$_{45}$ (prh-alpha-GAL-1-CL45) in the livers of Fabry mice 2 hours following injection of α-GAL, and a photograph of a Western blot (FIG. 15B) showing Replagal® α-GAL (lanes 10-12 and 15), plant recombinant human α-GAL-I (lanes 7-9 and 13), and plant recombinant human α-GAL-I cross-linked with bis-NHS-PEG$_8$ (lanes 4-6) or bis-NHS-PEG$_{45}$ (lanes 1-3 and 14) in the livers of Fabry mice following injection of α-GAL (lanes 1-12) or as a standard consisting of 50 ng α-GAL (lanes 13-15)
Figure 15B:
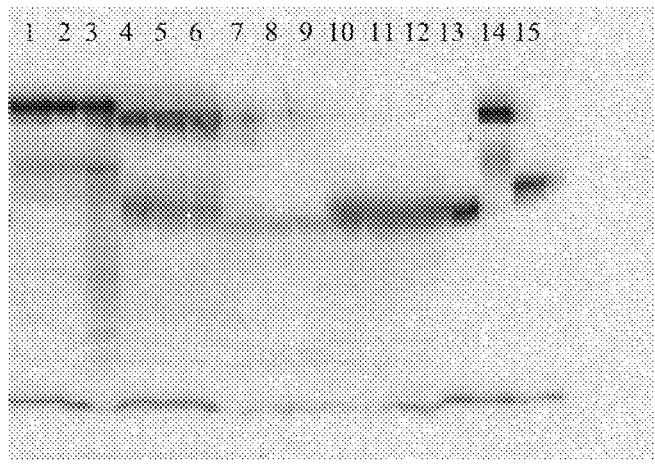

As shown in FIGS. 14A and 14B, the levels of plant recombinant α-GAL-I cross-linked with bis-NHS-PEG$_8$ and bis-NHS-PEG$_{45}$ in the spleens of Fabry mice 2 hours post-injection were considerably higher than those of non-cross-linked plant recombinant α-GAL-I as well those of Replagal® mammalian recombinant α-GAL. As further shown therein, levels of prh-α-GAL-I cross-linked with bis-NHS-PEG$_{45}$ were higher than levels of prh-α-GAL-I cross-linked with bis-NHS-PEG$_8$. The Western blot analyses (FIG. 14B) are consistent with the bio-distribution results obtained by assaying α-GAL enzymatic activity (FIG. 14A).

As shown in FIGS. 15A and 15B, the levels of plant recombinant α-GAL-I cross-linked with bis-NHS-PEG$_8$ and bis-NHS-PEG$_{45}$ in the livers of Fabry mice 2 hours post-injection were considerably higher than those of non-cross-linked plant recombinant α-GAL-I, but lower than levels of Replagal® mammalian recombinant α-GAL in the liver. As further shown therein, levels of prh-α-GAL-I cross-linked with bis-NHS-PEG$_{45}$ were slightly higher than levels of prh-α-GAL-I cross-linked with bis-NHS-PEG$_8$. The Western blot analyses (FIG. 15B) are consistent with the bio-distribution results obtained by assaying α-GAL enzymatic activity (FIG. 15A).

Lower levels of α-GAL in the liver may be therapeutically advantageous, as about 95% of the recovered enzyme in enzyme replacement therapy is typically found in the liver, and hence high levels of recombinant α-GAL in the liver indicate lower levels of exogenous α-GAL in target organs, such as heart and kidneys.

Figure 16:
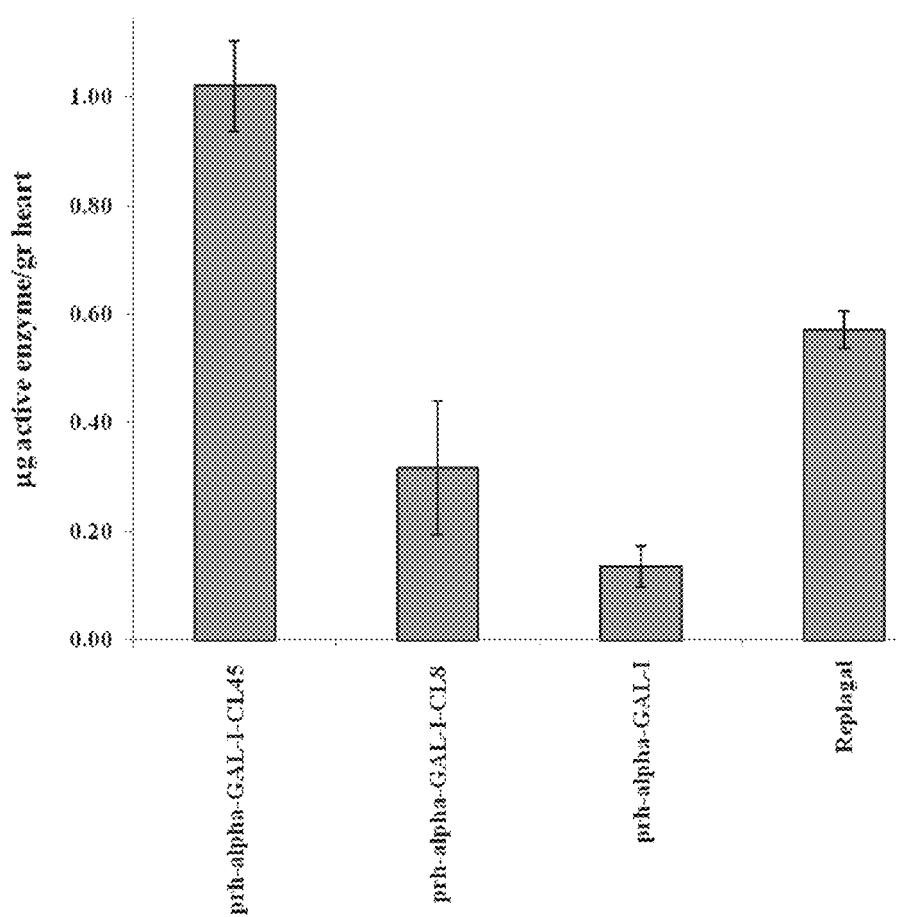
FIG. 16 is a graph showing the activity of Replagal® α-GAL, plant recombinant human α-GAL-I (prh-alpha-GAL-I), and plant recombinant human α-GAL-I cross-linked with bis-NHS-PEG$_8$ (prh-alpha-GAL-1-) or bis-NHS-PEG$_{45}$ (prh-alpha-GAL-1-CL45) in the hearts of Fabry mice 2 hours following injection of α-GAL.

As shown in FIG. 16, the levels of plant recombinant α-GAL-I cross-linked with bis-NHS-PEG$_8$ and bis-NHS-PEG$_{45}$ in the hearts of Fabry mice 2 hours post-injection were higher than those of non-cross-linked plant recombinant α-GAL-I. As further shown therein, levels of prh-α-GAL-I cross-linked with bis-NHS-PEG$_{45}$ were higher than levels of prh-α-GAL-I cross-linked with bis-NHS-PEG$_8$, as well as levels of Replagal® mammalian recombinant α-GAL.

Figure 17:
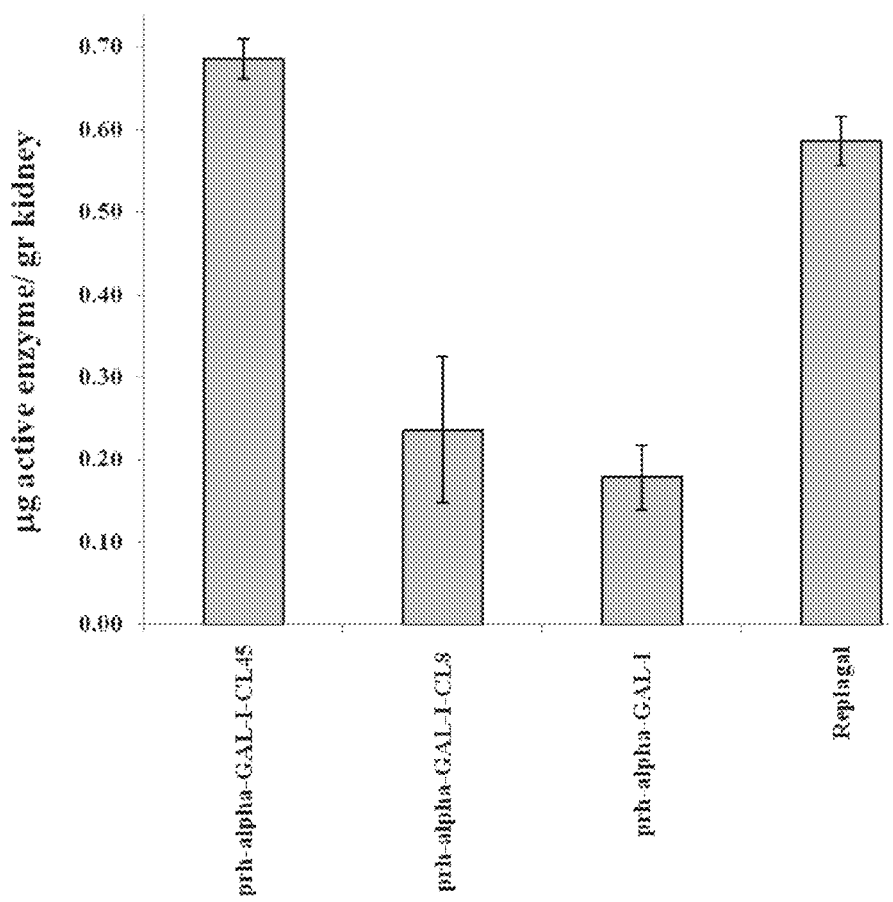
FIG. 17 is a graph showing the activity of Replagal® α-GAL, plant recombinant human α-GAL-I (prh-alpha-GAL-I), and plant recombinant human α-GAL-I cross-linked with bis-NHS-PEG$_8$ (prh-alpha-GAL-1-CL8) or bis-NHS-PEG$_{45}$ (prh-alpha-GAL-1-CL45) in the kidneys of Fabry mice 2 hours following injection of α-GAL.
Figure 18:
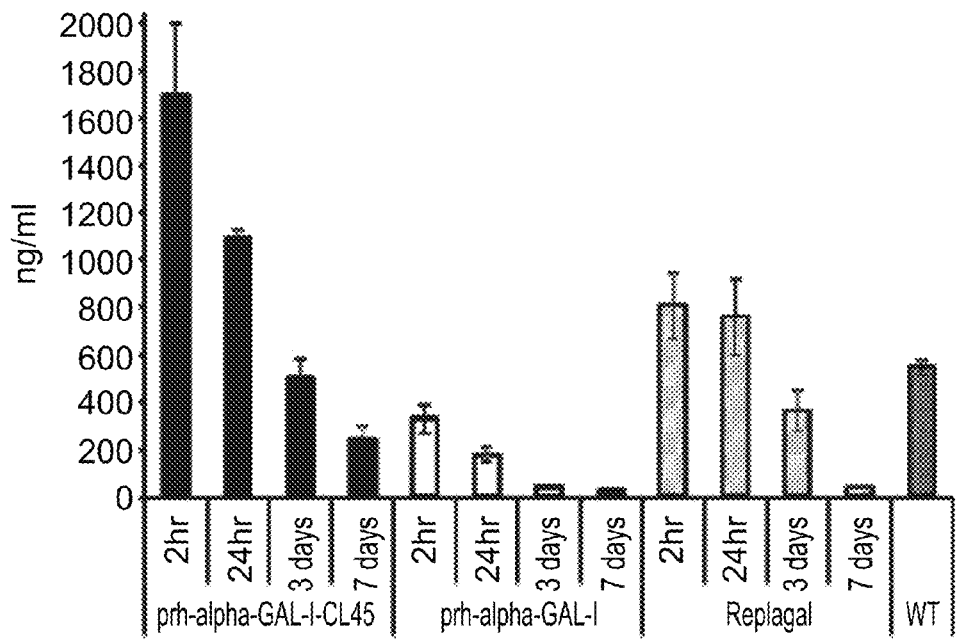
FIG. 18 is a graph showing the activity of Replagal® α-GAL and plant recombinant human α-GAL-I (prh-alpha-GAL-I), and plant recombinant human α-GAL-I cross-linked with bis-NHS-PEG$_{45}$ (prh-alpha-GAL-1-CL45) in the spleens of Fabry mice 2 hours, 24 hours, 3 days and 7 days following injection of α-GAL (endogenous wild type α-GAL (WT) is shown as a standard)

As shown in FIG. 17, the levels of plant recombinant α-GAL-I cross-linked with bis-NHS-PEG$_8$ and bis-NHS-PEG$_{45}$ in the kidneys of Fabry mice 2 hours post-injection were higher than those of non-cross-linked plant recombinant α-GAL-I. As further shown therein, levels of prh-α-GAL-I cross-linked with bis-NHS-PEG$_{45}$ were higher than levels of prh-α-GAL-I cross-linked with bis-NHS-PEG$_8$, as well as levels of Replagal® mammalian recombinant α-GAL.

Similarly, as shown in FIGS. 18-21, the levels of plant recombinant α-GAL-I cross-linked with bis-NHS-PEG$_{45}$ were higher than the levels of non-cross-linked plant recombinant α-GAL-I in the spleen (FIG. 18), liver (FIG. 19), heart (FIG. 20) and kidneys (FIG. 21) of Fabry mice, for up to 7 days post-injection. As further shown therein, the levels of plant recombinant α-GAL-I cross-linked with bis-NHS-PEG$_{45}$ were higher than the levels of Replagal® mammalian recombinant α-GAL in the spleen, heart and kidneys.

These results indicate that α-GAL cross-linked with bis-NHS-PEG, particularly bis-NHS-PEG$_{45}$, exhibits enhanced uptake into organs, including the kidney and heart, which are major target organs in the treatment of Fabry disorder. These results are consistent with the increased circulatory half-life and enhanced stability of cross-linked α-GAL.

Example VI

Cross-Linking of Mammalian Recombinant Human α-Gal with Bis-N-hydroxysuccinimide-poly(ethylene glycol) (bis-NHS-PEG)

In order to confirm the advantageous effects of cross-linking described hereinabove, Replagal® mammalian recombinant human α-GAL, which is produced from human fibrosarcoma line HT-1080, was cross-linked.

333 μL of phosphate buffer (100 mM, pH 8) with 100 mg/ml D-(+)-galactose was added to 3.8 mg bis-NHS-PEG$_{45}$ in 151 μL of DMSO solution (25 mg/ml) and 1.8 mg of Replagal® recombinant human α-GAL in 130 μL citrate buffer (25 mM, pH 6). Replagal® α-GAL concentration was determined by an activity assay. The reaction mixture was agitated using an orbital shaker for 2 hours at room temperature. The excess of bis-NHS-PEG$_{45}$ cross-linking reagent was removed by dialysis against saline using a Vivaspin 6 concentrator with a cut-off of 50 KDa. The α-GAL activity of the cross-linked Replagal® α-GAL indicated that the α-GAL concentration was 3 mg/mL.

The reaction products were analyzed by SDS-PAGE (sodium dodecyl sulfate-polyacrylamide gel electrophoresis), IEF (isoelectric focusing), and MALDI-TOF mass spectrometry, as described hereinabove.

Figure 22:
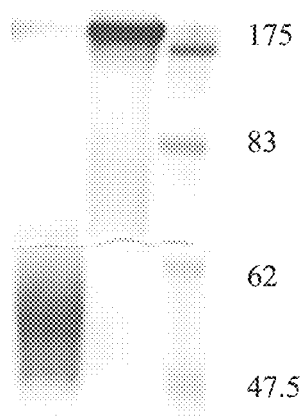
FIG. 22 presents a photograph of an image of an SDS-PAGE gel showing Replagal® mammalian recombinant human α-GAL (left lane), and Replagal® mammalian recombinant human α-GAL which was reacted with bis-NHS-PEG$_{45}$ (middle lane), as well as molecular weight markers (right lane; molecular weights of markers are indicated in KDa units)

As shown in FIG. 22, the standard native Replagal® α-GAL was observed as a monomer following gel electrophoresis, whereas following reaction of Replagal® α-GAL with bis-NHS-PEG$_{45}$, the α-GAL appeared in the form of a dimer, indicating that the two monomers were covalently linked by cross-linking with bis-NHS-PEG.

Figure 23:
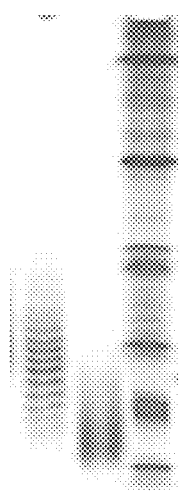
FIG. 23 presents a photograph of an isoelectric focusing gel showing Replagal® mammalian recombinant human α-GAL (left lane), and Replagal® mammalian recombinant human α-GAL which was reacted with bis-NHS-PEG$_{45}$ (middle lane), as well as pH markers (right lane)

As shown in FIG. 23, reacting Replagal® α-GAL with bis-NHS-PEG$_{45}$ reduced the isoelectric point (pI) of the α-GAL, thereby confirming that the bis-NHS-PEG is covalently attached to the α-GAL.

Figure 24A:
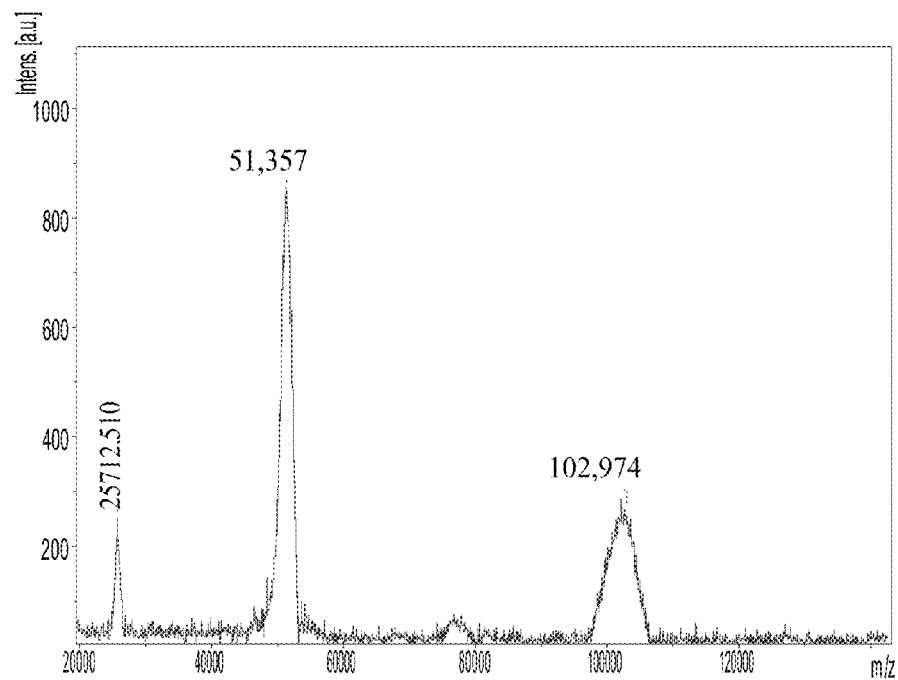
FIGS. 24A and 24B are MALDI-TOF mass spectroscopy spectra of Replagal® mammalian recombinant human α-GAL (FIG. 24A), and Replagal® mammalian recombinant human α-GAL cross-linked by bis-NHS-PEG$_{45}$ α-axis indicates m/z values, and m/z values (in Da units) of peaks are shown)
Figure 24B:
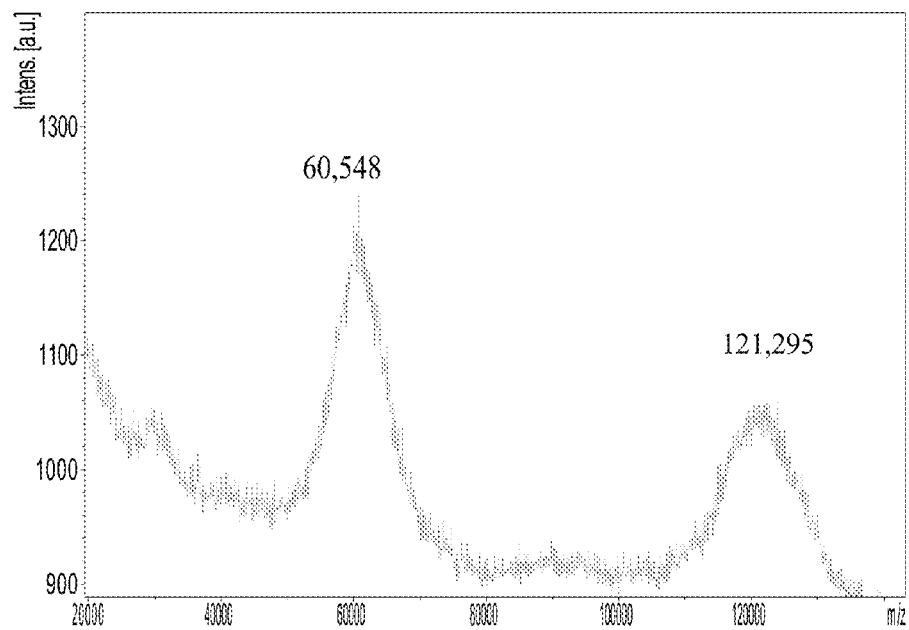

As shown in FIG. 24, reacting Replagal® α-GAL with bis-NHS-PEG$_{45}$ cross-linker increased the molecular weight of the Replagal® α-GAL dimer from 103.0 KDa to 121.3 KDa, as determined by MALDI-TOF mass spectrometry. The increase in molecular weight indicates an addition of approximately 9-10 molecules of bis-NHS-PEG$_{45}$ to the α-GAL dimer, which is similar to results described hereinabove for prh-α-GAL-I.

Example VII

Activity of Cross-Linked Mammalian Recombinant Human α-GAL

In order to determine whether the cross-linking of mammalian recombinant α-GAL described in Example VI affected enzymatic activity, the cross-linked α-GAL was assayed for its enzymatic activity using a p-nitrophenyl-α-D-galactopyranoside (pNP-G) assay, according to the procedures described hereinabove.

Figure 25:
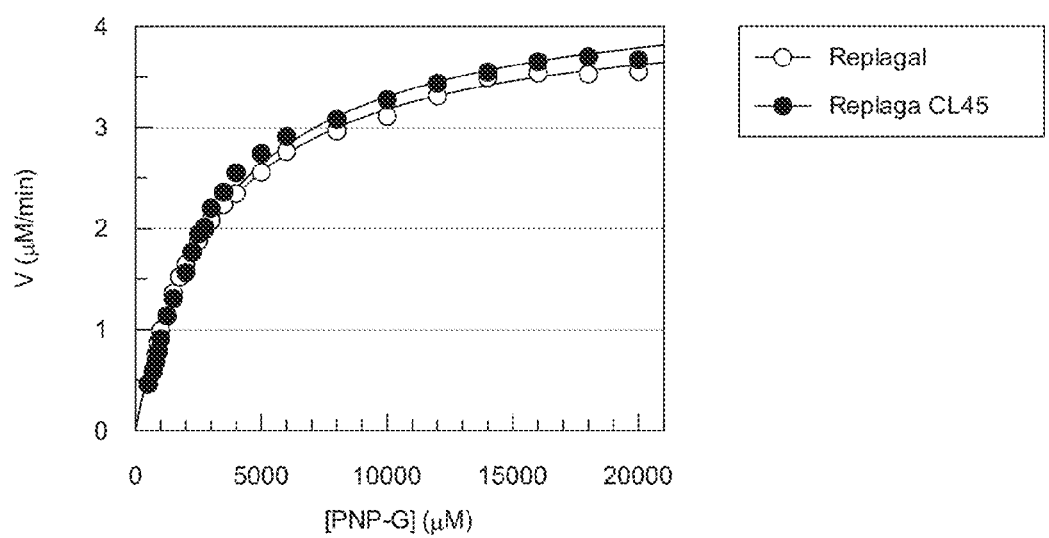
FIG. 25 is a Michaelis-Menten plot showing the velocity (V) of hydrolysis of p-nitrophenyl-α-D-galactopyranoside (pNP-G) by Replagal® mammalian recombinant human α-GAL (Replagal) and Replagal® mammalian recombinant human α-GAL cross-linked by bis-NHS-PEG$_{45}$ (Replagal CL45), as a function of pNP-G concentration.

As shown in FIG. 25 and in Table 3 below, mammalian recombinant human α-GAL which was cross-linked with bis-NHS-PEG$_{45}$ exhibited parameters of enzymatic activity which are very similar to those of native mammalian recombinant human α-GAL. These results indicate that the cross-linking did not significantly affect the activity or the catalytic machinery and mechanism of the mammalian recombinant human α-GAL.

TABLE 3

Activity results of cross-linked mammalian recombinant human α-GAL

| Sample | $K_M$ (μM) | $V_{max}$ (μM/minute) | $k_{cat}$ (second$^{-1}$) | $k_{cat}/K_M$ (second$^{-1}$ * μM$^{-1}$) |
|---|---|---|---|---|
| Replagal® α-GAL | 3212 ± 98 | 4.20 ± 0.05 | 67.2 ± 1 | 0.0209 ± 0.001 |
| Cross-linked Replagal® α-GAL | 3419 ± 162 | 4.43 ± 0.07 | 70.9 ± 1 | 0.0210 ± 0.001 |

Example VIII

In Vitro Stability of Cross-Linked Mammalian Recombinant Human α-GAL

The in vitro stability of the cross-linked Replagal® mammalian recombinant human α-GAL, obtained as described in Example VI, was measured in various conditions as described hereinabove in the Materials and Methods Section. The stability of non-cross-linked Replagal® α-GAL was measured for comparison, in order to assess the effect of cross-linking.

Figure 26A:
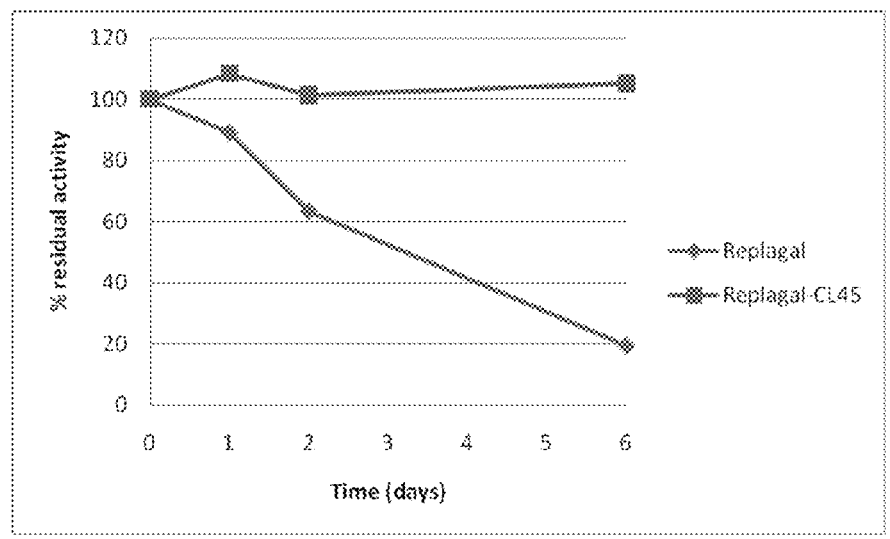
FIGS. 26A and 26B are graphs showing the activity of Replagal® mammalian recombinant human α-GAL (Replagal) and Replagal® mammalian recombinant human α-GAL cross-linked by bis-NHS-PEG$_{45}$ (Replagal-CL45) as a function of incubation time under simulated lysosomal conditions (citrate phosphate buffer, pH 4.6, 37° C.) (FIG. 26A) or in human plasma at 37° C.
Figure 26B:
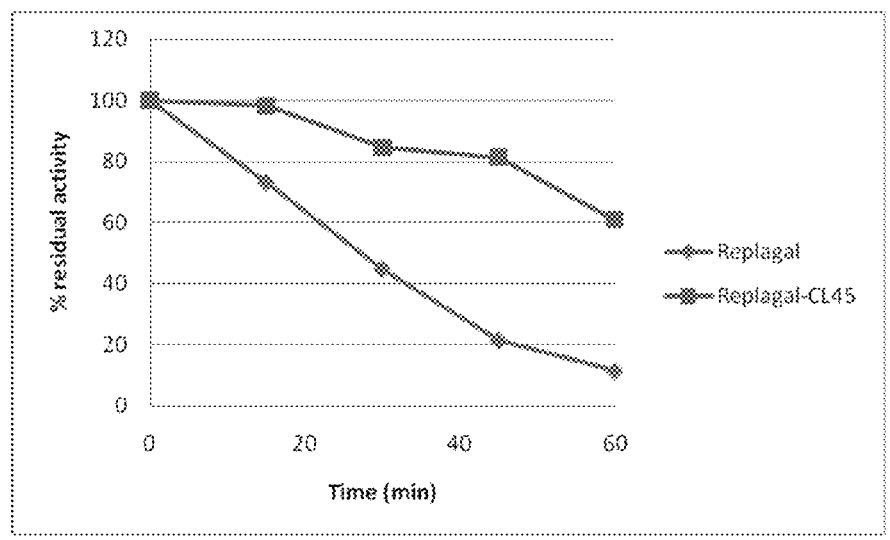
Figure 27A:
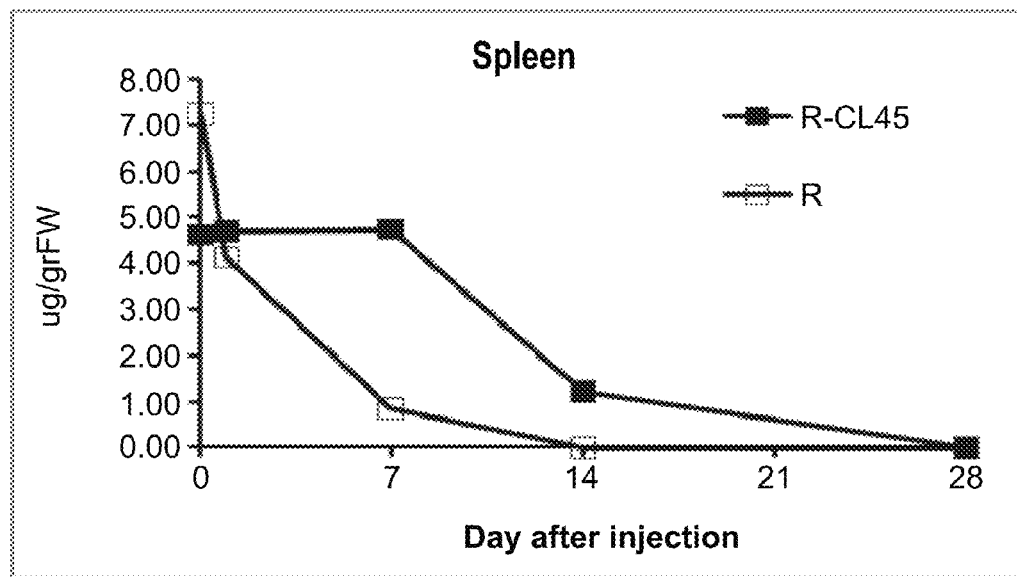
FIGS. 27A-27D are graphs showing the activity of Replagal® α-GAL (R) and Replagal® α-GAL cross-linked with bis-NHS-PEG$_{45}$ (R-CL45) in the spleens (FIG. 27A), livers (FIG. 27B), hearts (FIG. 27C) and kidneys (FIG. 27D) of Fabry mice 2 hours following injection of α-GAL.
Figure 27B:
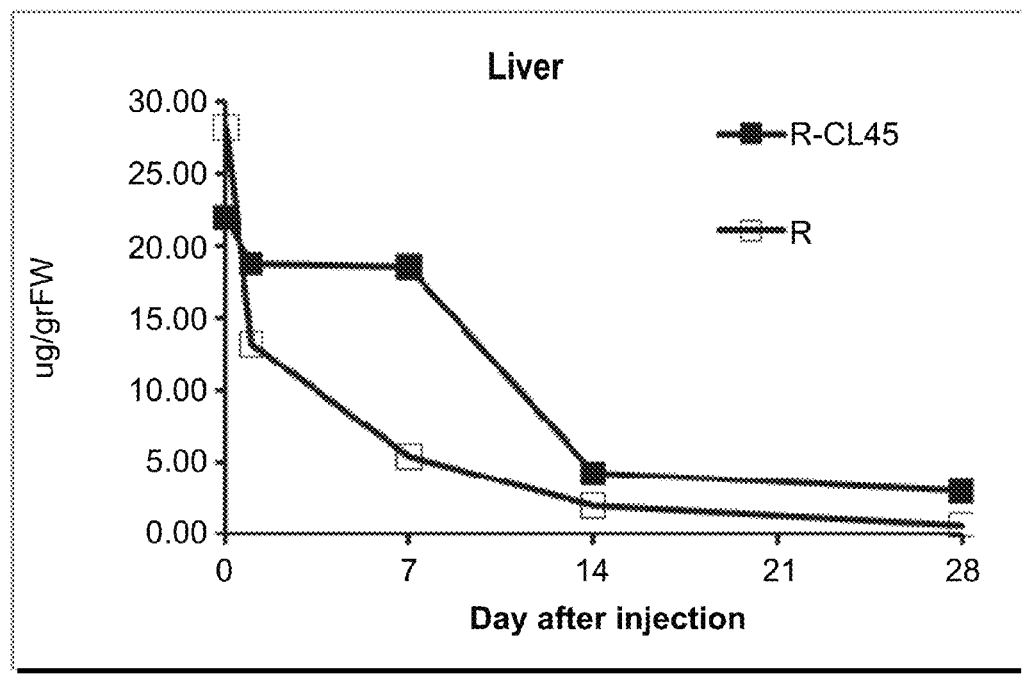
Figure 27C:
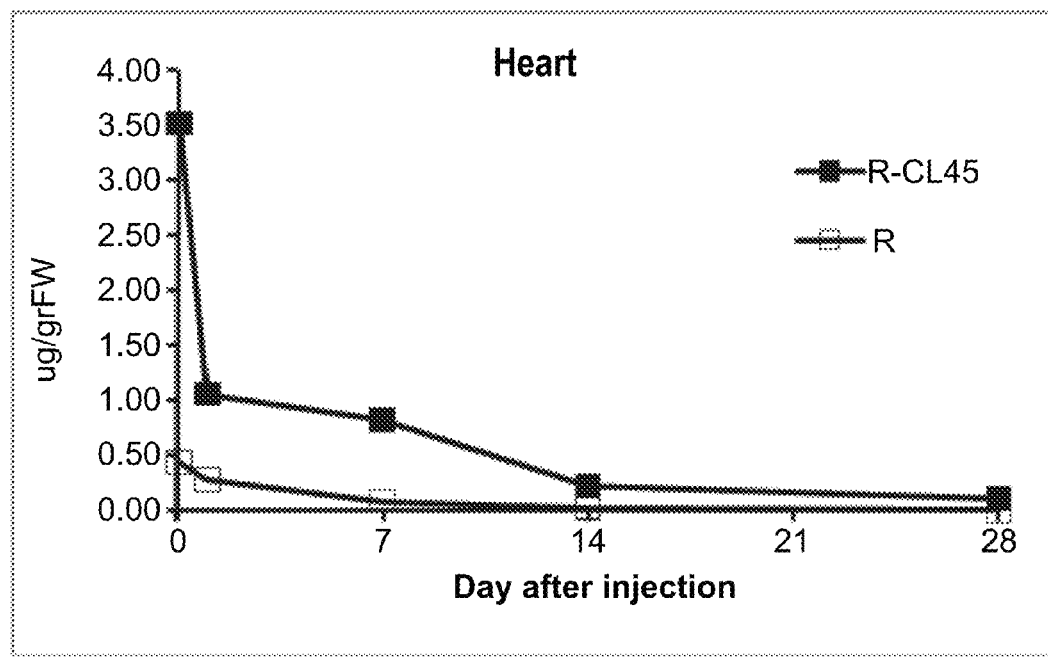
Figure 27D:
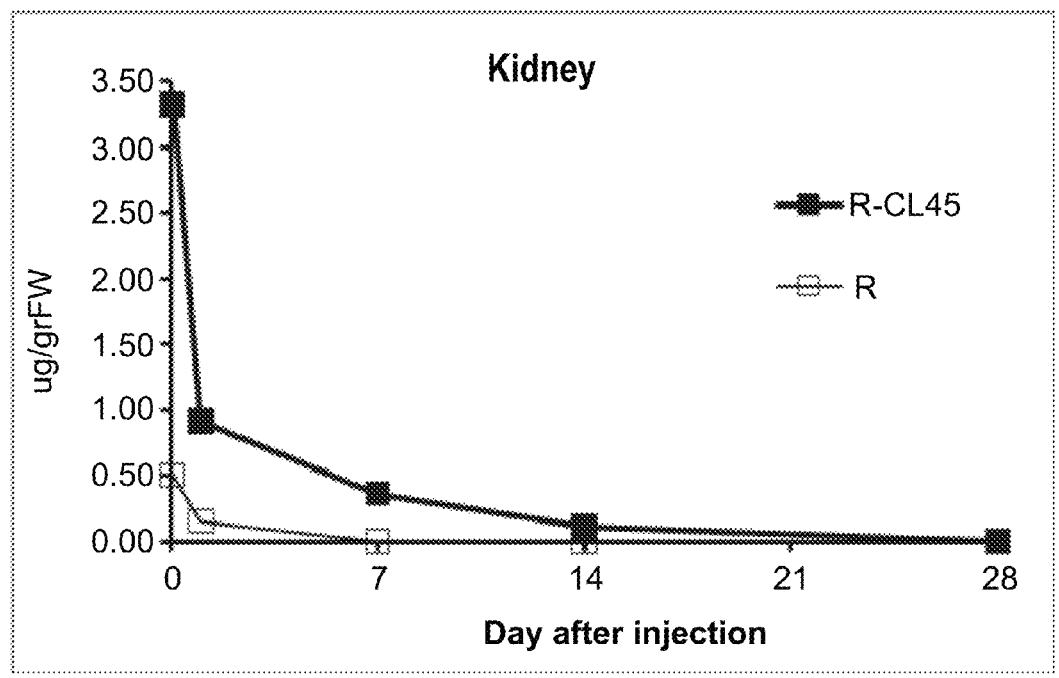

As shown in FIGS. 26A and 26B, the stability of mammalian recombinant human α-GAL under both simulated lysosomal conditions (FIG. 26A) and in human plasma (FIG. 26B) was considerably enhanced by cross-linking with bis-NHS-PEG$_{45}$. The cross-linked mammalian recombinant human α-GAL exhibited higher stability under simulated lysosomal conditions than in plasma.

These results indicate that the cross-linking of α-GAL as described herein can stabilize recombinant α-GAL from multiple sources and expression platforms.

Example IX

In Vivo Pharmacokinetics and Bio-Distribution of Cross-Linked Mammalian Recombinant Human α-GAL The pharmacokinetics and bio-distribution of the cross-linked mammalian recombinant human α-GAL described in Example VI was determined by measuring α-GAL activity in the spleen, liver, heart and kidneys of Fabry mice 2 hours, 7, 14, and 28 days post-injection, as well as Gb$_3$ levels in these organs, as described hereinabove in the Materials and Methods section. The bio-distribution of non-cross-linked Replagal® mammalian recombinant human α-GAL was determined for comparison.

As shown in FIGS. 27A-27D, the levels of cross-linked mammalian recombinant α-GAL in the spleens (FIG. 27A), liver (FIG. 27B), heart (FIG. 27C) and kidneys (FIG. 27D) of Fabry mice were considerably higher than those of non-cross-linked mammalian recombinant α-GAL.

Figure 28A:
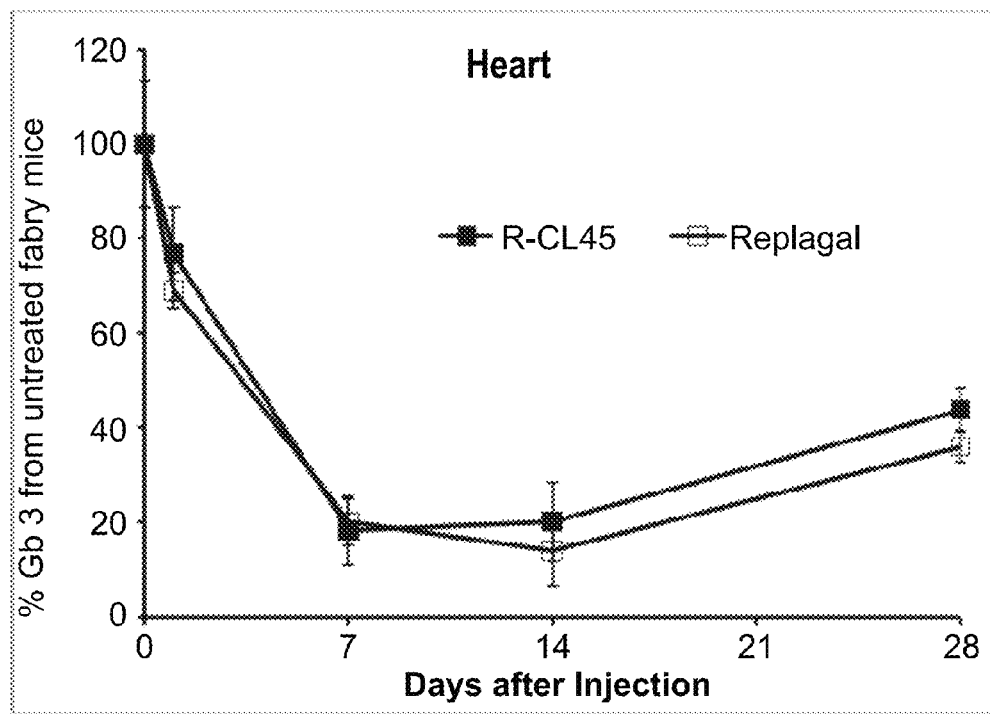
FIGS. 28A-28D are graphs showing Gb$_3$ levels in the hearts (FIG. 28A), kidneys (FIG. 28B), livers (FIG. 28C) and spleens (FIG. 28D) of Fabry mice, as a function of time following injection of Replagal® α-GAL (R) or Replagal® α-GAL cross-linked with bis-NHS-PEG$_{45}$ (R-CL45)
Figure 28B:
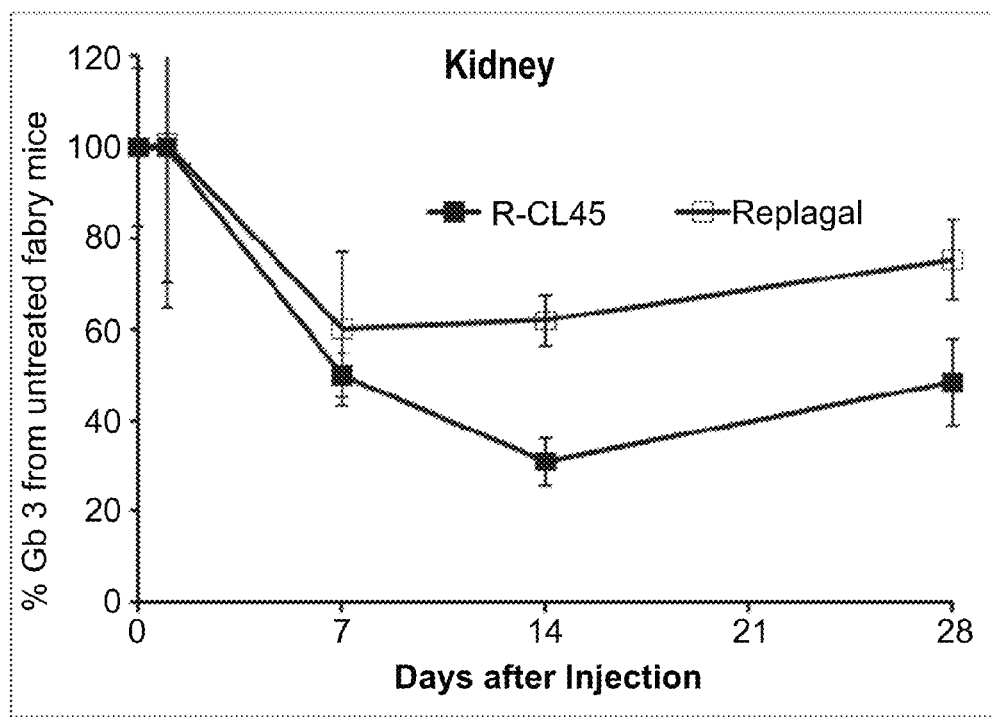
Figure 28C:
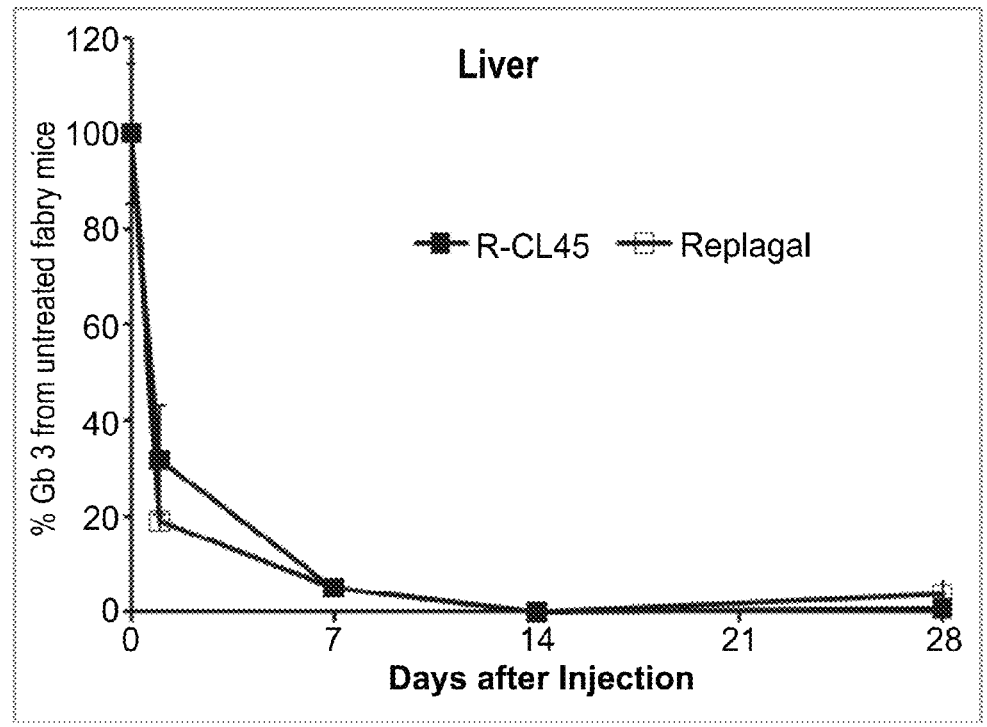
Figure 28D:
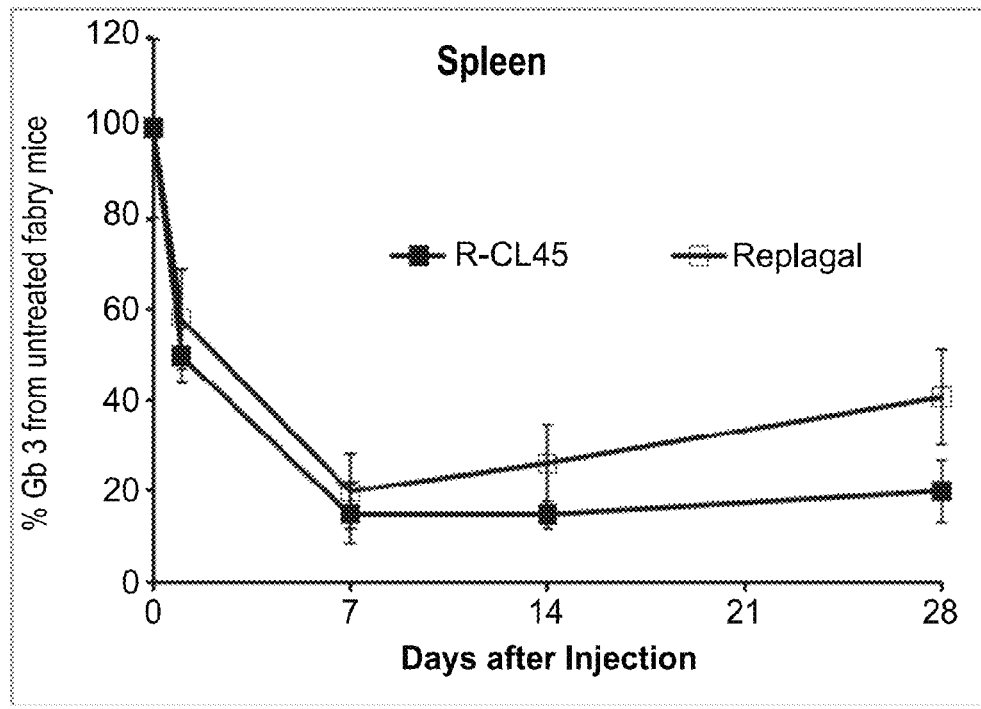

As shown in FIGS. 28A-28D, cross-linked mammalian recombinant α-GAL decreased $Gb_3$ levels in the heart (FIG. 28A), kidney (FIG. 28B), liver (FIG. 28C) and spleen (FIG. 28D) of Fabry mice, over the course of 28 days post-injection. Cross-linked mammalian recombinant α-GAL decreased $Gb_3$ levels to a greater extent than did non-cross-linked recombinant α-GAL in the kidney (FIG. 28B) and spleen (FIG. 28D) of Fabry mice, and to about the same extent as non-cross-linked mammalian recombinant α-GAL in the heart (FIG. 28A) and liver (FIG. 28C).

These results indicate that cross-linking with bis-NHS-PEG results in considerably enhanced uptake of recombinant α-GAL from a variety of sources and expression platforms into organs, including the kidney and heart, which are major target organs in the treatment of Fabry disorder. These results further indicate that cross-linking with bis-NHS-PEG results in a more substantial decrease of $Gb_3$ levels in organs.

Example X

Cross-Linking of Plant Recombinant Human α-GAL-II with Bis-N-Hydroxysuccinimide-poly (ethylene glycol) (bis-NHS-PEG)

Plant recombinant human α-GAL-II (prh-α-GAL-II), which lacks the amino acids EF present in the N-terminus of prh-α-GAL-I, was cross-linked with bis-NHS-$PEG_{45}$, bis-NHS-$PEG_{21}$, or bis-NHS-$PEG_{68}$ at a 200:1 molar ratio of bis-NHS-PEG to α-GAL, according to the protocol described in Example II.

The prh-α-GAL-II retained its biological activity following cross-linking with bis-NHS-PEG (data not shown).

The reaction products were analyzed by SDS-PAGE (sodium dodecyl sulfate-polyacrylamide gel electrophoresis) and MALDI-TOF mass spectrometry, as described hereinabove.

As shown in FIGS. 29A-29B, the standard native prh-α-GAL-II was observed as a monomer following gel electrophoresis, whereas following reaction of prh-α-GAL-II with bis-NHS-$PEG_{45}$ or bis-NHS-$PEG_{21}$ (FIG. 29A), or with bis-NHS-$PEG_{68}$ (FIG. 29B), prh-α-GAL-II appeared primarily in the form of a dimer (with some monomer present), indicating that the two monomers were covalently linked by cross-linking with a bis-NHS-PEG cross-linking agent.

As is further shown in FIGS. 29A-29B, for each of the tested cross-linkers, the molecular weight of the monomeric portion of prh-α-GAL-II increased following reaction with the cross-linker. The increase in molecular weight was greater for bis-NHS-$PEG_{45}$ than for bis-NHS-$PEG_{21}$ (FIG. 29A), and was greatest for bis-NHS-$PEG_{68}$ (compare FIG. 29A with FIG. 29B). These results indicate that the monomers which were not dimerized by cross-linking, were covalently attached to the bis-NHS-PEG cross-linker, i.e., the proteins were PEGylated.

As shown in FIGS. 30A-30C, reacting prh-α-GAL-II with bis-NHS-$PEG_{21}$ cross-linker increased the molecular weight of the prh-α-GAL-II dimer from 95 KDa (FIG. 30A) to 109 KDa (FIG. 30B), while reacting prh-α-GAL-II with bis-NHS-$PEG_{45}$ cross-linker increased the molecular weight of the prh-α-GAL-II dimer to 114 KDa (FIG. 30C), as determined by MALDI-TOF mass spectrometry. The increase in molecular weight indicates an addition of approximately 13 molecules of bis-NHS-$PEG_{21}$, or approximately 9 molecules of bis-NHS-$PEG_{45}$, to the prh-α-GAL-II dimer.

Example XI

In Vitro Stability of Cross-Linked Plant Recombinant Human α-GAL-II

The in vitro stability of the cross-linked plant recombinant human α-GAL-II (prh-α-GAL-II) obtained as described in Example X was measured under various conditions as described hereinabove in the Materials and Methods Section. The stability of Replagal® commercial recombinant human α-GAL was measured for comparison.

As shown in FIGS. 31A-31D, the stability of plant recombinant human α-GAL-II was enhanced by cross-linking with either bis-NHS-$PEG_{68}$ (FIGS. 31B and 31D), bis-NHS-$PEG_{45}$ (FIGS. 31A-31D) or bis-NHS-$PEG_{21}$ (FIGS. 31A and 31C), under both simulated lysosomal conditions (FIGS. 31A and 31B) and in human plasma (FIGS. 31C and 31D). The different cross-linkers enhanced the stability of prh-α-GAL-II to comparable extents. As further shown therein, the stability of the cross-linked prh-α-GAL-II was greater than the stability of the Replagal® recombinant human α-GAL. The cross-linked prh-α-GAL-II exhibited higher stability under simulated lysosomal conditions as well as under plasma conditions.

As further shown in FIGS. 31A-31D, non-cross-linked prh-α-GAL-II is considerably more stable than non-cross-linked prh-α-GAL-I (see FIGS. 1 and 3 for comparison), under both simulated lysosomal conditions (FIGS. 1 and 31A-31B) and in human plasma (FIGS. 3 and 31C-31D), although prh-α-GAL-II still exhibits some instability.

These results indicate that the cross-linking of α-GAL as described herein can stabilize different types of α-GALs.

Example XII

In Vivo Pharmacokinetics and Bio-Distribution of Cross-Linked Plant Recombinant Human α-GAL-II The pharmacokinetics and bio-distribution of the $PEG_{45}$-cross-linked and $PEG_{21}$-cross-linked plant recombinant human α-GAL-II (prh-α-GAL-II), described in Example X, was determined by measuring α-GAL activity in plasma and organs as described hereinabove in the Materials and Methods section. The pharmacokinetics and bio-distribution of non-cross-linked Replagal® mammalian recombinant human α-GAL were determined for comparison.

Blood samples were collected for pharmacokinetic analyses at 1, 5, 10, 30, 60, 120, 240, 480 and 1440 minutes after injection of Fabry mice with 1 mg/Kg of α-GAL.

Bio-distribution of α-GAL was determined by harvesting the liver, kidneys, heart and spleen of Fabry mice 2 hours, 7 days, 14 days and 28 days post-injection with 2 mg/Kg α-GAL.

As shown in FIGS. 32A and 32B and in Table 4, cross-linking of prh-α-GAL-II with bis-NHS-$PEG_{45}$ considerably increased the circulatory terminal half-life of prh-α-GAL-II, yielding a circulatory half-life considerably greater than that of mammalian recombinant α-GAL or of non-cross-linked prh-α-GAL-II.

TABLE 4

Circulatory terminal half-life of recombinant α-GAL

| Test item | $t_{1/2}$ (min) |
|---|---|
| Replagal ® α-GAL | 13.3 |
| plant recombinant alpha-GAL-II | 4.8 |
| plant recombinant alpha-GAL-II cross-linked with bis-NHS-PEG$_{45}$ | 581.6 |

As shown in FIGS. 33A-33L, cross-linking of prh-α-GAL-II with bis-NHS-PEG$_{45}$ increased the uptake of prh-α-GAL-II in heart (FIG. 33A), kidney (FIG. 33B), liver (FIG. 33C) and spleen (FIG. 33D) of Fabry mice, although to a lesser degree in the liver.

As shown in FIGS. 33E-33L, cross-linking of prh-α-GAL-II with bis-NHS-PEG$_{21}$ also increased the uptake of prh-α-GAL-II in heart (FIGS. 33E and 33I), kidney (FIGS. 33F and 33J), liver (FIGS. 33G and 33K) and spleen (FIGS. 33H and 33L) of Fabry mice, although such an increase was not always evident after only 2 hours.

Figure 33A:
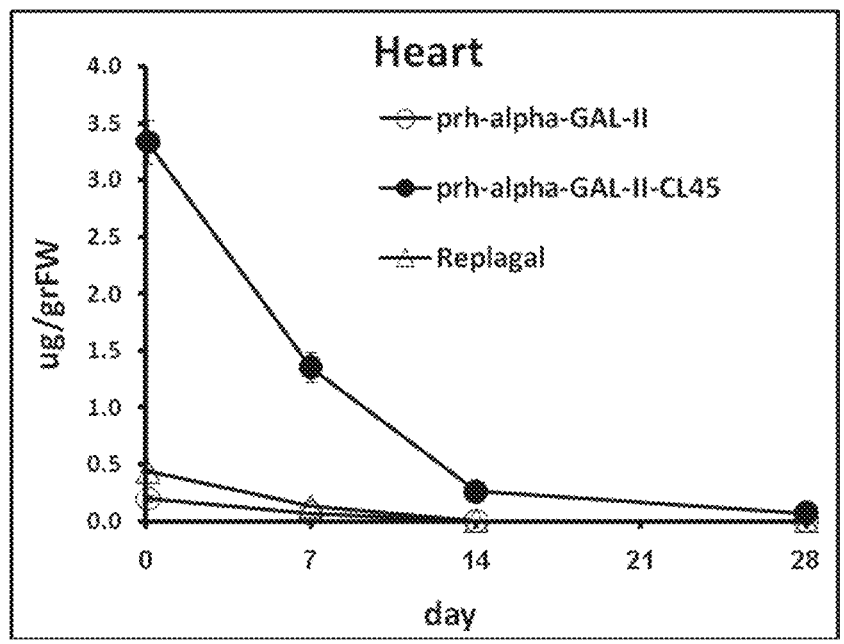
Figure 33B:
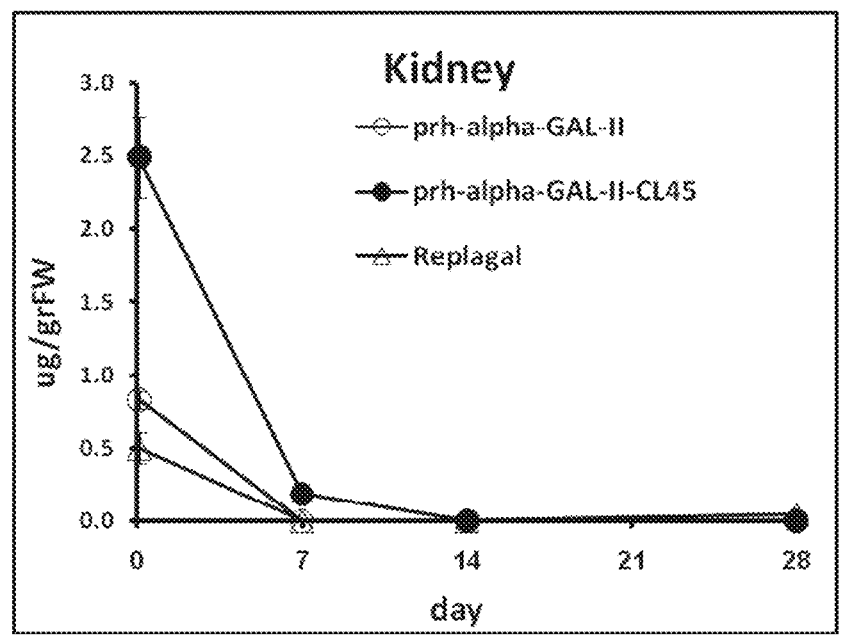
Figure 33C:
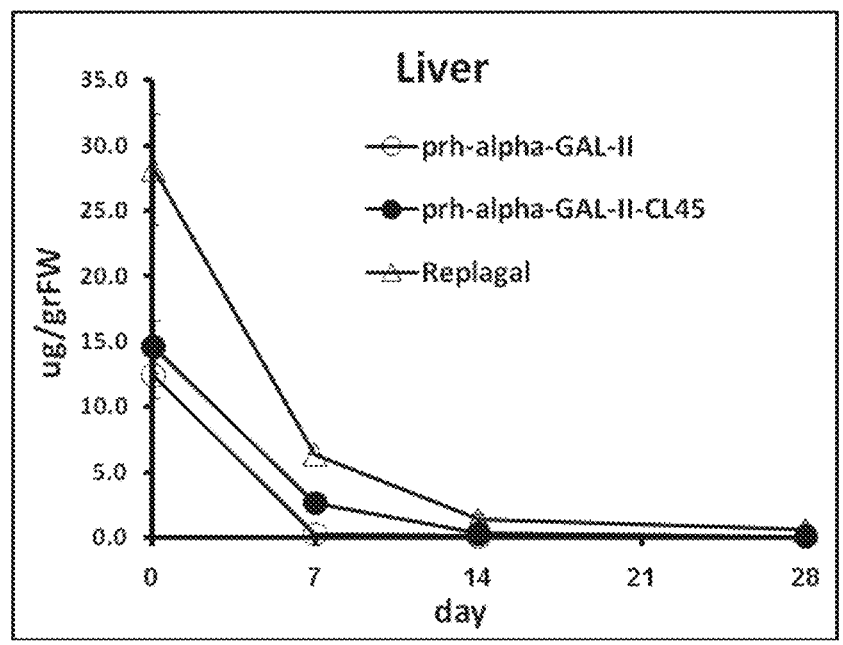
Figure 33D:
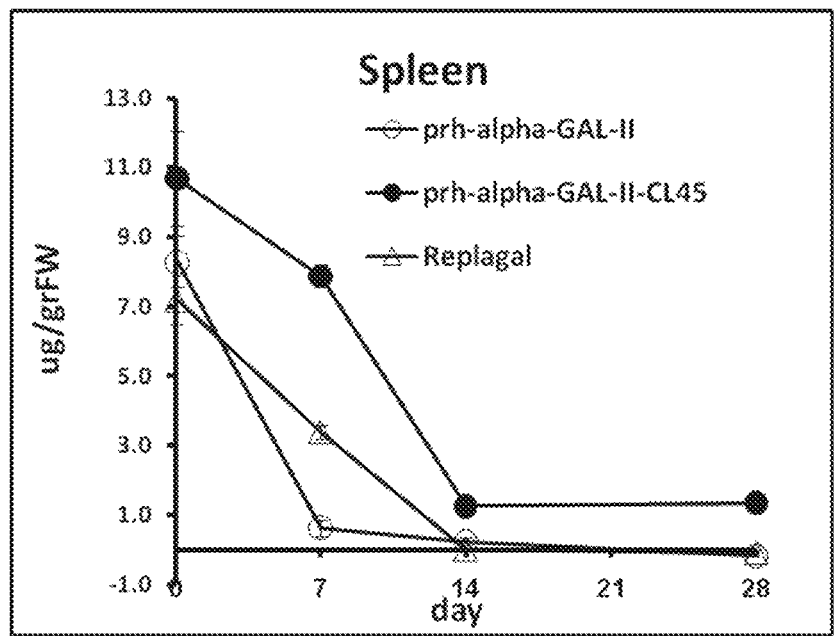
Figure 33E:
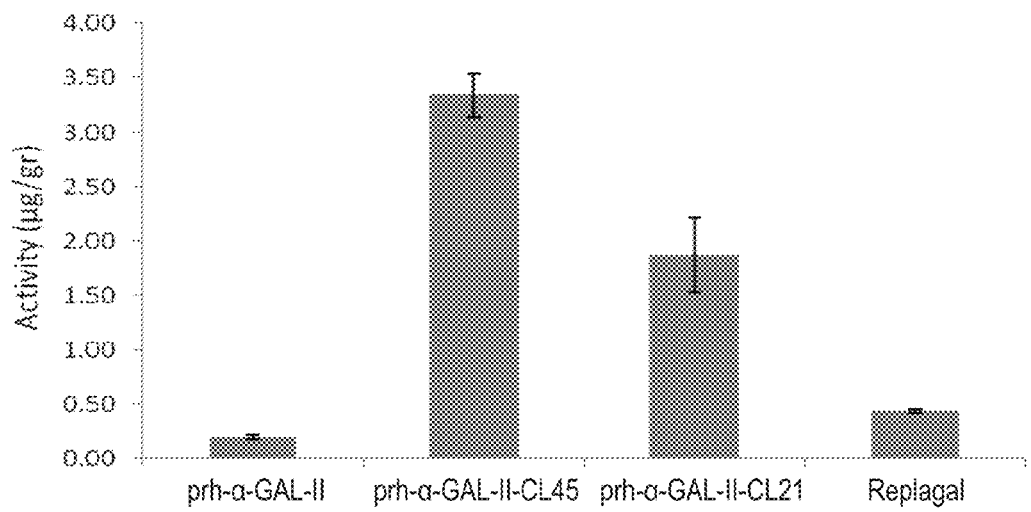
Figure 33F:
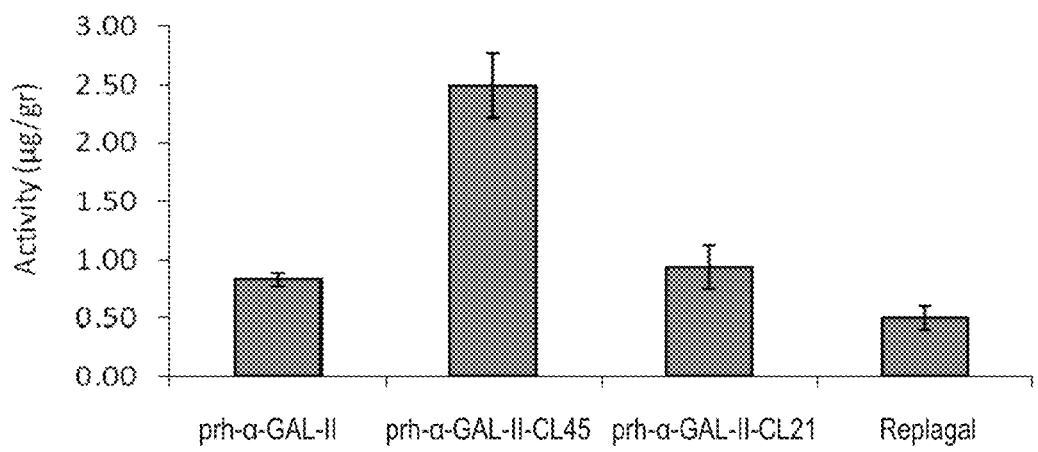
Figure 33G:
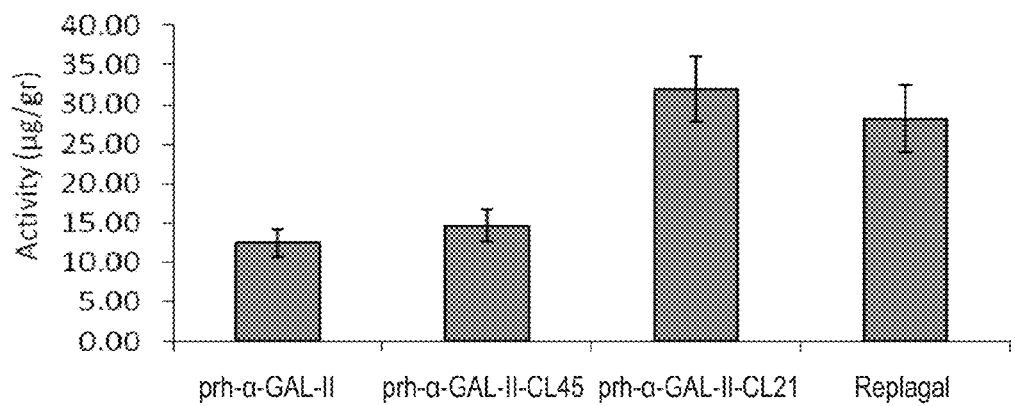
Figure 33H:
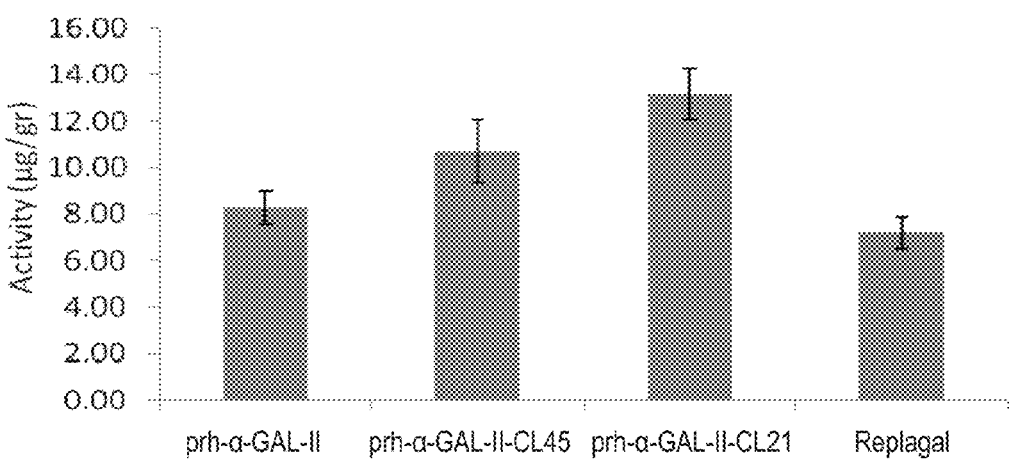
Figure 33I:
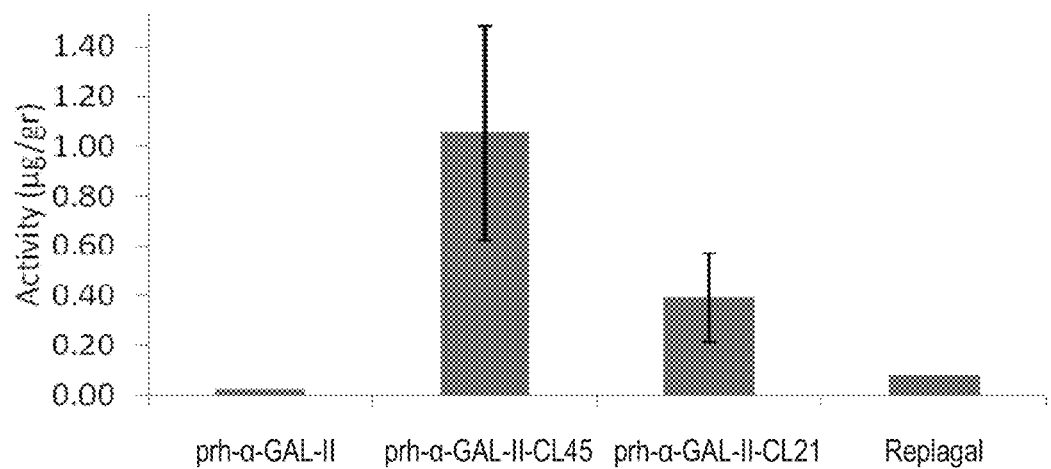
Figure 33J:
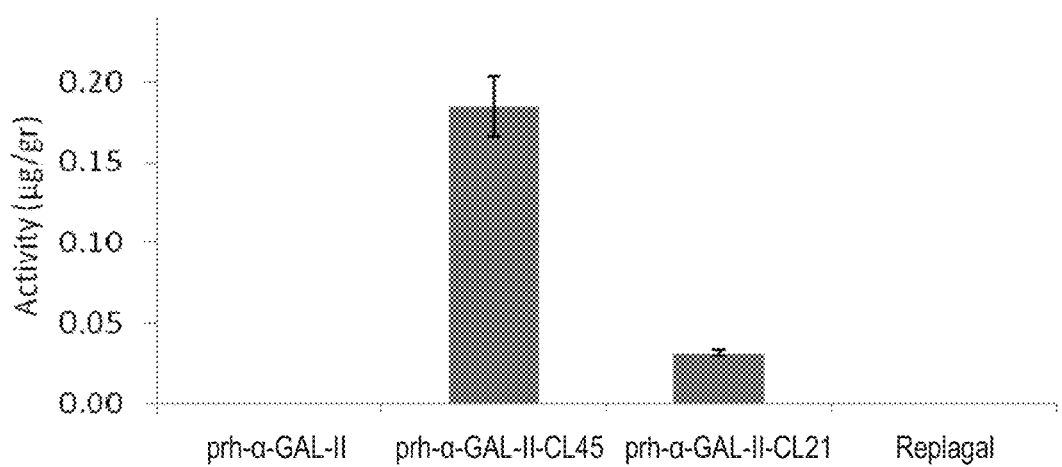
Figure 33K:
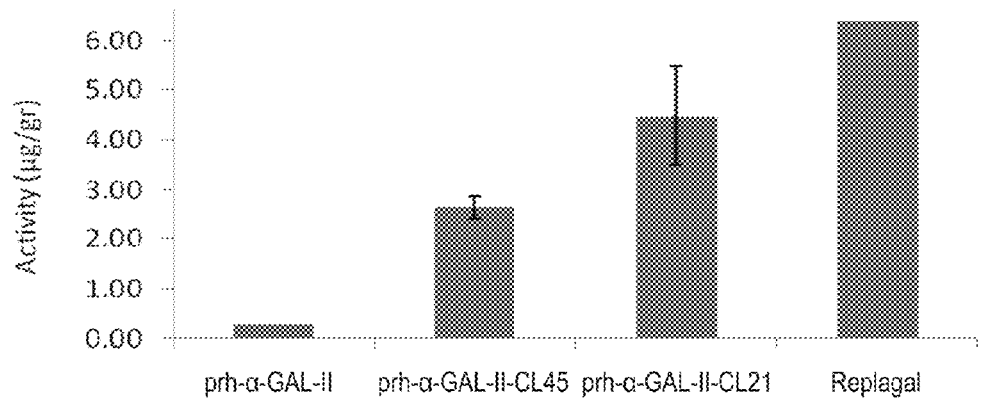
Figure 33L:
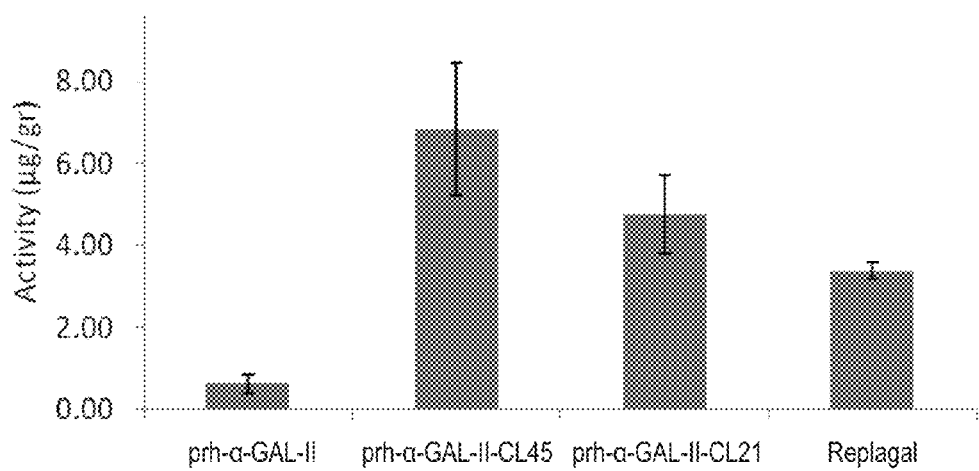

As further shown therein, the levels of cross-linked prh-α-GAL-II were greater than the levels of mammalian recombinant α-GAL in the heart (FIGS. 33A, 33E and 33I), kidney (FIGS. 33B, 33F and 33J), and spleen (FIGS. 33D, 33H and 33L) of Fabry mice, and lower than the levels of mammalian recombinant α-GAL in the liver (FIGS. 33C, 33G and 33K).

These results indicate that cross-linked prh-α-GAL-II exhibits considerably enhanced activity of α-GAL in the plasma and in various organs, particularly in organs other than the liver.

Example XIII

Effect of pH on Activity of Plant Recombinant Human α-GAL

The pH of the environment has a significant effect on the stability and kinetics of lysosomal enzymes such α-GAL. The pH may affect binding of substrate to the enzyme. The pH can also affect the protonation or deprotonation of catalytic groups, such as carboxyl or amino groups, which are part of the enzyme's active site, and thus affect the kinetic behavior of the enzyme. The stability of the tertiary or quaternary structure of enzymes is also pH-dependent, and affects the velocity of the enzymatic reaction, especially at extremely acidic or alkaline pH values.

The activity of PEG$_{45}$-cross-linked and non-cross-linked plant recombinant human α-GAL-II was determined at various pH values using a pNP-G substrate, in order to examine the pH-dependence of α-GAL activity, and the effect of cross-linking thereon. The measurements were performed in solutions of 20 mM citrate and 30 mM sodium phosphate.

The kinetic parameters characterizing α-GAL activity at various pH values are summarized in Table 5 below, and in FIGS. 34A-34C.

As shown in FIGS. 34A-34C, cross-linking of the α-GAL-II increased the $V_{max}$ (FIG. 34A) and $k_{cat}$ (FIG. 34C) parameters, and did not have a significant effect on the $K_M$ parameter (FIG. 34B).

TABLE 5

Activity results of non-cross-linked plant recombinant human α-GAL-II (prh-α-GAL-II) and PEG$_{45}$-cross-linked plant recombinant human α-GAL II (prh-α-GAL-II-CL45) at various pH values

| pH | Sample | $K_M$ (µM) | $V_{max}$ (µM/minute) | $k_{cat}$ (second$^{-1}$) | $k_{cat}/K_M$ (second$^{-1}$ * µM$^{-1}$) |
|---|---|---|---|---|---|
| 2.8 | prh-α-GAL-II | 15216 | 0.57 | 9.04 | 0.0006 |
| | prh-α-GAL-II-CL45 | 13618 | 0.90 | 14.37 | 0.0011 |
| 3.2 | prh-α-GAL-II | 11476 | 0.55 | 8.85 | 0.0008 |
| | prh-α-GAL-II-CL45 | 8489 | 1.34 | 21.44 | 0.0025 |
| 3.6 | prh-α-GAL-II | 11147 | 1.76 | 28.16 | 0.0025 |
| | prh-α-GAL-II-CL45 | 4699 | 2.23 | 35.68 | 0.0076 |
| 4.04 | prh-α-GAL-II | 5709 | 1.98 | 31.68 | 0.0055 |
| | prh-α-GAL-II-CL45 | 3207 | 2.74 | 43.76 | 0.0136 |
| 4.4 | prh-α-GAL-II | 4596 | 2.40 | 38.40 | 0.0084 |
| | prh-α-GAL-II-CL45 | 3122 | 3.22 | 51.57 | 0.0165 |
| 4.8 | prh-α-GAL-II | 4531 | 2.32 | 37.12 | 0.0082 |
| | prh-α-GAL-II-CL45 | 3345 | 2.95 | 47.23 | 0.0141 |
| 5.29 | prh-α-GAL-II | 6793 | 2.06 | 32.99 | 0.0049 |
| | prh-α-GAL-II-CL45 | 3973 | 2.78 | 44.48 | 0.0112 |
| 5.66 | prh-α-GAL-II | 10396 | 1.75 | 28.05 | 0.0027 |
| | prh-α-GAL-II-CL45 | 4883 | 2.70 | 43.20 | 0.0088 |
| 6.09 | prh-α-GAL-II | 11357 | 1.44 | 23.04 | 0.0020 |
| | prh-α-GAL-II-CL45 | 8336 | 1.54 | 24.59 | 0.0030 |
| 6.4 | prh-α-GAL-II | 21046 | 1.32 | 21.12 | 0.0010 |
| | prh-α-GAL-II-CL45 | 16844 | 1.46 | 23.36 | 0.0014 |
| 6.76 | prh-α-GAL-II | 25188 | 1.12 | 17.92 | 0.0007 |
| | prh-α-GAL-II-CL45 | 18313 | 1.14 | 18.24 | 0.0010 |
| 7.36 | prh-α-GAL-II | — | — | — | — |
| | prh-α-GAL-II-CL45 | 32692 | 0.52 | 8.37 | 0.0003 |

The enhancement of the $V_{max}$ and $k_{cat}$ parameters indicates an increase in catalytic activity. This increase is particularly significant at pH values of at least about 7, where the catalytic activity of non-cross-linked α-GAL-II is negligible.

$K_M$ is a kinetic parameter associated with enzyme/substrate affinity. The absence of a significant effect of cross-linking on $K_M$ values indicates that the cross-linking has no significant effect on α-GAL affinity to the pNP-G substrate.

Example XIV

Effect of PEGylation on Stability of α-GAL

The effect of PEGylation per se on α-GAL stability was ascertained, in order to determine whether the stabilizing effect of PEG cross-linkers is due to the properties of PEG or due to the cross-linking.

Plant recombinant human α-GAL-I was reacted with N-hydroxysuccinimide (NHS)-activated methoxy-capped PEGs with different molecular weights (2, 5, and 10 KDa). Such PEG reagents have a single NHS group, and consequently PEGylate the protein without forming cross-linking. The reaction products were analyzed by SDS-PAGE.

As shown in FIG. 35, the methoxy-capped PEGylating agents PEGylated the α-GAL (visible as an increase in molecular weight of the α-GAL), but did not substantially generate α-GAL dimers, indicating that the α-GAL was not cross-linked.

As shown in FIGS. 36A and 36B, PEGylating plant recombinant human α-GAL-I without forming cross-linking did not substantially increase the stability of the plant recombinant α-GAL, under either simulated lysosomal conditions (FIG. 36A) or in human plasma (FIG. 36B).

These results indicate that the stabilizing effect of the cross-linking described hereinabove is not a result of PEGylation per se.

Example XV

Effect of PEG Chain Length on Activity of Cross-Linked α-GAL

In order to assess the effect of the chain length of PEG cross-linkers on α-GAL activity, plant recombinant human α-GAL-I was cross-linked with bis-NHS-PEG$_2$, bis-NHS-PEG$_4$, bis-NHS-PEG$_{68}$ and bis-NHS-PEG$_{150}$ agents, using essentially the same procedures as described in Example II (PEG$_{68}$ and PEG$_{150}$ are approximate chain lengths). The α-GAL-I was cross-linked at 50:1, 100:1 and 200:1 bis-NHS-PEG:α-GAL molar ratios. The reaction products were analyzed by SDS-PAGE, as described hereinabove. α-GAL-I cross-linked with bis-NHS-PEG$_{45}$ as described in Example II was also analyzed for comparison.

As shown in FIG. 37, SDS-PAGE analysis showed that all of the bis-NHS-PEG agents cross-linked the α-GAL so as to result in a covalently cross-linked dimer, and that cross-linking was more efficient when a 200:1 molar ratio was used.

The enzymatic activity of the cross-linked α-GAL-I was then determined as described in Example III. The results are summarized in Table 6 below.

TABLE 6

Activity results of cross-linked plant recombinant human α-GAL-I

| Reagent | Molar ratio (reagent:α-GAL-I) | Expected α-GAL activity [mg/mL] | Measured α-GAL activity [mg/mL] |
|---|---|---|---|
| bis-NHS—PEG$_2$ | 50:1 | 2 | 1.159 |
|  | 100:1 | 2 | 1.001 |
|  | 200:1 | 2 | 0.970 |
| bis-NHS—PEG$_4$ | 50:1 | 2 | 1.399 |
|  | 100:1 | 2 | 1.333 |
|  | 200:1 | 2 | 1.048 |
| bis-NHS—PEG$_{68}$ | 50:1 | 2 | 1.822 |
|  | 100:1 | 2 | 2.252 |
|  | 200:1 | 2 | 2.425 |
| bis-NHS—PEG$_{150}$ | 50:1 | 2 | 1.804 |
|  | 100:1 | 2 | 2.031 |
|  | 200:1 | 2 | 1.825 |

As shown in Table 6, cross-linking with PEG$_2$ and PEG$_4$ moderately reduced α-GAL activity (by approximately 30-50%), whereas cross-linking with longer PEG chains did not significantly affect α-GAL activity.

These results indicate that cross-linking with PEG chains longer than PEG$_4$ is advantageous in terms of preserving activity of the cross-linked α-GAL.

Example XVI

Cross-Linking of α-GAL Using bis-COOH-PEG Agents

As an alternative to the above-described cross-linking of α-GAL using pre-prepared (e.g., commercially available) bis-NHS-PEG agents, α-GAL was cross-linked with bis-COOH-PEG agents by activating the carboxyl (i.e., COOH) groups in situ shortly before the cross-linking reaction was effected.

Bis-COOH-PEG$_{12}$, bis-COOH-PEG$_{28}$ and bis-COOH-PEG$_{45}$ were each activated by being reacted with 1.1 molar equivalents per carboxyl group (i.e., 2.2 molar equivalents per bis-COOH-PEG) of both NHS (N-hydroxysuccinimide) and EDC (1-ethyl-3-(3-dimethylaminopropyl)carbodiimide). The reaction mixture was then shaken in DMSO for 30 minutes at room temperature. The activated bis-COOH-PEG, which is essentially bis-NHS-PEG, was then reacted with plant recombinant human α-GAL-I at molar ratios of 50:1, 100:1 and 200:1, as described in Example II. The reaction products were analyzed by SDS-PAGE, as described hereinabove. α-GAL-I cross-linked with bis-NHS-PEG$_{45}$ as described in Example II was also analyzed for comparison.

As shown in FIG. 38, SDS-PAGE analysis showed that all of the bis-COOH-PEG agents cross-linked the α-GAL to some extent, but that cross-linking was more efficient when a 200:1 molar ratio was used.

The enzymatic activity of the cross-linked α-GAL-I was then determined as described in Example III. The results are summarized in Table 7 below.

TABLE 7

Activity results of cross-linked plant recombinant human α-GAL-I

| Reagent | Molar ratio (reagent:α-GAL-I) | Expected α-GAL activity [mg/mL] | Measured α-GAL activity [mg/mL] |
|---|---|---|---|
| Bis-HOOC-PEG$_{12}$ | 50:1 | 1.5 | 1.236 |
|  | 100:1 | 1.5 | 1.304 |
|  | 200:1 | 1.5 | 1.404 |
| Bis-HOOC-PEG$_{28}$ | 50:1 | 1.5 | 1.326 |
|  | 100:1 | 1.5 | 1.371 |
|  | 200:1 | 1.5 | 1.460 |
| Bis-HOOC-PEG$_{45}$ | 50:1 | 1.5 | 1.349 |
|  | 100:1 | 1.5 | 1.541 |
|  | 200:1 | 1.5 | 1.628 |

As shown in Table 7, cross-linking with each of the tested bis-COOH-PEG agents resulted in α-GAL with about the expected activity.

These results indicate that cross-linking bis-COOH-PEG agents does not reduce α-GAL activity in comparison to cross-linking with bis-NHS-PEG agents.

These results further confirm the above-described findings that cross-linking with PEG chains longer than $PEG_4$ does not significantly reduce the activity of the cross-linked α-GAL.

Example XVII

Effect of Length and Type of Cross-Linking Agent on In Vitro Stability of Cross-Linked Plant Recombinant Human α-GAL-I In order to further characterize the effect of chain length on cross-linked α-GAL stability, and to compare the stability of α-GAL cross-linked with bis-COOH-PEG agents (e.g., as described in Example XVI) with that of α-GAL cross-linked with bis-NHS-PEG agents, the in vitro stability of plant recombinant human α-GAL-I (prh-α-GAL-I) cross-linked with bis-NHS-$PEG_2$, bis-NHS-$PEG_4$, bis-COOH-$PEG_{12}$, bis-$COOH_{28}$, and bis-COOH-$PEG_{45}$, obtained as described in Examples XV and XVI, was measured in various conditions as described hereinabove in the Materials and Methods Section, and compared with the stability of prh-α-GAL-I cross-linked with bis-NHS-$PEG_{45}$ as described in Example II. The stability of Replagal® commercial recombinant human α-GAL and non-crosslinked prh-GAL-I was measured for comparison.

As shown in FIG. 39, the stability of plant recombinant human α-GAL-I under simulated lysosomal conditions was enhanced by cross-linking with each of the bis-NHS-PEG and bis-COOH-PEG agents.

As further shown therein, the stability of the cross-linked prh-α-GAL-I was correlated with the length of the cross-linking PEG chain, with bis-NHS-$PEG_{45}$ and bis-COOH-$PEG_{45}$ providing the most stability, and bis-NHS-$PEG_2$ providing the least stability. However, cross-linking with bis-COOH-$PEG_{45}$ provided only marginally more stability than did cross-linking with bis-COOH-$PEG_{45}$, suggesting that above a certain length, the stability is not affected by PEG chain length.

As further shown in FIG. 39, cross-linking with bis-NHS-$PEG_{45}$ provided slightly more stability than did cross-linking with bis-COOH-$PEG_{45}$. This may be a result of incomplete activation of the bis-COOH-PEG agent. However the difference in stability was slight.

In addition, cross-linking with each of the bis-NHS-PEG and bis-COOH-PEG agents enhanced the stability of the plant recombinant human α-GAL-I in human plasma at 37° C. (data not shown).

These results provide further evidence that cross-linking α-GAL as described herein can increase the efficacy of α-GAL in vivo by increasing the stability of α-GAL in lysosomes and in the blood, and that PEG chains of about 28-45 units in length are more effective at stabilizing α-GAL by cross-linking than are shorter PEG chains.

Example XVIII

Kinetic Parameters of Cross-Linked Plant Recombinant Human α-Gal-II

The kinetic parameters of cross-linked plant recombinant human α-GAL-II, obtained as described in Example X, as well as of non-cross-linked plant recombinant human α-GAL-II, were determined using a pNP-G substrate and Michaelis-Menten analysis, in order to examine the effect of cross-linking thereon. The measurements were performed in a solution of 20 mM citrate, 30 mM sodium phosphate, 0.1% bovine serum albumin and 0.67% ethanol, at a pH of 4.6. The kinetic parameters were calculated using protein content values based on an activity assay.

As shown in Table 8 below, cross-linking of α-GAL-II resulted in improved kinetic properties, as compared with non-cross-linked α-GAL-II. The Michaelis constant ($K_M$) was reduced, indicating higher affinity of the enzyme to the substrate. Furthermore, the $k_{cat}/K_M$, which signifies the overall catalytic efficiency of the enzyme with this substrate under the described conditions, was enhanced for the cross-linked species.

TABLE 8

Michaelis-Menten parameters of non-cross-linked plant recombinant human α-GAL-II (prh-α-GAL-II) and plant recombinant human α-GAL II cross-linked with bis-NHS-$PEG_{21}$ (prh-α-GAL-II-CL21), bis-NHS-$PEG_{45}$ (prh-α-GAL-II-CL45) or bis-NHS-$PEG_{68}$ (prh-α-GAL-II-CL68)

| Sample | $K_m$ (μM) | $V_{max}$ (μM/min) | $k_{cat}$ (sec$^{-1}$) | $k_{cat}/K_m$ (sec$^{-1}$ μM$^{-1}$) |
|---|---|---|---|---|
| prh-α-GAL-II | 4801 | 4.59 | 73.49 | 0.015 |
| prh-α-GAL-II-CL21 | 2661 | 4.85 | 77.55 | 0.029 |
| prh-α-GAL-II-CL45 | 2583 | 4.87 | 77.87 | 0.030 |
| prh-α-GAL-II-CL68 | 2556 | 4.12 | 65.97 | 0.026 |

Example XIX

Reproducibility of Cross-Linking of Plant Recombinant Human α-Gal-II

The batch-to-batch reproducibility of cross-linking was assessed after preparing 5 batches of plant recombinant human α-GAL-II (prh-α-GAL-II) cross-linked with bis-NHS-$PEG_{45}$ at a 200:1 ratio, using procedures similar to those described in Example II.

In batches 1, 2, 4 and 5, 1 mg of prh-α-GAL-II was reacted with 3.98 mg bis-NHS-PEG.

In batch 3, 20.5 mg of prh-α-GAL-II was reacted with 80.7 mg bis-NHS-PEG.

The enzymatic activity of the cross-linked prh-α-GAL-II was determined as described in Example III. The results are summarized in Table 9 below.

TABLE 9

Activity results of cross-linked plant recombinant human α-GAL-II from different batches

| Batch no. | Expected α-GAL activity [mg/mL] | Measured α-GAL activity [mg/mL] |
|---|---|---|
| 1 | 1.25 | 1.38 |
| 2 | 1.25 | 1.23 |
| 3 | 1.43 | 1.4 |
| 4 | 1.25 | 0.85 |
| 5 | 1.25 | 1.11 |

As shown in Table 9, the measured activity was close to the expected activity in all 5 batches. In 4 of the 5 batches, the measured activity differed from the expected activity by about 10% or less.

These results indicate that the obtained activity of the cross-linked prh-α-GAL-II is relatively predictable and reproducible.

The stability of the cross-linked prh-α-GAL-II under lysosomal conditions and in human plasma was determined as described hereinabove.

As shown in FIGS. 40A and 40B, the stability of the cross-linked prh-α-GAL-II exhibited good reproducibility under both simulated lysosomal conditions and in human plasma.

The cross-linking was also analyzed by SDS-PAGE analysis, IEF (isoelectric focusing) analysis, and MALDI-TOF mass spectrometry, as described hereinabove. Non-cross-linked prh-α-GAL-II was analyzed for comparison.

As shown in FIG. 41, the cross-linked prh-α-GAL-II from the different batches exhibited the same degree of covalent dimerization under SDS-PAGE analysis.

As shown in FIG. 42, the cross-linked prh-α-GAL-II from the different batches exhibited the same isoelectric points under IEF analysis.

As shown in FIGS. 43A-43F, the cross-linked prh-α-GAL-II from batches 1-5 (FIGS. 43B-43F, respectively) all exhibited an increase of approximately 20-21 KDa in the dimer form, as compared to the non-cross-linked prh-α-GAL-II (FIG. 43A). Such an increase corresponds to about 10 PEG molecules per α-GAL dimer. As further shown in FIGS. 43B-43F, the cross-linked prh-α-GAL-II from the different batches exhibited similar proportions of monomer vs. dimer.

These results further indicate that good reproducibility in cross-linking of α-GAL.

The kinetic parameters of the cross-linked prh-α-GAL-II were determined using a pNP-G substrate and Michaelis-Menten analysis, in order to examine the reproducibility of enzymatic activity. The measurements were performed in a solution of 20 mM citrate, 30 mM sodium phosphate, 0.1% bovine serum albumin and 0.67% ethanol, at a pH of 4.6. The kinetic parameters were calculated using protein content values based on optical density at 280 nm.

As shown in FIG. 44, the cross-linked prh-α-GAL-II from the different batches exhibited similar profiles of catalytic velocity vs. substrate concentration.

As shown in Table 10 below, the cross-linked prh-α-GAL-II from the different batches exhibited good reproducibility of the $V_{max}$ and $k_{cat}$ parameters. The $K_m$ parameter varied more between batches, although this may be an artifact of the protein quantification.

The above results indicate good reproducibility in the enzymatic properties of cross-linked α-GAL.

TABLE 10

Michaelis-Menten parameters of plant recombinant human α-GAL II cross-linked with bis-NHS-PEG$_{45}$ in different batches

| Batch no. | $K_m$ (μM) | $V_{max}$ (μM/min) | $k_{cat}$ (sec$^{-1}$) | $k_{cat}/K_m$ (sec$^{-1}$ μM$^{-1}$) |
|---|---|---|---|---|
| 1 | 4939 | 3.87 | 61.92 | 0.0125 |
| 2 | 2215 | 3.30 | 52.86 | 0.0239 |
| 3 | 4470 | 3.95 | 63.12 | 0.0141 |
| 4 | 3285 | 3.72 | 59.53 | 0.018 |
| 5 | 2243 | 3.91 | 62.60 | 0.028 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A multimeric protein structure comprising two α-galactosidase monomers, the protein structure being a dimeric protein structure, said two α-galactosidase monomers being covalently linked to one another via a linking moiety, the multimeric protein structure featuring a characteristic selected from the group consisting of:
    (a) an α-galactosidase activity upon subjecting the multimeric protein structure to human plasma conditions for one hour, which is at least 10% higher than an activity of native α-galactosidase upon subjecting said native α-galactosidase to said human plasma conditions for one hour;
    (b) an α-galactosidase activity which decreases upon subjecting the multimeric protein structure to human plasma conditions for one hour by a percentage which is at least 10% less than the percentage by which an activity of said native α-galactosidase decreases upon subjecting said native α-galactosidase to said human plasma conditions for one hour;
    (c) an α-galactosidase activity which remains in a range of 50% to 150% of the initial activity upon subjecting the multimeric protein structure to human plasma conditions for one hour;
    (d) an α-galactosidase activity, upon subjecting the multimeric protein structure to lysosomal conditions for one week, which is at least 10% higher than an activity of native α-galactosidase upon subjecting said native α-galactosidase to said lysosomal conditions for one week;
    (e) an α-galactosidase activity which decreases upon subjecting the multimeric protein structure to lysosomal conditions for one day by a percentage which is at least 10% less than the percentage by which an activity of said native α-galactosidase decreases upon subjecting said native α-galactosidase to said lysosomal conditions for one day;
    (f) an α-galactosidase activity which remains in a range of 50% to 150% of the initial activity upon subjecting the multimeric protein structure to lysosomal conditions for one day;
    (g) an α-galactosidase activity, immediately upon subjecting the multimeric protein structure to lysosomal conditions, which is at least 10% higher than an activity of native α-galactosidase immediately upon subjecting said native form of said protein to said lysosomal conditions;
    (h) an α-galactosidase activity, immediately upon subjecting the multimeric protein structure to an aqueous solution having a pH of 7 and a temperature of 37° C., which is at least 10% higher than an activity of native α-galactosidase immediately upon subjecting said native α-galactosidase to said aqueous solution having a pH of 7 and a temperature of 37° C.; and
    (i) a circulating half-life in human plasma which is higher by at least 20% than said circulating half-life of said native α-galactosidase, wherein said α-galactosidase has an amino acid sequence selected from the group consisting of SEQ ID NO:1, SEQ ID NO:2 and SEQ ID NO:3.

2. The multimeric protein structure of claim 1, wherein said α-galactosidase activity of said multimeric protein structure which remains in a range of 50% to 150% of the initial activity upon subjecting the multimeric protein structure to lysosomal conditions for one day, further remains in a range of 50% to 150% of the initial activity upon subjecting the multimeric protein structure to lysosomal conditions for one week.

3. The multimeric protein structure of claim 1, characterized by an α-galactosidase activity in an organ upon administration of said multimeric protein structure to a vertebrate, said organ being selected from the group consisting of a spleen, a heart and a kidney.

4. The multimeric protein structure of claim 1, wherein said α-galactosidase is a plant recombinant α-galactosidase.

5. The multimeric protein structure of claim 1, wherein said linking moiety comprises a poly(alkylene glycol).

6. The multimeric protein structure of claim 5, wherein said poly(alkylene glycol) comprises at least two functional groups, each functional group forming a covalent bond with one of the α-galactosidase monomers.

7. The multimeric protein structure of claim 6, wherein said at least two functional groups are terminal groups of said poly(alkylene glycol).

8. The multimeric protein structure of claim 1, wherein said at least one linking moiety has a general formula:

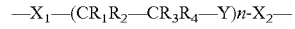

wherein each of $X_1$ and $X_2$ is a functional group that forms a covalent bond with at least one α-galactosidase monomer;
C is a carbon atom;
Y is an oxygen atom, a sulfur atom or $NR_5$, wherein $NR_5$ is a nitrogen atom attached to $R_5$;
n is an integer from 1 to 200; and
each of $R_1$, $R_2$, $R_3$, $R_4$ and $R_5$ is independently selected from the group consisting of hydrogen, alkyl, cycloalkyl, alkenyl, alkynyl, alkoxy, hydroxy, oxo, thiol and thioalkoxy.

9. A multimeric protein structure comprising two α-galactosidase monomers, the protein structure being a dimeric protein structure, said two α-galactosidase monomers being covalently linked to one another via a linking moiety, and said α-galactosidase comprising an amino acid sequence having at least 95% sequence identity to SEQ ID NO: 15.

10. The multimeric protein structure of claim 9, featuring a characteristic selected from the group consisting of:
    (a) an α-galactosidase activity, upon subjecting the multimeric protein structure to human plasma conditions for one hour, which is at least 10% higher than an activity of native α-galactosidase upon subjecting said native α-galactosidase to said human plasma conditions for one hour;

(b) an α-galactosidase activity which decreases upon subjecting the multimeric protein structure to human plasma conditions for one hour by a percentage which is at least 10% less than the percentage by which an activity of said native α-galactosidase decreases upon subjecting said native α-galactosidase to said human plasma conditions for one hour;

(c) an α-galactosidase activity which remains in a range of 50% to 150% of the initial activity upon subjecting the multimeric protein structure to human plasma conditions for one hour;

(d) an α-galactosidase activity, upon subjecting the multimeric protein structure to lysosomal conditions for one week, which is at least 10% higher than an activity of native α-galactosidase upon subjecting said native α-galactosidase to said lysosomal conditions for one week;

(e) an α-galactosidase activity which decreases upon subjecting the multimeric protein structure to lysosomal conditions for one day by a percentage which is at least 10% less than the percentage by which an activity of said native α-galactosidase decreases upon subjecting said native α-galactosidase to said lysosomal conditions for one day;

(f) an α-galactosidase activity which remains in a range of 50% to 150% of the initial activity upon subjecting the multimeric protein structure to lysosomal conditions for one day;

(g) an α-galactosidase activity, immediately upon subjecting the multimeric protein structure to lysosomal conditions, which is at least 10% higher than an activity of native α-galactosidase immediately upon subjecting said native α-galactosidase to said lysosomal conditions;

(h) an α-galactosidase activity, immediately upon subjecting the multimeric protein structure to an aqueous solution having a pH of 7 and a temperature of 37° C., which is at least 10% higher than an activity of native α-galactosidase immediately upon subjecting said native α-galactosidase to said aqueous solution having a pH of 7 and a temperature of 37° C.; and (i) a circulating half-life in human plasma which is higher than a circulating half-life of said native α-galactosidase.

11. The multimeric protein structure of claim 10, wherein said α-galactosidase activity of said multimeric protein structure which remains in a range of 50% to 150% of the initial activity upon subjecting the multimeric protein structure to lysosomal conditions for one day, further remains in a range of 50% to 150% of the initial activity upon subjecting the multimeric protein structure to lysosomal conditions for one week.

12. The multimeric protein structure of claim 10, wherein said circulating half-life of the multimeric protein structure which is higher than a circulating half-life of said native α-galactosidase, is higher by at least 20% than said circulating half-life of said native α-galactosidase.

13. The multimeric protein structure of claim 9, characterized by an α-galactosidase activity in an organ upon administration of said multimeric protein structure to a vertebrate, said organ being selected from the group consisting of a spleen, a heart and a kidney.

14. The multimeric protein structure of claim 9, wherein said α-galactosidase is a human α-galactosidase selected from the group consisting of agalsidase alpha and agalsidase beta.

15. The multimeric protein structure of claim 9, wherein said α-galactosidase is a plant recombinant α-galactosidase.

16. The multimeric protein structure of claim 9, wherein said α-galactosidase has an amino acid sequence selected from the group consisting of SEQ ID NO:1, SEQ ID NO:2 and SEQ ID NO:3.

17. The multimeric protein structure of claim 9, wherein said linking moiety comprises a poly(alkylene glycol).

18. The multimeric protein structure of claim 17, wherein said poly(alkylene glycol) comprises at least two functional groups, each functional group forming a covalent bond with one of the α-galactosidase monomers.

19. The multimeric protein structure of claim 18, wherein said at least two functional groups are terminal groups of said poly(alkylene glycol).

20. The multimeric protein structure of claim 9, wherein said at least one linking moiety has a general formula:

$$-X_1-(CR_1R_2-CR_3R_4-Y)n-X_2-$$

wherein each of $X_1$ and $X_2$ is a functional group that forms a covalent bond with at least one α-galactosidase monomer;

C is a carbon atom;

Y is an oxygen atom, a sulfur atom or $NR_5$, wherein $NR_5$ is a nitrogen atom attached to $R_5$;

n is an integer from 1 to 200; and each of $R_1$, $R_2$, $R_3$, $R_4$ and $R_5$ is independently selected from the group consisting of hydrogen, alkyl, cycloalkyl, alkenyl, alkynyl, alkoxy, hydroxy, oxo, thiol and thioalkoxy.

21. A pharmaceutical composition comprising the multimeric protein structure of claim 1 and a pharmaceutically acceptable carrier.

22. The pharmaceutical composition of claim 21, further comprising, as an additional ingredient, a galactose.

23. A pharmaceutical composition comprising the multimeric protein structure of claim 9 and a pharmaceutically acceptable carrier.

24. The pharmaceutical composition of claim 23, further comprising, as an additional ingredient, a galactose.

25. A method of treating Fabry disease, the method comprising administering to a subject in need thereof a therapeutically effective amount of the multimeric protein structure of claim 1, thereby treating the Fabry disease.

26. A method of treating Fabry disease, the method comprising administering to a subject in need thereof a therapeutically effective amount of the multimeric protein structure of claim 9, thereby treating the Fabry disease.

27. A process of preparing the multimeric protein structure of claim 1, the process comprising reacting α-galactosidase with a cross-linking agent which comprises said linking moiety and at least two reactive groups.

28. The process of claim 27, comprising reacting dimeric α-galactosidase with said cross-linking agent.

29. The process of claim 27, wherein said reactive groups comprise a leaving group.

30. The process of claim 27, wherein said reactive group reacts with an amine group to form an amide bond.

31. The process of claim 27, wherein each of said reactive groups is capable of forming a covalent bond between said linking moiety and at least one α-galactosidase monomer.

32. The process of claim 27, wherein a molar ratio of said cross-linking agent to monomers of said α-galactosidase is in a range of from 5:1 to 500:1.

33. A process of preparing the multimeric protein structure of claim 9, the process comprising reacting α-galactosidase with a cross-linking agent which comprises said linking moiety and at least two reactive groups.

34. The multimeric protein structure of claim 1, wherein said α-galactosidase is a recombinant α-galactosidase.

35. The multimeric protein structure of claim 1, wherein said linking moiety is at least 20 atoms long.

36. The multimeric protein structure of claim 8, wherein n is at least 25.

37. The multimeric protein structure of claim 9, wherein said α-galactosidase is a recombinant α-galactosidase.

38. The multimeric protein structure of claim 9, wherein said linking moiety is at least 20 atoms long.

39. The multimeric protein structure of claim 20, wherein n is at least 25.

40. The multimeric protein structure of claim 20, wherein said α-galactosidase has an amino acid sequence selected from the group consisting of SEQ ID NO:1, SEQ ID NO:2 and SEQ ID NO:3, each of said functional groups forms an amide bond with an α-galactosidase monomer, and n is an integer from 40 to 70.

41. The multimeric protein structure of claim 16, wherein said linking moiety has the formula:

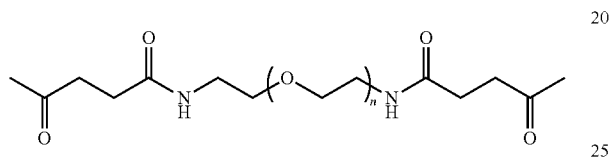

wherein a molecular weight of polyethylene glycol in said linking moiety is 2 kDa, and the terminal groups of said linking moiety each form an amide bond with an α-galactosidase monomer.

* * * * *